United States Patent
Savage et al.

(10) Patent No.: US 11,180,778 B2
(45) Date of Patent: Nov. 23, 2021

(54) VARIANT RNA-GUIDED POLYPEPTIDES AND METHODS OF USE

(71) Applicant: The Regents of the University of California, Oakland, CA (US)

(72) Inventors: David Frank Savage, Berkeley, CA (US); Jennifer A. Doudna, Berkeley, CA (US); Benjamin L. Oakes, Berkeley, CA (US); Rayka Yokoo, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 373 days.

(21) Appl. No.: 16/342,862

(22) PCT Filed: Nov. 9, 2017

(86) PCT No.: PCT/US2017/060905
§ 371 (c)(1),
(2) Date: Apr. 17, 2019

(87) PCT Pub. No.: WO2018/089664
PCT Pub. Date: May 17, 2018

(65) Prior Publication Data
US 2019/0233847 A1    Aug. 1, 2019

Related U.S. Application Data

(60) Provisional application No. 62/421,146, filed on Nov. 11, 2016.

(51) Int. Cl.
| | | |
|---|---|---|
| *C12N 15/90* | (2006.01) | |
| *C12N 15/113* | (2010.01) | |
| *C12N 15/74* | (2006.01) | |
| *C12N 15/79* | (2006.01) | |
| *C12N 9/22* | (2006.01) | |

(52) U.S. Cl.
CPC ............ *C12N 15/907* (2013.01); *C12N 9/22* (2013.01); *C12N 15/113* (2013.01); *C12N 15/74* (2013.01); *C12N 15/79* (2013.01); *C07K 2319/50* (2013.01)

(58) Field of Classification Search
None
See application file for complete search history.

(56) References Cited

U.S. PATENT DOCUMENTS

2015/0023912 A1    1/2015   Kratz et al.

FOREIGN PATENT DOCUMENTS

| WO | WO 2016/114972 | 7/2016 |
| WO | WO 2016/196655 | 12/2016 |
| WO | WO 2016/201138 | 12/2016 |

OTHER PUBLICATIONS

Oakes, et al.; "Profiling of engineering hotspots identifies an allosteric CRISPR-Cas9 switch"; Nat. Biotechnol.; vol. 34, No. 6, pp. 646-651 (Jun. 2016).
Truong, et al.; "Development of an intein-mediated split-Cas9 system for gene therapy"; Nucleic Acids Research; vol. 43, No. 13, pp. 6450-6458 (2015).
Oakes, et al.; CRISPR-Cas9 Circular Permutants as Programmable Scaffolds for Genome Modification; CELL; vol. 176, pp. 254-267 (Jan. 10, 2019).

*Primary Examiner* — Suzanne M Noakes
*Assistant Examiner* — Jae W Lee
(74) *Attorney, Agent, or Firm* — Bozicevic Field & Francis, LLP; Paula A. Borden

(57) ABSTRACT

The present disclosure provides (i) RNA-guided polypeptides (e.g., circular permuted Cas9 proteins) in which the N-terminal end of an N-terminal fragment of a parent RNA-guided polypeptide (e.g., a parent Cas9 protein) is fused (e.g., via linker) to the C-terminal end of the C-terminal fragment (thereby generating new N- and C-termini), (ii) conditionally active RNA-guided polypeptides (e.g., conditionally active circular permuted Cas9 proteins), and (iii) Cas9 fusion polypeptides that include an internal insertion of a heterologous polypeptide; as well as methods that employ the above polypeptides.

17 Claims, 43 Drawing Sheets
Specification includes a Sequence Listing.

Figure 1

\* NOTE: the 20Xs present in each sequence below represent the position of the linker between the original C- and N- termini, where the original C-terminus '...GGD' is now positioned N-terminal to the original N-terminus 'MDK...'; the linker can be a variety of lengths and is not necessarily 20 amino acids long.

```
>CircularPermutant_1 ["CP1"]
     [new start-MMD; insert site-182D]
MMDKLFIQLVQTYNQLFEENPINASGVDAKAILSARLSKSRRLENLIAQLPGEKKNGLF
GNLIALSLGLTPNFKSNFDLAEDAKLQLSKDTYDDDLDNLLAQIGDQYADLFLAAKNLS
DAILLSDILRVNTEITKAPLSASMIKRYDEHHQDLTLLKALVRQQLPEKYKEIFFDQSK
NGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETIT
PWNFEEVVDKGASAQSFIERMTNFDKNLPNEKVLPKHSLLYEYFTVYNELTKVKYVTEG
MRKPAFLSGEQKKAIVDLLFKTNRKVTVKQLKEDYFKKIECFDSVEISGVEDRFNASLG
TYHDLLKIIKDKDFLDNEENEDILEDIVLTLTLFEDREMIEERLKTYAHLFDDKVMKQL
KRRRYTGWGRLSRKLINGIRDKQSGKTILDFLKSDGFANRNFMQLIHDDSLTFKEDIQK
AQVSGQGDSLHEHIANLAGSPAIKKGILQTVKVVDELVKVMGRHKPENIVIEMARENQT
TQKGQKNSRERMKRIEEGIKELGSQILKEHPVENTQLQNEKLYLYYLQNGRDMYVDQEL
DINRLSDYDVDAIVPQSFLKDDSIDNKVLTRSDKNRGKSDNVPSEEVVKKMKNYWRQLL
NAKLITQRKFDNLTKAERGGLSELDKAGFIKRQLVETRQITKHVAQILDSRMNTKYDEN
DKLIREVKVITLKSKLVSDFRKDFQFYKVREINNYHHAHDAYLNAVVGTALIKKYPKLE
SEFVYGDYKVYDVRKMIAKSEQEIGKATAKYFFYSNIMNFFKTEITLANGEIRKRPLIE
TNGETGEIVWDKGRDFATVRKVLSMPQVNIVKKTEVQTGGFSKESILPKRNSDKLIARK
KDWDPKKYGGFDSPTVAYSVLVVAKVEKGKSKKLKSVKELLGITIMERSSFEKNPIDFL
EAKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQSITGLYETR
IDLSQLGGDXXXXXXXXXXXXXXXXXXXXMDKKYSIGLAIGTNSVGWAVITDEYKVPSK
KFKVLGNTDRHSIKKNLIGALLFDSGETAEATRLKRTARRRYTRRKNRICYLQEIFSNE
MAKVDDSFFHRLEESFLVEEDKKHERHPIFGNIVDEVAYHEKYPTIYHLRKKLVDSTDK
ADLRLIYLALAHMIKFRGHFLIEGDLNPDNSDVD     (SEQ ID NO: 1)

>CircularPermutant_2 ["CP2"]
     [new start-MNP; insert site-200P]
MNPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKA
PLSASMIKRYDEHHQDLTLLKALVRQQLPEKYKEIFFDQSKNGYAGYIDGGASQEEFYK
FIKPILEKMDGTEELLVKLNREDLLRKQRTFDNGSIPHQIHLGELHAILRRQEDFYPFL
KDNREKIEKILTFRIPYYVGPLARGNSRFAWMTRKSEETITPWNFEEVVDKGASAQSFI
ERMTNFDKNLPNEKVLPKHSLLYEYFTVYNELTKVKYVTEGMRKPAFLSGEQKKAIVDL
LFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLING
IRDKQSGKTILDFLKSDGFANRNFMQLIHDDSLTFKEDIQKAQVSGQGDSLHEHIANLA
GSPAIKKGILQTVKVVDELVKVMGRHKPENIVIEMARENQTTQKGQKNSRERMKRIEEG
```

Figure 1 (Cont. 1)

```
IKELGSQILKEHPVENTQLQNEKLYLYYLQNGRDMYVDQELDINRLSDYDVDAIVPQSF
LKDDSIDNKVLTRSDKNRGKSDNVPSEEVVKKMKNYWRQLLNAKLITQRKFDNLTKAER
GGLSELDKAGFIKRQLVETRQITKHVAQILDSRMNTKYDENDKLIREVKVITLKSKLVS
DFRKDFQFYKVREINNYHHAHDAYLNAVVGTALIKKYPKLESEFVYGDYKVYDVRKMIA
KSEQEIGKATAKYFFYSNIMNFFKTEITLANGEIRKRPLIETNGETGEIVWDKGRDFAT
VRKVLSMPQVNIVKKTEVQTGGFSKESILPKRNSDKLIARKKDWDPKKYGGFDSPTVAY
SVLVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQKQLFV
EQHKHYLDEIIEQISEFSKRVILADANLDKVLSAYNKHRDKPIREQAENIIHLFTLTNL
GAPAAFKYFDTTIDRKRYTSTKEVLDATLIHQSITGLYETRIDLSQLGGD**XXXXXXXXX
XXXXXXXXXX**MDKKYSIGLAIGTNSVGWAVITDEYKVPSKKFKVLGNTDRHSIKKNLI
GALLFDSGETAEATRLKRTARRRYTRRKNRICYLQEIFSNEMAKVDDSFFHRLEESFLV
EEDKKHERHPIFGNIVDEVAYHEKYPTIYHLRKKLVDSTDKADLRLIYLALAHMIKFRG
HFLIEGDLNPDNSDVDKLFIQLVQTYNQLFEENP          (SEQ ID NO: 2)

>CircularPermutant_3 ["CP3"]
        [new start-MTG; insert site-231G]
MTGEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTF
DNGSIPHQIHLGELHAILRRQEDFYPFLKDNREKIEKILTFRIPYYVGPLARGNSRFAW
MTRKSEETITPWNFEEVVDKGASAQSFIERMTNFDKNLPNEKVLPKHSLLYEYFTVYNE
LTKVKYVTEGMRKPAFLSGEQKKAIVDLLFKTNRKVTVKQLKEDYFKKIECFDSVEISG
VEDRFNASLGTYHDLLKIIKDKDFLDNEENEDILEDIVLTLTLFEDREMIEERLKTYAH
LFDDKVMKQLKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKVMGRHKPENI
VIEMARENQTTQKGQKNSRERMKRIEEGIKELGSQILKEHPVENTQLQNEKLYLYYLQN
GRDMYVDQELDINRLSDYDVDAIVPQSFLKDDSIDNKVLTRSDKNRGKSDNVPSEEVVK
KMKNYWRQLLNAKLITQRKFDNLTKAERGGLSELDKAGFIKRQLVETRQITKHVAQILD
SRMNTKYDENDKLIREVKVITLKSKLVSDFRKDFQFYKVREINNYHHAHDAYLNAVVGT
ALIKKYPKLESEFVYGDYKVYDVRKMIAKSEQEIGKATAKYFFYSNIMNFFKTEITLAN
GEIRKRPLIETNGETGEIVWDKGRDFATVRKVLSMPQVNIVKKTEVQTGGFSKESILPK
RNSDKLIARKKDWDPKKYGGFDSPTVAYSVLVVAKVEKGKSKKLKSVKELLGITIMERS
SFEKNPIDFLEAKGYKEVKKDLIIKLPKYSLFELENGRKRMLASAGELQKGNELALPSK
YVNFLYLASHYEKLKGSPEDNEQKQLFVEQHKHYLDEIIEQISEFSKRVILADANLDKV
LSAYNKHRDKPIREQAENIIHLFTLTNLGAPAAFKYFDTTIDRKRYTSTKEVLDATLIH
QSITGLYETRIDLSQLGGDXXXXXXXXXXXXXXXXXXXXMDKKYSIGLAIGTNSVGWAV
ITDEYKVPSKKFKVLGNTDRHSIKKNLIGALLFDSGETAEATRLKRTARRRYTRRKNRI
CYLQEIFSNEMAKVDDSFFHRLEESFLVEEDKKHERHPIFGNIVDEVAYHEKYPTIYHL
RKKLVDSTDKADLRLIYLALAHMIKFRGHFLIEGDLNPDNSDVDKLFIQLVQTYNQLFE
ENPINASGVDAKAILSARLSKSRRLENLIAQLPG         (SEQ ID NO: 3)
```

Figure 1 (Cont. 2)

```
>CircularPermutant_4  ["CP4"]
     [new start-MTY; insert site-271Y]
MTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGT
EELLVKLNREDLLRKQRTFDNGSIPHQIHLGELHAILRRQEDFYPFLKDNREKIEKILT
FRIPYYVGPLARGNSRFAWMTRKSEETITPWNFEEVVDKGASAQSFIERMTNFDKNLPN
EKVLPKHSLLYEYFTVYNELTKVKYVTEGMRKPAFLSGEQKKAIVDLLFKTNRKVTVKQ
LKEDYFKKIECFDSVEISGVEDRFNASLGTYHDLLKIIKDKDFLDNEENEDILEDIVLT
LTLFEDREMIEERLKTYAHLFDDKVMKQLKRRRYTGWGRLSRKLINGIRDKQSGKTILD
FLKSDGFANRNFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEH
PVENTQLQNEKLYLYYLQNGRDMYVDQELDINRLSDYDVDAIVPQSFLKDDSIDNKVLT
RSDKNRGKSDNVPSEEVVKKMKNYWRQLLNAKLITQRKFDNLTKAERGGLSELDKAGFI
KRQLVETRQITKHVAQILDSRMNTKYDENDKLIREVKVITLKSKLVSDFRKDFQFYKVR
EINNYHHAHDAYLNAVVGTALIKKYPKLESEFVYGDYKVYDVRKMIAKSEQEIGKATAK
YFFYSNIMNFFKTEITLANGEIRKRPLIETNGETGEIVWDKGRDFATVRKVLSMPQVNI
VKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKR
MLASAGELQKGNELALPSKYVNFLYLASHYEKLKGSPEDNEQKQLFVEQHKHYLDEIIE
QISEFSKRVILADANLDKVLSAYNKHRDKPIREQAENIIHLFTLTNLGAPAAFKYFDTT
IDRKRYTSTKEVLDATLIHQSITGLYETRIDLSQLGGDXXXXXXXXXXXXXXXXXXXXXM
DKKYSIGLAIGTNSVGWAVITDEYKVPSKKFKVLGNTDRHSIKKNLIGALLFDSGETAE
ATRLKRTARRRYTRRKNRICYLQEIFSNEMAKVDDSFFHRLEESFLVEEDKKHERHPIF
GNIVDEVAYHEKYPTIYHLRKKLVDSTDKADLRLIYLALAHMIKFRGHFLIEGDLNPDN
SDVDKLFIQLVQTYNQLFEENPINASGVDAKAILSARLSKSRRLENLIAQLPGEKKNGL
FGNLIALSLGLTPNFKSNFDLAEDAKLQLSKDTY  (SEQ ID NO: 4)

>CircularPermutant_5  ["CP5"]
     [new start-MTE; insert site-311E]
MTEITKAPLSASMIKRYDEHHQDLTLLKALVRQQLPEKYKEIFFDQSKNGYAGYIDGGA
SQEEFYKFIKPILEKMDGTEELLVKLNREDLLRKQRTFDNGSIPHQIHLGELHAILRRQ
EDFYPFLKDNREKIEKILTFRIPYYVGPLARGNSRFAWMTRKSEETITPWNFEEVVDKG
ASAQSFIERMTNFDKNLPNEKVLPKHSLLYEYFTVYNELTKVKYVTEGMRKPAFLSGEQ
KKAIVDLLFKTNRKVTVKQLKEDYFKKIECFDSVEISGVEDRFNASLGTYHDLLKIIKD
KDFLDNEENEDILEDIVLTLTLFEDREMIEERLKTYAHLFDDKVMKQLKRRRYTGWGRL
SRKLINGIRDKQSGKTILDFLKSDGFANRNFMQLIHDDSLTFKEDIQKAQVSGQGDSLH
EHIANLAGSPAIKKGILQTVKVVDELVKVMGRHKPENIVIEMARENQTTQKGQKNSRER
MKRIEEGIKELGSQILKEHPVENTQLQNEKLYLYYLQNGRDMYVDQELDINRLSDYDVD
AIVPQSFLKDDSIDNKVLTRSDKNRGKSDNVPSEEVVKKMKNYWRQLLNAKLITQRKFD
NLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKYGGF
DSPTVAYSVLVVAKVEKGKSKKLKSVKELLGITIMERSSFEKNPIDFLEAKGYKEVKKD
```

Figure 1 (Cont. 3)

LIIKLPKYSLFELENGRKRMLASAGELQKGNELALPSKYVNFLYLASHYEKLKGSPEDN
EQKQLFVEQHKHYLDEIIEQISEFSKRVILADANLDKVLSAYNKHRDKPIREQAENIIH
LFTLTNLGAPAAFKYFDTTIDRKRYTSTKEVLDATLIHQSITGLYETRIDLSQLGGDXX
XXXXXXXXXXXXXXXXXXXXMDKKYSIGLAIGTNSVGWAVITDEYKVPSKKFKVLGNTDRH
SIKKNLIGALLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKADLRLIYLALA
HMIKFRGHFLIEGDLNPDNSDVDKLFIQLVQTYNQLFEENPINASGVDAKAILSARLSK
SRRLENLIAQLPGEKKNGLFGNLIALSLGLTPNFKSNFDLAEDAKLQLSKDTYDDDLDN
LLAQIGDQYADLFLAAKNLSDAILLSDILRVNTE      (SEQ ID NO: 5)

>CircularPermutant_6  ["CP6"]
       [new start-MNG; insert site-1011G]
MNGDYKVYDVRKMIAKSEQEIGKATAKYFFYSNIMNFFKTEITLANGEIRKRPLIETNG
ETGEIVWDKGRDFATVRKVLSMPQVNIVKKTEVQTGGFSKESILPKRNSDKLIARKKDW
DPKKYGGFDSPTVAYSVLVVAKVEKGKSKKLKSVKELLGITIMERSSFEKNPIDFLEAK
GYKEVKKDLIIKLPKYSLFELENGRKRMLASAGELQKGNELALPSKYVNFLYLASHYEK
LKGSPEDNEQKQLFVEQHKHYLDEIIEQISEFSKRVILADANLDKVLSAYNKHRDKPIR
EQAENIIHLFTLTNLGAPAAFKYFDTTIDRKRYTSTKEVLDATLIHQSITGLYETRIDL
SQLGGDXXXXXXXXXXXXXXXXXXXXXXMDKKYSIGLAIGTNSVGWAVITDEYKVPSKKFK
VLGNTDRHSIKKNLIGALLFDSGETAEATRLKRTARRRYTRRKNRICYLQEIFSNEMAK
VDDSFFHRLEESFLVEEDKKHERHPIFGNIVDEVAYHEKYPTIYHLRKKLVDSTDKADL
RLIYLALAHMIKFRGHFLIEGDLNPDNSDVDKLFIQLVQTYNQLFEENPINASGVDAKA
ILSARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDEH
HQDLTLLKALVRQQLPEKYKEIFFDQSKNGYAGYIDGGASQEEFYKFIKPILEKMDGTE
ELLVKLNREDLLRKQRTFDNGSIPHQIHLGELHAILRRQEDFYPFLKDNREKIEKILTF
RIPYYVGPLARGNSRFAWMTRKSEETITPWNFEEVVDKGASAQSFIERMTNFDKNLPNE
KVLPKHSLLYEYFTVYNELTKVKYVTEGMRKPAFLSGEQKKAIVDLLFKTNRKVTVQL
KEDYFKKIECFDSVEISGVEDRFNASLGTYHDLLKIIKDKDFLDNEENEDILEDIVLTL
TLFEDREMIEERLKTYAHLFDDKVMKQLKRRRYTGWGRLSRKLINGIRDKQSGKTILDF
LKSDGFANRNFMQLIHDDSLTFKEDIQKAQVSGQGDSLHEHIANLAGSPAIKKGILQTV
KVVDELVKVMGRHKPENIVIEMARENQTTQKGQKNSRERMKRIEEGIKELGSQILKEHP
VENTQLQNEKLYLYYLQNGRDMYVDQELDINRLSDYDVDAIVPQSFLKDDSIDNKVLTR
SDKNRGKSDNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKDFQFYKVRE
INNYHHAHDAYLNAVVGTALIKKYPKLESEFVYG      (SEQ ID NO: 6)

Figure 1 (Cont. 4)

\>CircularPermutant_7 ["CP7"]
    [new start-MND; insert site-1017D]
MNDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPKKYG
GFDSPTVAYSVLVVAKVEKGKSKKLKSVKELLGITIMERSSFEKNPIDFLEAKGYKEVK
KDLIIKLPKYSLFELENGRKRMLASAGELQKGNELALPSKYVNFLYLASHYEKLKGSPE
DNEQKQLFVEQHKHYLDEIIEQISEFSKRVILADANLDKVLSAYNKHRDKPIREQAENI
IHLFTLTNLGAPAAFKYFDTTIDRKRYTSTKEVLDATLIHQSITGLYETRIDLSQLGGD
XXXXXXXXXXXXXXXXXXXXMDKKYSIGLAIGTNSVGWAVITDEYKVPSKKFKVLGNTD
RHSIKKNLIGALLFDSGETAEATRLKRTARRRYTRRKNRICYLQEIFSNEMAKVDDSFF
HRLEESFLVEEDKKHERHPIFGNIVDEVAYHEKYPTIYHLRKKLVDSTDKADLRLIYLA
LAHMIKFRGHFLIEGDLNPDNSDVDKLFIQLVQTYNQLFEENPINASGVDAKAILSARL
SKSRRLENLIAQLPGEKKNGLFGNLIALSLGLTPNFKSNFDLAEDAKLQLSKDTYDDDL
DNLLAQIGDQYADLFLAAKNLSDAILLSDILRVNTEITKAPLSASMIKRYDEHHQDLTL
LKALVRQQLPEKYKEIFFDQSKNGYAGYIDGGASQEEFYKFIKPILEKMDGTEELLVKL
NREDLLRKQRTFDNGSIPHQIHLGELHAILRRQEDFYPFLKDNREKIEKILTFRIPYYV
GPLARGNSRFAWMTRKSEETITPWNFEEVVDKGASAQSFIERMTNFDKNLPNEKVLPKH
SLLYEYFTVYNELTKVKYVTEGMRKPAFLSGEQKKAIVDLLFKTNRKVTVKQLKEDYFK
KIECFDSVEISGVEDRFNASLGTYHDLLKIIKDKDFLDNEENEDILEDIVLTLTLFEDR
EMIEERLKTYAHLFDDKVMKQLKRRRYTGWGRLSRKLINGIRDKQSGKTILDFLKSDGF
ANRNFMQLIHDDSLTFKEDIQKAQVSGQGDSLHEHIANLAGSPAIKKGILQTVKVVDEL
VKVMGRHKPENIVIEMARENQTTQKGQKNSRERMKRIEEGIKELGSQILKEHPVENTQL
QNEKLYLYYLQNGRDMYVDQELDINRLSDYDVDAIVPQSFLKDDSIDNKVLTRSDKNRG
KSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHH
AHDAYLNAVVGTALIKKYPKLESEFVYGDYKVYD    (SEQ ID NO: 7)

\>CircularPermutant_8 ["CP8"]
    [new start-MTK; insert site-1024K]
MTKSEQEIGKATAKYFFYSNIMNFFKTEITLANGEIRKRPLIETNGETGEIVWDKGRDF
ATVRKVLSMPQVNIVKKTEVQTGGFSKESILPKRNSDKLIARKKDWDPKKYGGFDSPTV
AYSVLVVAKVEKGKSKKLKSVKELLGITIMERSSFEKNPIDFLEAKGYKEVKKDLIIKL
PKYSLFELENGRKRMLASAGELQKGNELALPSKYVNFLYLASHYEKLKGSPEDNEQKQL
FVEQHKHYLDEIIEQISEFSKRVILADANLDKVLSAYNKHRDKPIREQAENIIHLFTLT
NLGAPAAFKYFDTTIDRKRYTSTKEVLDATLIHQSITGLYETRIDLSQLGGD**XXXXXXX
XXXXXXXXXXXXX**MDKKYSIGLAIGTNSVGWAVITDEYKVPSKKFKVLGNTDRHSIKKN
LIGALLFDSGETAEATRLKRTARRRYTRRKNRICYLQEIFSNEMAKVDDSFFHRLEESF
LVEEDKKHERHPIFGNIVDEVAYHEKYPTIYHLRKKLVDSTDKADLRLIYLALAHMIKF
RGHFLIEGDLNPDNSDVDKLFIQLVQTYNQLFEENPINASGVDAKAILSARLSKSRRLE
NLIAQLPGEKKNGLFGNLIALSLGLTPNFKSNFDLAEDAKLQLSKDTYDDDLDNLLAQI
GDQYADLFLAAKNLSDAILLSDILRVNTEITKAPLSASMIKRYDEHHQDLTLLKALVRQ
QLPEKYKEIFFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPYYVGPLARGN
SRFAWMTRKSEETITPWNFEEVVDKGASAQSFIERMTNFDKNLPNEKVLPKHSLLYEYF

Figure 1 (Cont. 5)

TVYNELTKVKYVTEGMRKPAFLSGEQKKAIVDLLFKTNRKVTVKQLKEDYFKKIECFDS
VEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQ
LIHDDSLTFKEDIQKAQVSGQGDSLHEHIANLAGSPAIKKGILQTVKVVDELVKVMGRH
KPENIVIEMARENQTTQKGQKNSRERMKRIEEGIKELGSQILKEHPVENTQLQNEKLYL
YYLQNGRDMYVDQELDINRLSDYDVDAIVPQSFLKDDSIDNKVLTRSDKNRGKSDNVPS
EEVVKKMKNYWRQLLNAKLITQRKFDNLTKAERGGLSELDKAGFIKRQLVETRQITKHV
AQILDSRMNTKYDENDKLIREVKVITLKSKLVSDFRKDFQFYKVREINNYHHAHDAYLN
AVVGTALIKKYPKLESEFVYGDYKVYDVRKMIAK   (SEQ ID NO: 8)

\>CircularPermutant_9  ["CP9"]
      [new start-MKI; insert site-1029I]
MKIGKATAKYFFYSNIMNFFKTEITLANGEIRKRPLIETNGETGEIVWDKGRDFATVRK
VLSMPQVNIVKKTEVQTGGFSKESILPKRNSDKLIARKKDWDPKKYGGFDSPTVAYSVL
VVAKVEKGKSKKLKSVKELLGITIMERSSFEKNPIDFLEAKGYKEVKKDLIIKLPKYSL
FELENGRKRMLASAGELQKGNELALPSKYVNFLYLASHYEKLKGSPEDNEQKQLFVEQH
KHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD**XXXXXXXXXXXX
XXXXXXX**MDKKYSIGLAIGTNSVGWAVITDEYKVPSKKFKVLGNTDRHSIKKNLIGAL
LFDSGETAEATRLKRTARRRYTRRKNRICYLQEIFSNEMAKVDDSFFHRLEESFLVEED
KKHERHPIFGNIVDEVAYHEKYPTIYHLRKKLVDSTDKADLRLIYLALAHMIKFRGHFL
IEGDLNPDNSDVDKLFIQLVQTYNQLFEENPINASGVDAKAILSARLSKSRRLENLIAQ
LPGEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPEK
YKEIFFDQSKNGYAGYIDGGASQEEFYKFIKPILEKMDGTEELLVKLNREDLLRKQRTF
DNGSIPHQIHLGELHAILRRQEDFYPFLKDNREKIEKILTFRIPYYVGPLARGNSRFAW
MTRKSEETITPWNFEEVVDKGASAQSFIERMTNFDKNLPNEKVLPKHSLLYEYFTVYNE
LTKVKYVTEGMRKPAFLSGEQKKAIVDLLFKTNRKVTVKQLKEDYFKKIECFDSVEISG
VEDRFNASLGTYHDLLKIIKDKDFLDNEENEDILEDIVLTLTLFEDREMIEERLKTYAH
LFDDKVMKQLKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKVMGRHKPENI
VIEMARENQTTQKGQKNSRERMKRIEEGIKELGSQILKEHPVENTQLQNEKLYLYYLQN
GRDMYVDQELDINRLSDYDVDAIVPQSFLKDDSIDNKVLTRSDKNRGKSDNVPSEEVVK
KMKNYWRQLLNAKLITQRKFDNLTKAERGGLSELDKAGFIKRQLVETRQITKHVAQILD
SRMNTKYDENDKLIREVKVITLKSKLVSDFRKDFQFYKVREINNYHHAHDAYLNAVVGT
ALIKKYPKLESEFVYGDYKVYDVRKMIAKSEQEI   (SEQ ID NO: 9)

Figure 1 (Cont. 6)

>CircularPermutant_10   ["CP10"]
       [new start-MIG; insert site-1030G]
MIGKATAKYFFYSNIMNFFKTEITLANGEIRKRPLIETNGETGEIVWDKGRDFATVRKV
LSMPQVNIVKKTEVQTGGFSKESILPKRNSDKLIARKKDWDPKKYGGFDSPTVAYSVLV
VAKVEKGKSKKLKSVKELLGITIMERSSFEKNPIDFLEAKGYKEVKKDLIIKLPKYSLF
ELENGRKRMLASAGELQKGNELALPSKYVNFLYLASHYEKLKGSPEDNEQKQLFVEQHK
HYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD**XXXXXXXXXXXXX
XXXXXXX**MDKKYSIGLAIGTNSVGWAVITDEYKVPSKKFKVLGNTDRHSIKKNLIGALL
FDSGETAEATRLKRTARRRYTRRKNRICYLQEIFSNEMAKVDDSFFHRLEESFLVEEDK
KHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQL
PGEKKNGLFGNLIALSLGLTPNFKSNFDLAEDAKLQLSKDTYDDDLDNLLAQIGDQYAD
LFLAAKNLSDAILLSDILRVNTEITKAPLSASMIKRYDEHHQDLTLLKALVRQQLPEKY
KEIFFDQSKNGYAGYIDGGASQEEFYKFIKPILEKMDGTEELLVKLNREDLLRKQRTFD
NGSIPHQIHLGELHAILRRQEDFYPFLKDNREKIEKILTFRIPYYVGPLARGNSRFAWM
TRKSEETITPWNFEEVVDKGASAQSFIERMTNFDKNLPNEKVLPKHSLLYEYFTVYNEL
TKVKYVTEGMRKPAFLSGEQKKAIVDLLFKTNRKVTVKQLKEDYFKKIECFDSVEISGV
EDRFNASLGTYHDLLKIIKDKDFLDNEENEDILEDIVLTLTLFEDREMIEERLKTYAHL
FDDKVMKQLKRRRYTGWGRLSRKLINGIRDKQSGKTILDFLKSDGFANRNFMQLIHDDS
LTFKEDIQKAQVSGQGDSLHEHIANLAGSPAIKKGILQTVKVVDELVKVMGRHKPENIV
IEMARENQTTQKGQKNSRERMKRIEEGIKELGSQILKEHPVENTQLQNEKLYLYYLQNG
RDMYVDQELDINRLSDYDVDAIVPQSFLKDDSIDNKVLTRSDKNRGKSDNVPSEEVVKK
MKNYWRQLLNAKLITQRKFDNLTKAERGGLSELDKAGFIKRQLVETRQITKHVAQILDS
RMNTKYDENDKLIREVKVITLKSKLVSDFRKDFQFYKVREINNYHHAHDAYLNAVVGTA
LIKKYPKLESEFVYGDYKVYDVRKMIAKSEQEIG   (SEQ ID NO: 10)

>CircularPermutant_11   ["CP11"]
       [new start-MKA; insert site-1032A]
MKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVA
KVEKGKSKKLKSVKELLGITIMERSSFEKNPIDFLEAKGYKEVKKDLIIKLPKYSLFEL
ENGRKRMLASAGELQKGNELALPSKYVNFLYLASHYEKLKGSPEDNEQKQLFVEQHKHY
LDEIIEQISEFSKRVILADANLDKVLSAYNKHRDKPIREQAENIIHLFTLTNLGAPAAF
KYFDTTIDRKRYTSTKEVLDATLIHQSITGLYETRIDLSQLGGD**XXXXXXXXXXXXXX
XXXX**MDKKYSIGLAIGTNSVGWAVITDEYKVPSKKFKVLGNTDRHSIKKNLIGALLFD
SGETAEATRLKRTARRRYTRRKNRICYLQEIFSNEMAKVDDSFFHRLEESFLVEEDKKH
ERHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLF
LAAKNLSDAILLSDILRVNTEITKAPLSASMIKRYDEHHQDLTLLKALVRQQLPEKYKE
IFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTR
KSEETITPWNFEEVVDKGASAQSFIERMTNFDKNLPNEKVLPKHSLLYEYFTVYNELTK

Figure 1 (Cont. 7)

VKYVTEGMRKPAFLSGEQKKAIVDLLFKTNRKVTVKQLKEDYFKKIECFDSVEISGVED
RFNASLGTYHDLLKIIKDKDFLDNEENEDILEDIVLTLTLFEDREMIEERLKTYAHLFD
DKVMKQLKRRRYTGWGRLSRKLINGIRDKQSGKTILDFLKSDGFANRNFMQLIHDDSLT
FKEDIQKAQVSGQGDSLHEHIANLAGSPAIKKGILQTVKVVDELVKVMGRHKPENIVIE
MARENQTTQKGQKNSRERMKRIEEGIKELGSQILKEHPVENTQLQNEKLYLYYLQNGRD
MYVDQELDINRLSDYDVDAIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRM
NTKYDENDKLIREVKVITLKSKLVSDFRKDFQFYKVREINNYHHAHDAYLNAVVGTALI
KKYPKLESEFVYGDYKVYDVRKMIAKSEQEIGKA     (SEQ ID NO: 11)

\>CircularPermutant_12   ["CP12"]
 [new start-MNI; insert site-1042I]
MNIMNFFKTEITLANGEIRKRPLIETNGETGEIVWDKGRDFATVRKVLSMPQVNIVKKT
EVQTGGFSKESILPKRNSDKLIARKKDWDPKKYGGFDSPTVAYSVLVVAKVEKGKSKKL
KSVKELLGITIMERSSFEKNPIDFLEAKGYKEVKKDLIIKLPKYSLFELENGRKRMLAS
AGELQKGNELALPSKYVNFLYLASHYEKLKGSPEDNEQKQLFVEQHKHYLDEIIEQISE
FSKRVILADANLDKVLSAYNKHRDKPIREQAENIIHLFTLTNLGAPAAFKYFDTTIDRK
RYTSTKEVLDATLIHQSITGLYETRIDLSQLGGDXXXXXXXXXXXXXXXXXXXXXMDKKY
SIGLAIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIV
DEVAYHEKYPTIYHLRKKLVDSTDKADLRLIYLALAHMIKFRGHFLIEGDLNPDNSDVD
KLFIQLVQTYNQLFEENPINASGVDAKAILSARLSKSRRLENLIAQLPGEKKNGLFGNL
IALSLGLTPNFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEIFFDQSKNGY
AGYIDGGASQEEFYKFIKPILEKMDGTEELLVKLNREDLLRKQRTFDNGSIPHQIHLGE
LHAILRRQEDFYPFLKDNREKIEKILTFRIPYYVGPLARGNSRFAWMTRKSEETITPWN
FEEVVDKGASAQSFIERMTNFDKNLPNEKVLPKHSLLYEYFTVYNELTKVKYVTEGMRK
PAFLSGEQKKAIVDLLFKTNRKVTVKQLKEDYFKKIECFDSVEISGVEDRFNASLGTYH
DLLKIIKDKDFLDNEENEDILEDIVLTLTLFEDREMIEERLKTYAHLFDDKVMKQLKRR
RYTGWGRLSRKLINGIRDKQSGKTILDFLKSDGFANRNFMQLIHDDSLTFKEDIQKAQV
SGQGDSLHEHIANLAGSPAIKKGILQTVKVVDELVKVMGRHKPENIVIEMARENQTTQK
GQKNSRERMKRIEEGIKELGSQILKEHPVENTQLQNEKLYLYYLQNGRDMYVDQELDIN
RLSDYDVDAIVPQSFLKDDSIDNKVLTRSDKNRGKSDNVPSEEVVKKMKNYWRQLLNAK
LITQRKFDNLTKAERGGLSELDKAGFIKRQLVETRQITKHVAQILDSRMNTKYDENDKL
IREVKVITLKSKLVSDFRKDFQFYKVREINNYHHAHDAYLNAVVGTALIKKYPKLESEF
VYGDYKVYDVRKMIAKSEQEIGKATAKYFFYSNI     (SEQ ID NO: 12)

Figure 1 (Cont. 8)

\>CircularPermutant_13 ["CP13"]
    [new start-M; insert site-1245L]
MKGSPEDNEQKQLFVEQHKHYLDEIIEQISEFSKRVILADANLDKVLSAYNKHRDKPIR
EQAENIIHLFTLTNLGAPAAFKYFDTTIDRKRYTSTKEVLDATLIHQSITGLYETRIDL
SQLGGDXXXXXXXXXXXXXXXXXXXXXMDKKYSIGLAIGTNSVGWAVITDEYKVPSKKFK
VLGNTDRHSIKKNLIGALLFDSGETAEATRLKRTARRRYTRRKNRICYLQEIFSNEMAK
VDDSFFHRLEESFLVEEDKKHERHPIFGNIVDEVAYHEKYPTIYHLRKKLVDSTDKADL
RLIYLALAHMIKFRGHFLIEGDLNPDNSDVDKLFIQLVQTYNQLFEENPINASGVDAKA
ILSARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDEH
HQDLTLLKALVRQQLPEKYKEIFFDQSKNGYAGYIDGGASQEEFYKFIKPILEKMDGTE
ELLVKLNREDLLRKQRTFDNGSIPHQIHLGELHAILRRQEDFYPFLKDNREKIEKILTF
RIPYYVGPLARGNSRFAWMTRKSEETITPWNFEEVVDKGASAQSFIERMTNFDKNLPNE
KVLPKHSLLYEYFTVYNELTKVKYVTEGMRKPAFLSGEQKKAIVDLLFKTNRKVTVKQL
KEDYFKKIECFDSVEISGVEDRFNASLGTYHDLLKIIKDKDFLDNEENEDILEDIVLTL
TLFEDREMIEERLKTYAHLFDDKVMKQLKRRRYTGWGRLSRKLINGIRDKQSGKTILDF
LKSDGFANRNFMQLIHDDSLTFKEDIQKAQVSGQGDSLHEHIANLAGSPAIKKGILQTV
KVVDELVKVMGRHKPENIVIEMARENQTTQKGQKNSRERMKRIEEGIKELGSQILKEHP
VENTQLQNEKLYLYYLQNGRDMYVDQELDINRLSDYDVDAIVPQSFLKDDSIDNKVLTR
SDKNRGKSDNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKDFQFYKVRE
INNYHHAHDAYLNAVVGTALIKKYPKLESEFVYGDYKVYDVRKMIAKSEQEIGKATAKY
FFYSNIMNFFKTEITLANGEIRKRPLIETNGETGEIVWDKGRDFATVRKVLSMPQVNIV
KKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRM
LASAGELQKGNELALPSKYVNFLYLASHYEKL   (SEQ ID NO: 13)

\>CircularPermutant_14 ["CP14"]
    [new start-MSSP; insert site-1249P]
MSSPEDNEQKQLFVEQHKHYLDEIIEQISEFSKRVILADANLDKVLSAYNKHRDKPIRE
QAENIIHLFTLTNLGAPAAFKYFDTTIDRKRYTSTKEVLDATLIHQSITGLYETRIDLS
QLGGDXXXXXXXXXXXXXXXXXXXXXMDKKYSIGLAIGTNSVGWAVITDEYKVPSKKFKV
LGNTDRHSIKKNLIGALLFDSGETAEATRLKRTARRRYTRRKNRICYLQEIFSNEMAKV
DDSFFHRLEESFLVEEDKKHERHPIFGNIVDEVAYHEKYPTIYHLRKKLVDSTDKADLR
LIYLALAHMIKFRGHFLIEGDLNPDNSDVDKLFIQLVQTYNQLFEENPINASGVDAKAI
LSARLSKSRRLENLIAQLPGEKKNGLFGNLIALSLGLTPNFKSNFDLAEDAKLQLSKDT
YDDDLDNLLAQIGDQYADLFLAAKNLSDAILLSDILRVNTEITKAPLSASMIKRYDEHH
QDLTLLKALVRQQLPEKYKEIFFDQSKNGYAGYIDGGASQEEFYKFIKPILEKMDGTEE
LLVKLNREDLLRKQRTFDNGSIPHQIHLGELHAILRRQEDFYPFLKDNREKIEKILTFR
IPYYVGPLARGNSRFAWMTRKSEETITPWNFEEVVDKGASAQSFIERMTNFDKNLPNEK
VLPKHSLLYEYFTVYNELTKVKYVTEGMRKPAFLSGEQKKAIVDLLFKTNRKVTVKQLK
EDYFKKIECFDSVEISGVEDRFNASLGTYHDLLKIIKDKDFLDNEENEDILEDIVLTLT
LFEDREMIEERLKTYAHLFDDKVMKQLKRRRYTGWGRLSRKLINGIRDKQSGKTILDFL
KSDGFANRNFMQLIHDDSLTFKEDIQKAQVSGQGDSLHEHIANLAGSPAIKKGILQTVK

Figure 1 (Cont. 9)

```
VVDELVKVMGRHKPENIVIEMARENQTTQKGQKNSRERMKRIEEGIKELGSQILKEHPV
ENTQLQNEKLYLYYLQNGRDMYVDQELDINRLSDYDVDAIVPQSFLKDDSIDNKVLTRS
DKNRGKSDNVPSEEVVKKMKNYWRQLLNAKLITQRKFDNLTKAERGGLSELDKAGFIKR
QLVETRQITKHVAQILDSRMNTKYDENDKLIREVKVITLKSKLVSDFRKDFQFYKVREI
NNYHHAHDAYLNAVVGTALIKKYPKLESEFVYGDYKVYDVRKMIAKSEQEIGKATAKYF
FYSNIMNFFKTEITLANGEIRKRPLIETNGETGEIVWDKGRDFATVRKVLSMPQVNIVK
KTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRML
ASAGELQKGNELALPSKYVNFLYLASHYEKLKGSP   (SEQ ID NO: 14)

>CircularPermutant_15   ["CP15"]
     [new start-MTE; insert site-1250E]
MTEDNEQKQLFVEQHKHYLDEIIEQISEFSKRVILADANLDKVLSAYNKHRDKPIREQA
ENIIHLFTLTNLGAPAAFKYFDTTIDRKRYTSTKEVLDATLIHQSITGLYETRIDLSQL
GGDXXXXXXXXXXXXXXXXXXXXXMDKKYSIGLAIGTNSVGWAVITDEYKVPSKKFKVLG
NTDRHSIKKNLIGALLFDSGETAEATRLKRTARRRYTRRKNRICYLQEIFSNEMAKVDD
SFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILS
ARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQD
LTLLKALVRQQLPEKYKEIFFDQSKNGYAGYIDGGASQEEFYKFIKPILEKMDGTEELL
VKLNREDLLRKQRTFDNGSIPHQIHLGELHAILRRQEDFYPFLKDNREKIEKILTFRIP
YYVGPLARGNSRFAWMTRKSEETITPWNFEEVVDKGASAQSFIERMTNFDKNLPNEKVL
PKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLF
EDREMIEERLKTYAHLFDDKVMKQLKRRRYTGWGRLSRKLINGIRDKQSGKTILDFLKS
DGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVEN
TQLQNEKLYLYYLQNGRDMYVDQELDINRLSDYDVDAIVPQSFLKDDSIDNKVLTRSDK
NRGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINN
YHHAHDAYLNAVVGTALIKKYPKLESEFVYGDYKVYDVRKMIAKSEQEIGKATAKYFFY
SNIMNFFKTEITLANGEIRKRPLIETNGETGEIVWDKGRDFATVRKVLSMPQVNIVKKT
EVQTGGFSKESILPKRNSDKLIARKKDWDPKKYGGFDSPTVAYSVLVVAKVEKGKSKKL
KSVKELLGITIMERSSFEKNPIDFLEAKGYKEVKKDLIIKLPKYSLFELENGRKRMLAS
AGELQKGNELALPSKYVNFLYLASHYEKLKGSPE  (SEQ ID NO: 15)
```

Figure 1 (Cont. 10)

```
>CircularPermutant_16 ["CP16"]
     [new start-MIA; insert site-1283A]
MIADANLDKVLSAYNKHRDKPIREQAENIIHLFTLTNLGAPAAFKYFDTTIDRKRYTST
KEVLDATLIHQSITGLYETRIDLSQLGGDXXXXXXXXXXXXXXXXXXXXXXMDKKYSIGLA
IGTNSVGWAVITDEYKVPSKKFKVLGNTDRHSIKKNLIGALLFDSGETAEATRLKRTAR
RRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQ
LVQTYNQLFEENPINASGVDAKAILSARLSKSRRLENLIAQLPGEKKNGLFGNLIALSL
GLTPNFKSNFDLAEDAKLQLSKDTYDDDLDNLLAQIGDQYADLFLAAKNLSDAILLSDI
LRVNTEITKAPLSASMIKRYDEHHQDLTLLKALVRQQLPEKYKEIFFDQSKNGYAGYID
GGASQEEFYKFIKPILEKMDGTEELLVKLNREDLLRKQRTFDNGSIPHQIHLGELHAIL
RRQEDFYPFLKDNREKIEKILTFRIPYYVGPLARGNSRFAWMTRKSEETITPWNFEEVV
DKGASAQSFIERMTNFDKNLPNEKVLPKHSLLYEYFTVYNELTKVKYVTEGMRKPAFLS
GEQKKAIVDLLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQLKRRRYTGW
GRLSRKLINGIRDKQSGKTILDFLKSDGFANRNFMQLIHDDSLTFKEDIQKAQVSGQGD
SLHEHIANLAGSPAIKKGILQTVKVVDELVKVMGRHKPENIVIEMARENQTTQKGQKNS
RERMKRIEEGIKELGSQILKEHPVENTQLQNEKLYLYYLQNGRDMYVDQELDINRLSDY
DVDAIVPQSFLKDDSIDNKVLTRSDKNRGKSDNVPSEEVVKKMKNYWRQLLNAKLITQR
KFDNLTKAERGGLSELDKAGFIKRQLVETRQITKHVAQILDSRMNTKYDENDKLIREVK
VITLKSKLVSDFRKDFQFYKVREINNYHHAHDAYLNAVVGTALIKKYPKLESEFVYGDY
KVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKEV
KKDLIIKLPKYSLFELENGRKRMLASAGELQKGNELALPSKYVNFLYLASHYEKLKGSP
EDNEQKQLFVEQHKHYLDEIIEQISEFSKRVILA        (SEQ ID NO: 16)

>S. pyogenes Cas9(dCas9: D10A/H840A - bold and underline)
MDKKYSIGLAIGTNSVGWAVITDEYKVPSKKFKVLGNTDRHSIKKNLIGALLFDSGETA
EATRLKRTARRRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGHFLIEGDLNPD
NSDVDKLFIQLVQTYNQLFEENPINASGVDAKAILSARLSKSRRLENLIAQLPGEKKNG
LFGNLIALSLGLTPNFKSNFDLAEDAKLQLSKDTYDDDLDNLLAQIGDQYADLFLAAKN
LSDAILLSDILRVNTEITKAPLSASMIKRYDEHHQDLTLLKALVRQQLPEKYKEIFFDQ
SKNGYAGYIDGGASQEEFYKFIKPILEKMDGTEELLVKLNREDLLRKQRTFDNGSIPHQ
IHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVT
EGMRKPAFLSGEQKKAIVDLLFKTNRKVTVKQLKEDYFKKIECFDSVEISGVEDRFNAS
LGTYHDLLKIIKDKDFLDNEENEDILEDIVLTLTLFEDREMIEERLKTYAHLFDDKVMK
QLKRRRYTGWGRLSRKLINGIRDKQSGKTILDFLKSDGFANRNFMQLIHDDSLTFKEDI
QKAQVSGQGDSLHEHIANLAGSPAIKKGILQTVKVVDELVKVMGRHKPENIVIEMAREN
QTTQKGQKNSRERMKRIEEGIKELGSQILKEHPVENTQLQNEKLYLYYLQNGRDMYVDQ
ELDINRLSDYDVDAIVPQSFLKDDSIDNKVLTRSDKNRGKSDNVPSEEVVKKMKNYWRQ
LLNAKLITQRKFDNLTKAERGGLSELDKAGFIKRQLVETRQITKHVAQILDSRMNTKYD
```

Figure 1 (Cont. 11)

```
ENDKLIREVKVITLKSKLVSDFRKDFQFYKVREINNYHHAHDAYLNAVVGTALIKKYPK
LESEFVYGDYKVYDVRKMIAKSEQEIGKATAKYFFYSNIMNFFKTEITLANGEIRKRPL
IETNGETGEIVWDKGRDFATVRKVLSMPQVNIVKKTEVQTGGFSKESILPKRNSDKLIA
RKKDWDPKKYGGFDSPTVAYSVLVVAKVEKGKSKKLKSVKELLGITIMERSSFEKNPID
FLEAKGYKEVKKDLIIKLPKYSLFELENGRKRMLASAGELQKGNELALPSKYVNFLYLA
SHYEKLKGSPEDNEQKQLFVEQHKHYLDEIIEQISEFSKRVILADANLDKVLSAYNKHR
DKPIREQAENIIHLFTLTNLGAPAAFKYFDTTIDRKRYTSTKEVLDATLIHQSITGLYE
TRIDLSQLGGD    (SEQ ID NO: 17)
```

Figure 2

A
Circular permutation overview

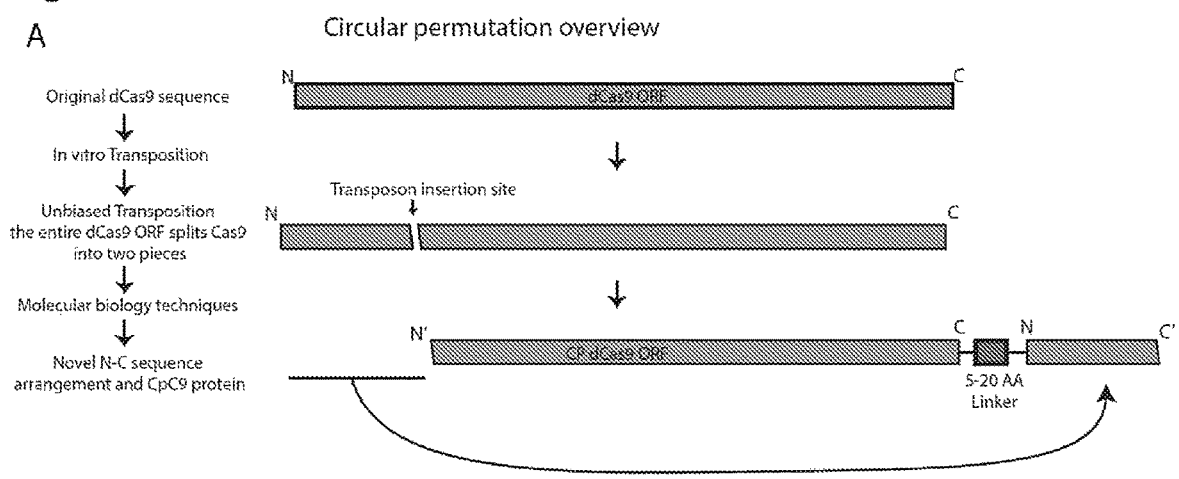

Original dCas9 sequence
↓
In vitro Transposition
↓
Unbiased Transposition the entire dCas9 ORF splits Cas9 into two pieces
↓
Molecular biology techniques
↓
Novel N-C sequence arrangement and CpC9 protein

B
CpC9 Library build technique

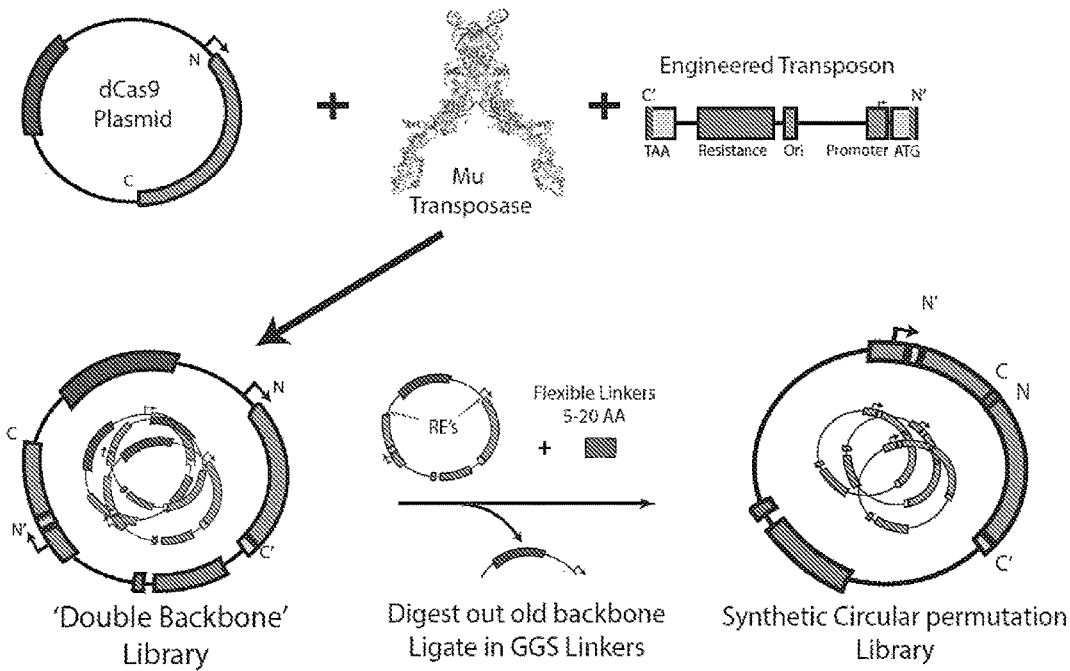

'Double Backbone' Library

Digest out old backbone Ligate in GGS Linkers

Synthetic Circular permutation Library

Figure 2
CpC9 Library PCR Validation
C
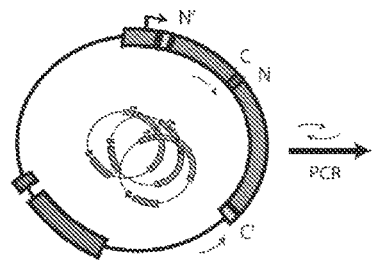 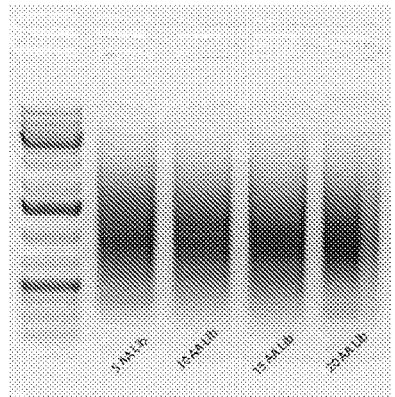
Bands range from
~400bp to 5kb
indicating full
coverage
for Cp-Cas9
D
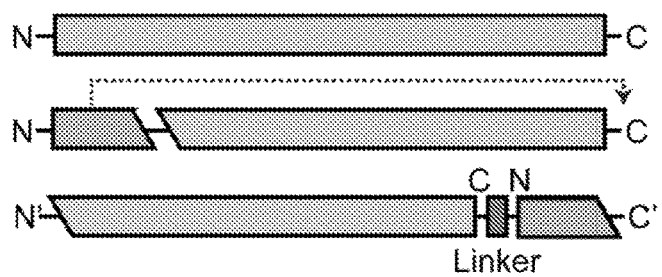
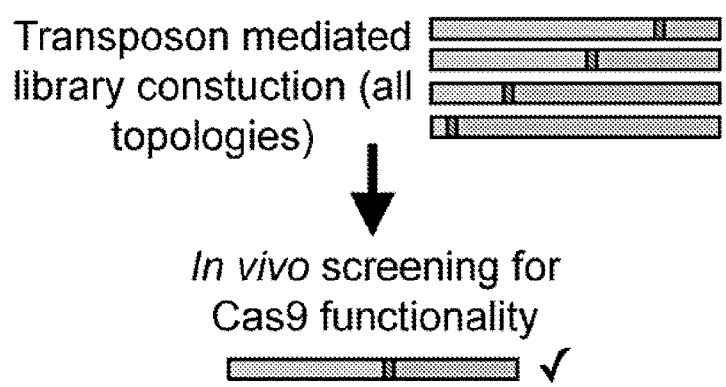
Transposon mediated library constuction (all topologies)
*In vivo* screening for Cas9 functionality

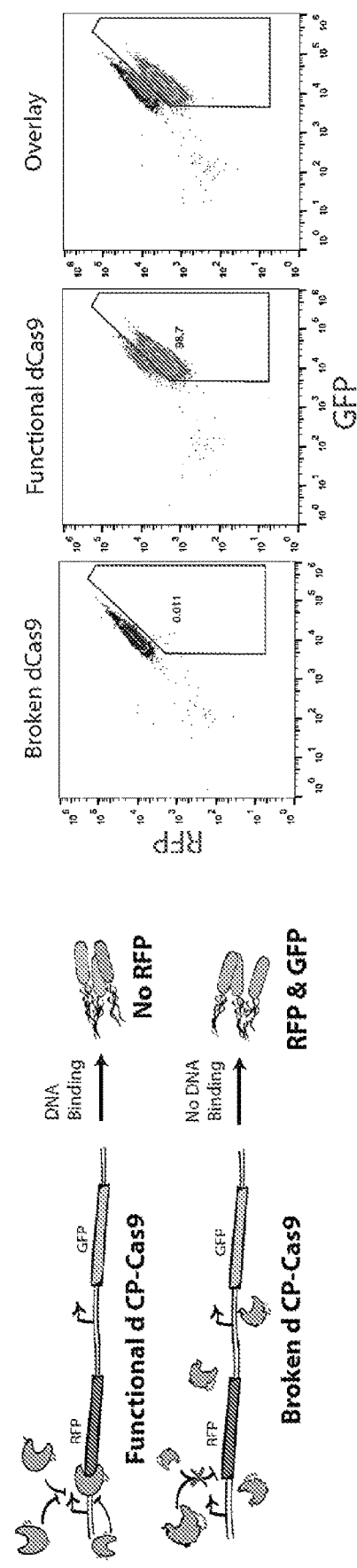

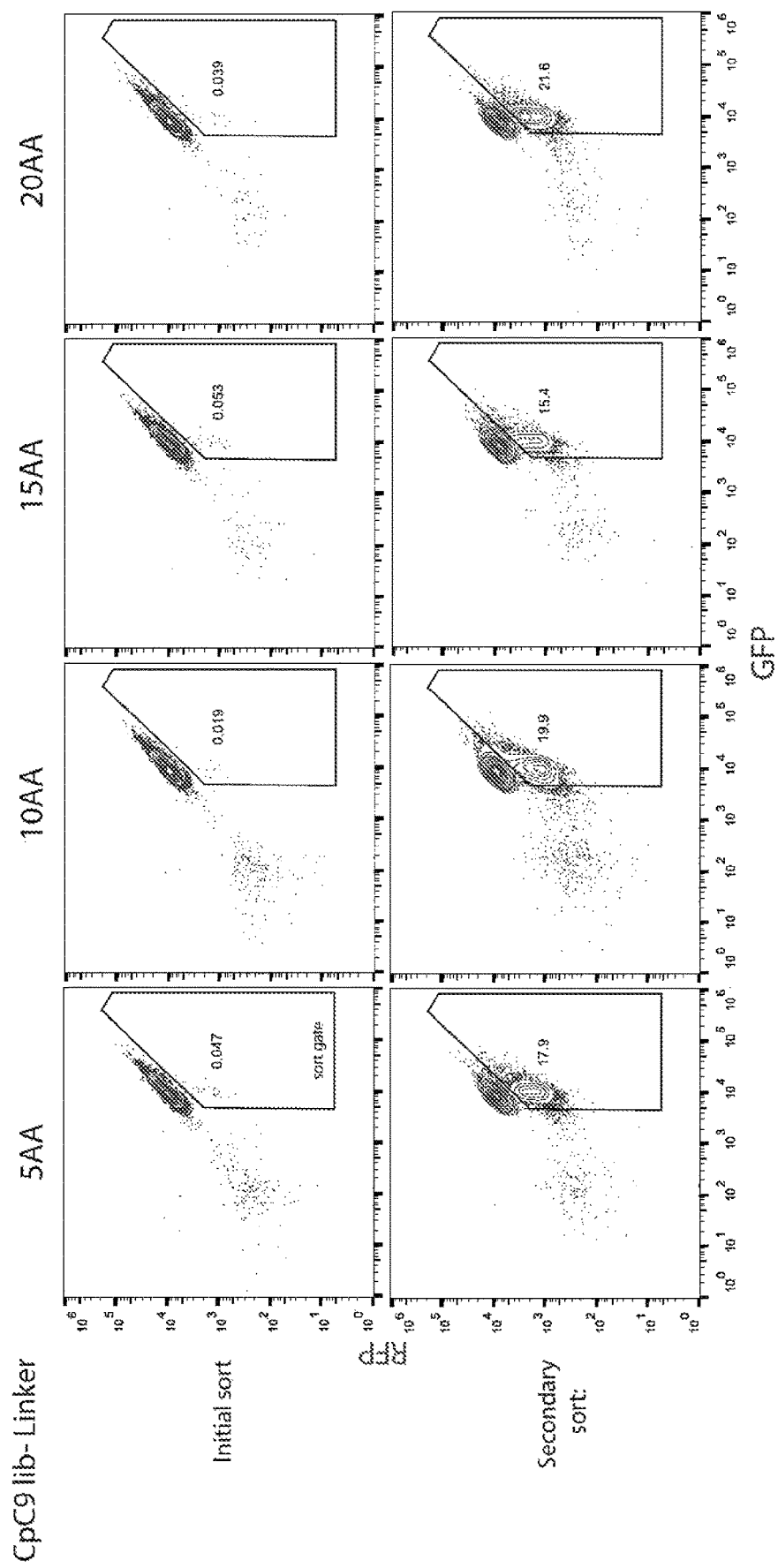

**Figure 3
B (Cont.)**
Post-sort outgrowth plate images
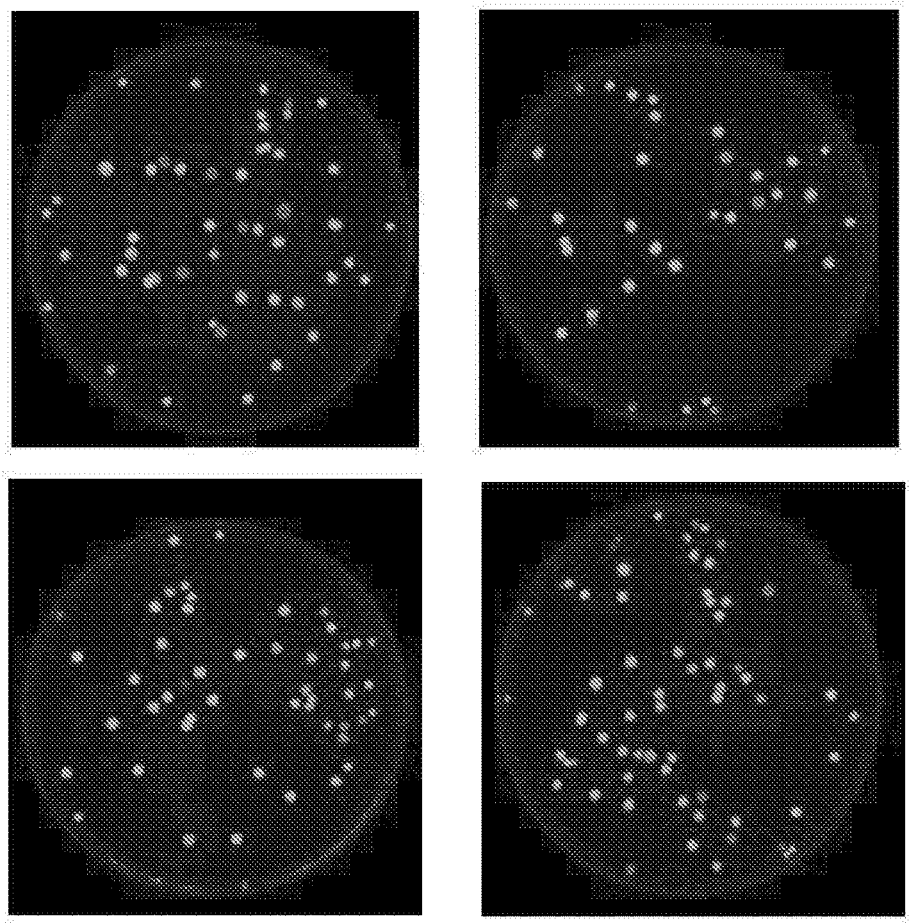
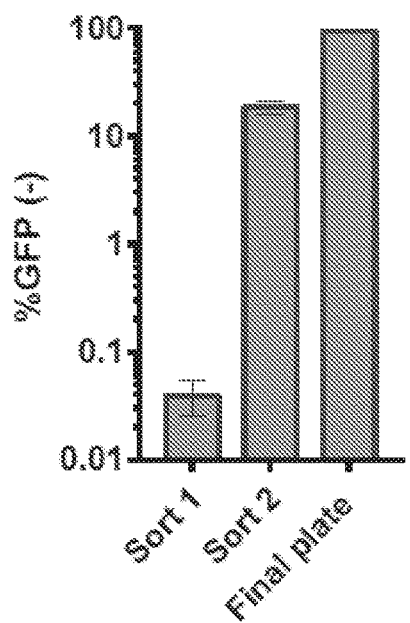

Figure 3 C
Lib and Sort PCR Analysis
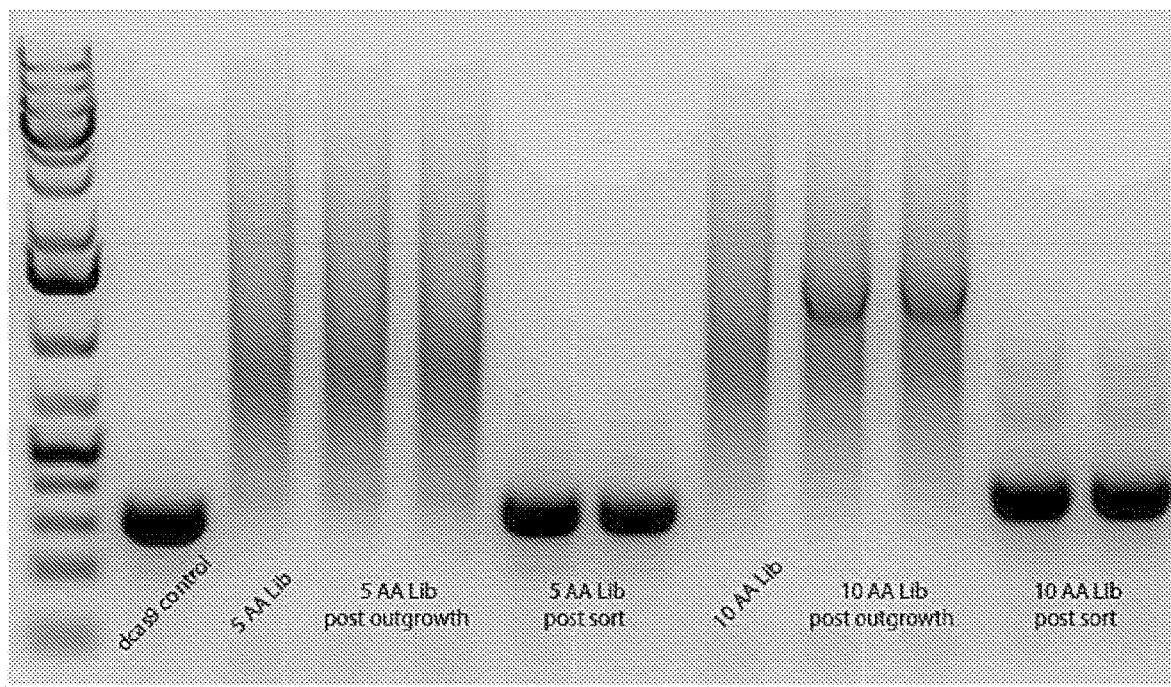
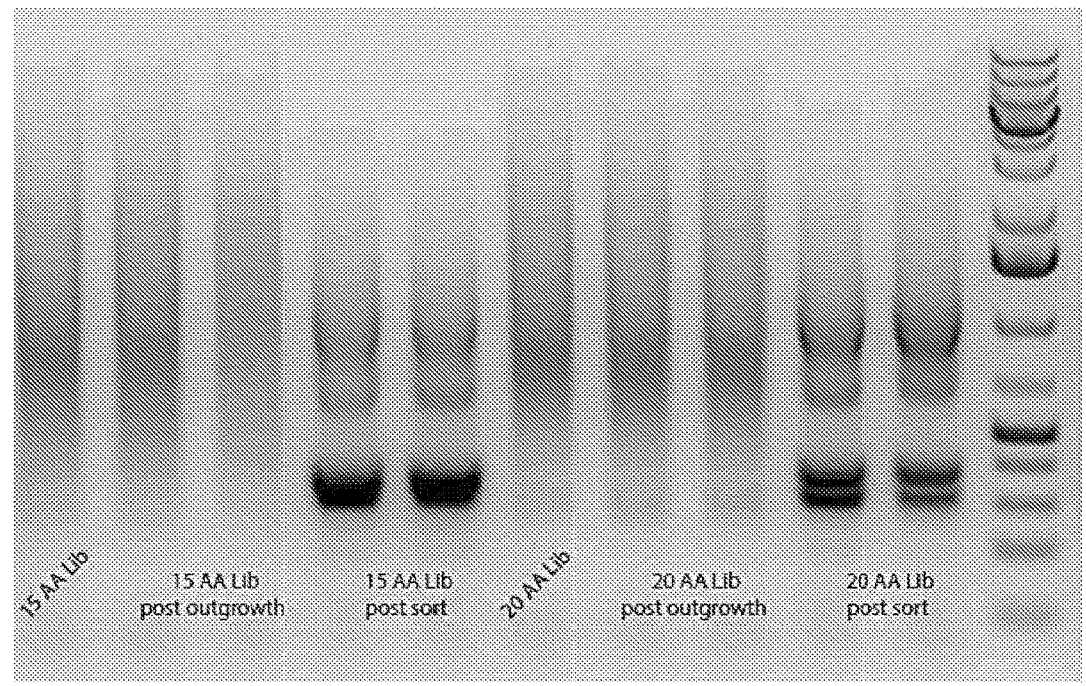

D (Cont.)

Figure 10
A
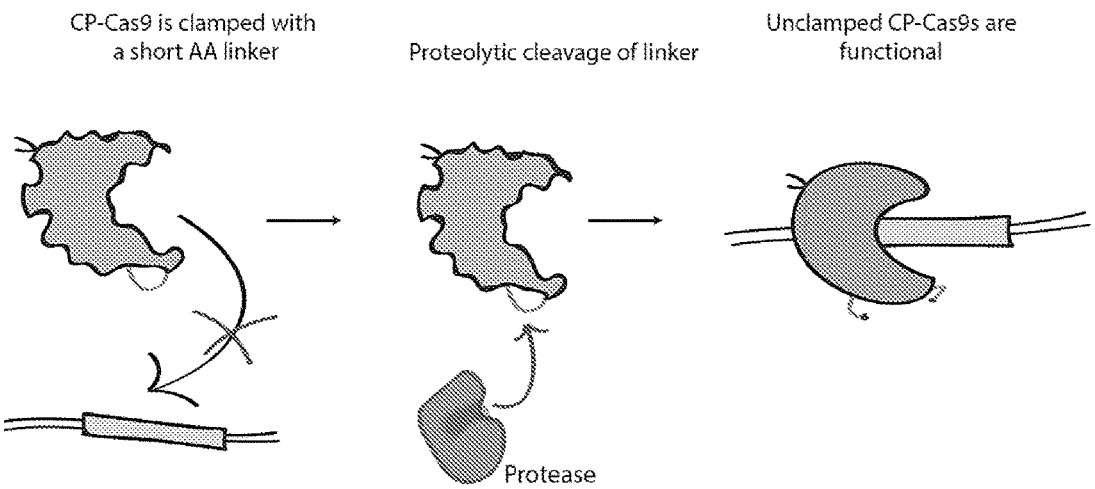
CP-Cas9 is clamped with a short AA linker → Proteolytic cleavage of linker → Unclamped CP-Cas9s are functional
B
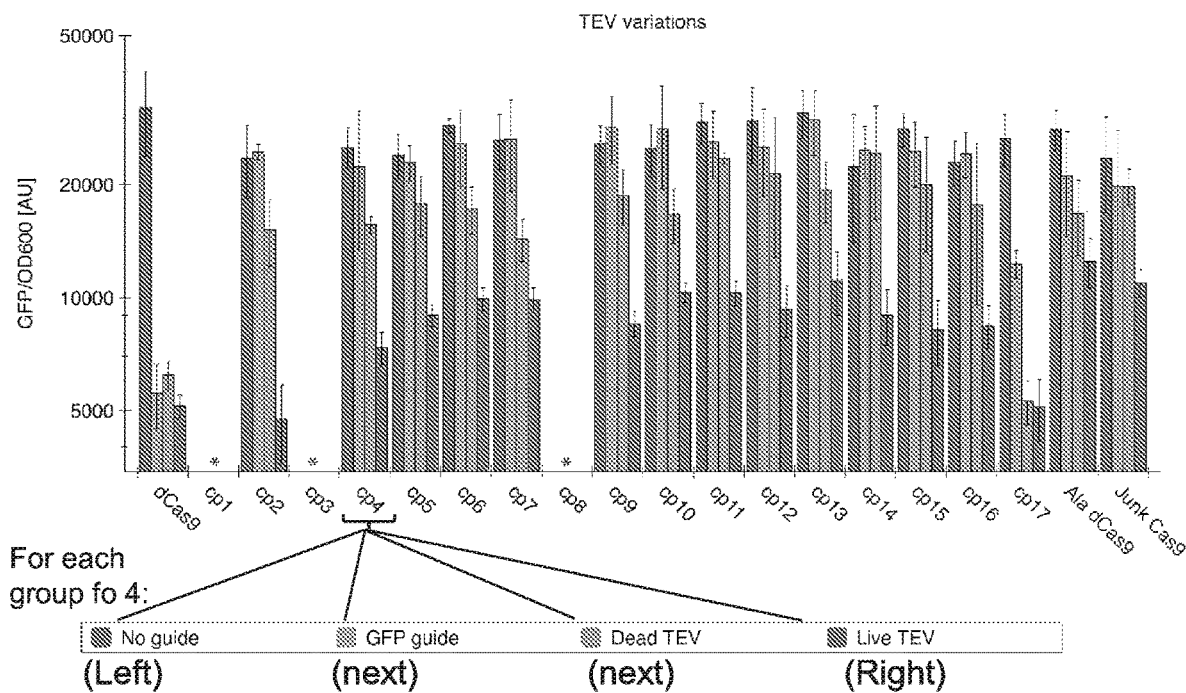
'Caged' Cp-Cas9 gfp repression data
For each group fo 4:
- No guide (Left)
- GFP guide (next)
- Dead TEV (next)
- Live TEV (Right)

Figure 16 (Cont.)
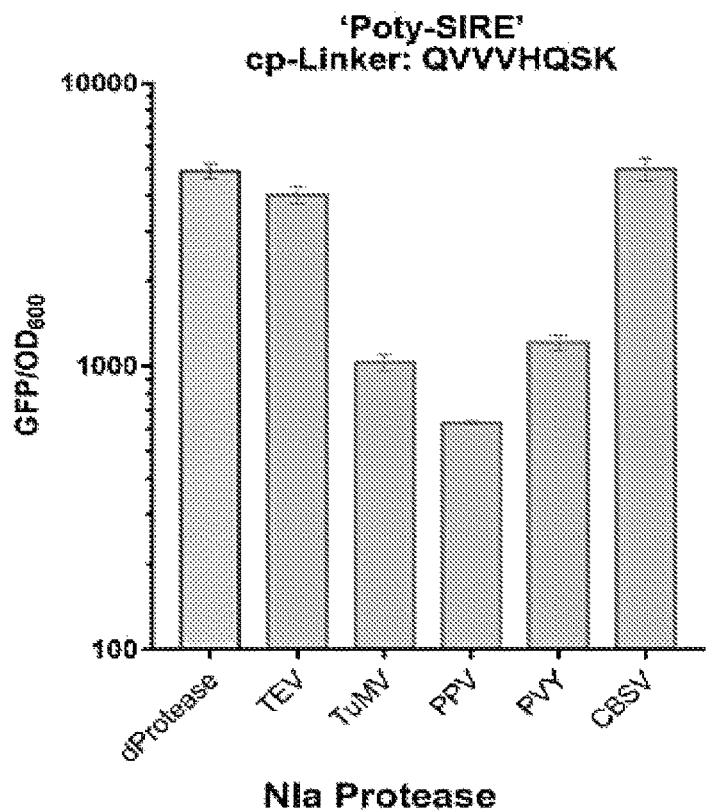
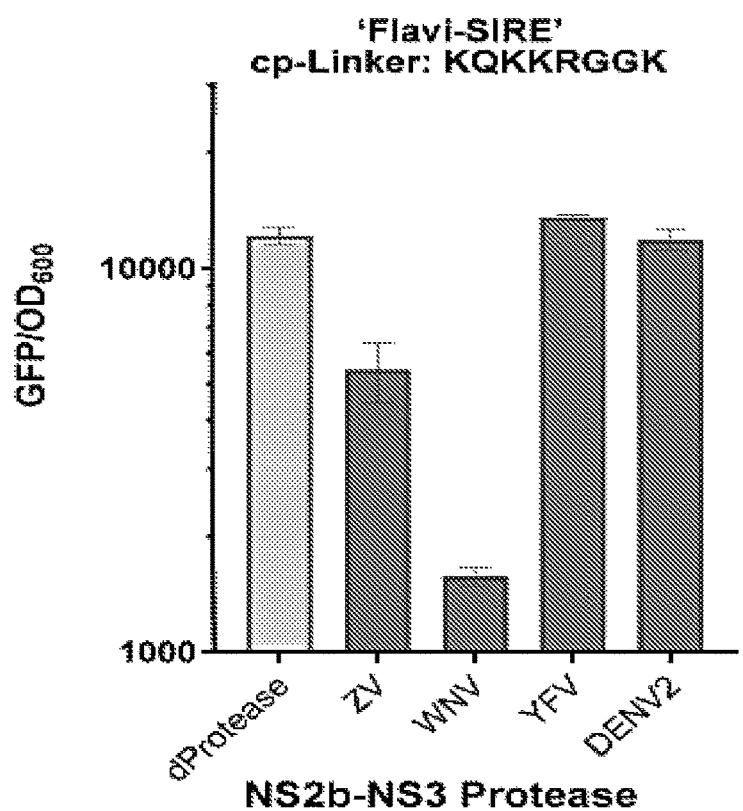

Figure 19 (Cont.)

left to right: (i) dProtease, (ii) TuMV Pro, (iii) PPV pro, (iv) PVY pro, (v) ZV pro, (vi) WNV pro

VARIANT RNA-GUIDED POLYPEPTIDES AND METHODS OF USE

CROSS-REFERENCE

This application claims the benefit of U.S. Provisional Patent Application No. 62/421,146, filed Nov. 11, 2016, which application is incorporated herein by reference in its entirety.

STATEMENT REGARDING FEDERALLY SPONSORED RESEARCH

This invention was made with government support under Grant No. EB018658 awarded by The National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-340WO_Seq List_ST25.txt" created on Nov. 8, 2017 and having a size of 7,844 KB. The contents of the text file are incorporated by reference herein in their entirety.

INTRODUCTION

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In Type II CRISPR-Cas systems, the Cas9 protein functions as an RNA-guided endonuclease that uses a dual-guide RNA consisting of crRNA and trans-activating crRNA (tracrRNA) for target recognition and cleavage by a mechanism involving two nuclease active sites that together generate double-stranded DNA breaks (DSBs).

RNA-programmed Cas9 has proven to be a versatile tool for genome engineering in multiple cell types and organisms. Guided by a dual-RNA complex or a chimeric single-guide RNA, Cas9 (or variants of Cas9 such as nickase variants) can generate site-specific DSBs or single-stranded breaks (SSBs) within target nucleic acids. Target nucleic acids can include double-stranded DNA (dsDNA) and single-stranded DNA (ssDNA) as well as RNA. When cleavage of a DNA occurs within a cell (e.g., genomic DNA in a eukaryotic cell), the cell an repair the break in the target DNA by non-homologous end joining (NHEJ) or homology directed repair (HDR).

Thus, CRISPR/Cas systems provide a facile means of modifying genomic information. In addition, catalytically inactive Cas9 (dCas9) alone or fused to heterologous proteins such as transcriptional activator or repressor domains can be used to alter transcription levels at sites within target nucleic acids by binding to the target site without cleavage.

There is a need for variants of RNA-guide polypeptides (e.g., variant Cas9 proteins) that provide for, for example, conditionally active proteins and/or more efficient fusion proteins.

SUMMARY

Because the N- and C-termini of wild type Cas9 proteins are locked in a small, defined region of the protein, the effectiveness of many Cas9 protein fusions (which usually include a heterologous protein fused to the N- and/or C-terminus of a Cas9 protein) is less than optimal, and this is likely due to steric incompatibility. The inventors have generated circularly permutated Cas9 proteins (cpCas9 proteins) with entirely new N- and C-termini at defined sites around the Cas9 protein structure. cpCas9 proteins increase the effectiveness of Cas9 fusion proteins because they reduce the constraints imposed by the naturally existing N- and C-termini. The present disclosure provides RNA-guided polypeptides (e.g., circular permuted Cas9 proteins) in which the N-terminal end of an N-terminal fragment of a parent RNA-guided polypeptide (e.g., a parent Cas9 protein) is fused (e.g., via linker) to the C-terminus of the C-terminal fragment (thereby generating new N- and C-termini), as well as methods that employ such polypeptides.

In some cases, a subject RNA-guided polypeptide (e.g., a circular permuted Cas9 protein) is fused (e.g., at its new N- and/or C-terminus) to a fusion partner. This can provide for, for example, increased target nucleic acid editing accuracy. For example, when a non-permuted Cas9 protein is fused to a base editing cytidine deaminase, the protein can in some cases produce C to T editing within a 12 bp target window, and can include significant amounts (e.g., 2-3%), of undesirable deamination up to 15 bp outside of the intended target sequence. However, fusing the same base editing cytidine deaminase to the new N- or C-terminus of a circular permuted Cas9 protein (as disclosed herein) (e.g., using a linker of choice) the accuracy of target modification can be increased, e.g., in some cases with single nucleotide resolution. This can be accomplished, e.g., by fusing a desired domain (e.g., a deaminase domain) to a circular permuted Cas9 protein of choice. Multiple different cpCas9 proteins are provided herein, each of which provides new N- and C-termini at unique positions within the structure of the Cas9 protein. Thus, depending on the fusion partner of choice, an appropriate cpCas9 can be selected that will place the fused partner at a desired position (e.g., relative to the RuvC and/or HNH domains, relative to the target nucleic acid, relative to the guide RNA, and the like). This ability to position a fusion partner relative to the structure of the protein while allowing fusion to an N- and/or C-terminus, provides RNA-guided polypeptides that are better suited to avoid off-target effects.

The inventors have also discovered that the length of linkers used to fuse an N-terminal fragment of a Cas9 protein to the C-terminal fragment affects protein function. Specifically, short linkers constrain the protein such that it loses function. This property can be taken advantage of by using cleavable linkers. When cleavable short linkers are used, a conditionally active ('caged') RNA-guided polypeptide can be generated. The polypeptide's activity increases dramatically (e.g., can change from inactive to active) after cleavage of the cleavable linker. The present disclosure provides conditionally active RNA-guided polypeptides (e.g., conditionally active circular permuted Cas9 proteins), as well as methods that employ such polypeptides. For example, such polypeptides can be used to sense and respond to cellular inputs (e.g., presence of a protease such as a viral protease), causing a cellular output (e.g., cell death, e.g., by targeting an essential gene for reduced expression and/or targeting a gene for lethal overexpression).

The sites that can tolerate a 'break' within the Cas9 protein in order to generate a circular permuted Cas9 protein can also be used as a location for an internal insertion site for a heterologous protein. Thus, the present disclosure provides Cas9 fusion polypeptides that include an internal insertion of a heterologous polypeptide, as well as methods that employ such polypeptides.

The present disclosure provides nucleic acids comprising nucleotide sequences encoding any of the above polypeptides, as well as cells comprising such polypeptides and/or nucleic acids that encode such polypeptides. The present disclosure provides methods of binding and/or modifying a target nucleic acid, involving use of any of the above polypeptides.

BRIEF DESCRIPTION OF THE DRAWINGS

FIG. 1 presents sequences of examples of subject RNA-guided polypeptides, in this case circular permutated Cas9 proteins (SEQ ID NOs: 1-16), and an example of a parent RNA-guided polypeptide (in this case a dCas9 *Streptococcus pyogenes* Cas9 protein (SEQ ID NO: 17)) used to generate the polypeptides set forth as SEQ ID NOs: 1-16.

FIG. 2 (panels A-D) presents details regarding how circular permutated Cas9 proteins were generated.

FIG. 10 (panels A-B) presents a schematic and data related to the use of a cleavable linker in a subject RNA-guided polypeptide, in this case a circular permuted Cas9 protein.

DEFINITIONS

Figure 3:
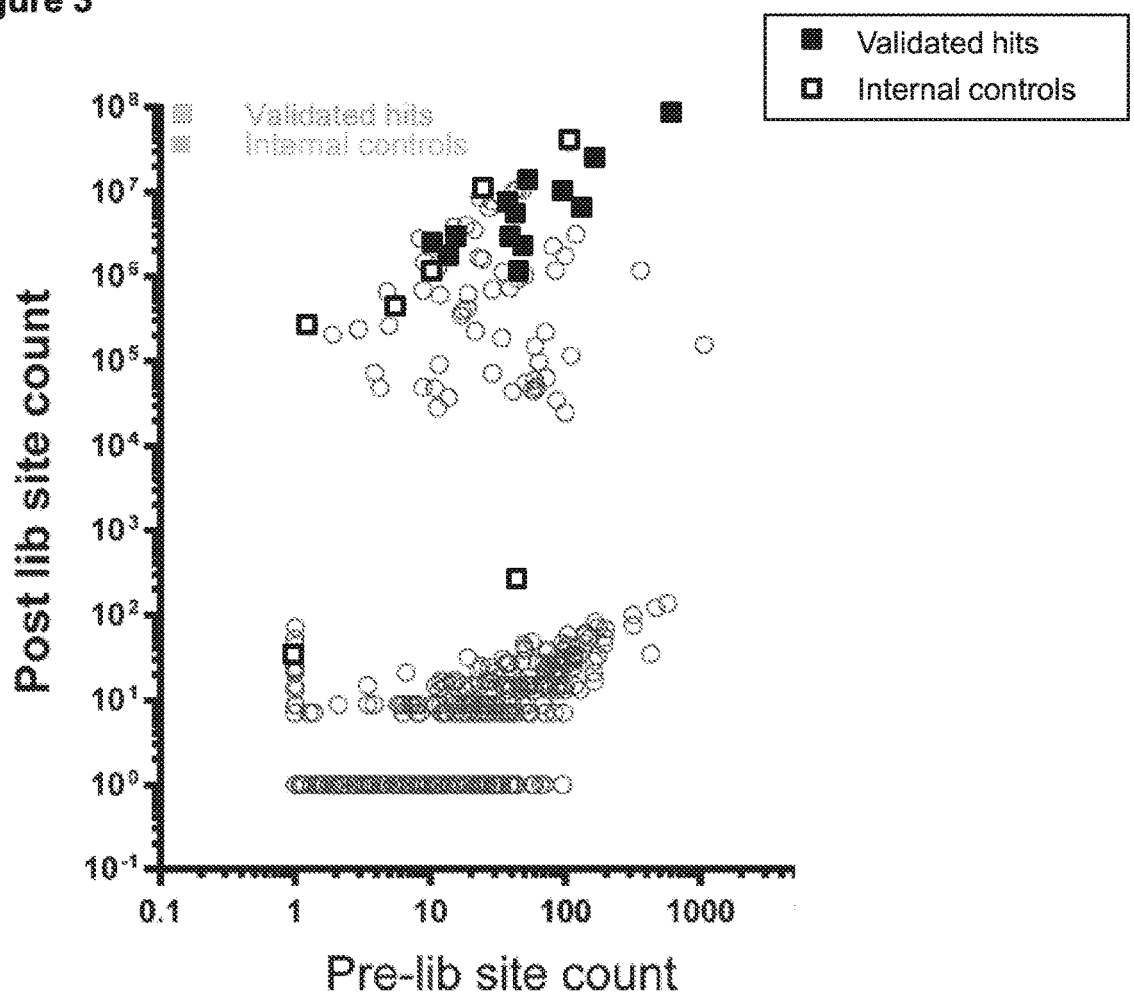
FIG. 3 (panels A-D) presents schematics and data related to a screen that was performed to identify circular permuted Cas9 proteins that retain RNA guided sequence specific target DNA binding activity.
Figure 3:
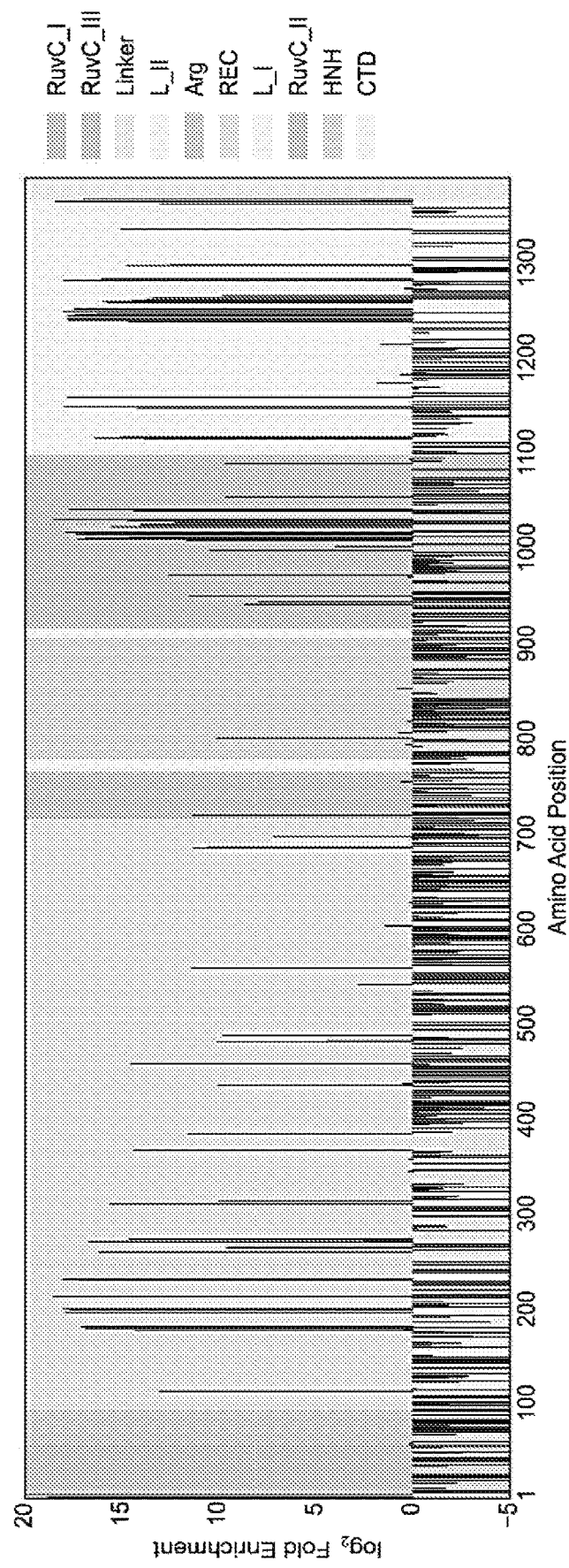

"Heterologous," as used herein, means a nucleotide or polypeptide sequence that is not found in the native nucleic acid or protein, respectively. For example, a polypeptide of the present disclosure (e.g., a circular permuted Cas9 protein) can be fused to a heterologous polypeptide (comprising an amino acid sequence from a protein other than the Cas9 polypeptide).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such can be done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding a subject variant Cas9 polypeptide, such as a circular permuted Cas9 protein), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a protein" includes a plurality of such proteins and reference to "the RNA" includes reference to one or more RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides (i) RNA-guided polypeptides (e.g., circular permuted Cas9 proteins) in which the amino terminal (N-terminal) end of an N-terminal fragment of a parent RNA-guided polypeptide (e.g., a parent Cas9 protein) is fused (e.g., via linker) to the carboxyl terminal (C-terminal) end of the C-terminal fragment (thereby generating new N- and C-termini), (ii) conditionally active RNA-guided polypeptides (e.g., conditionally active circular permuted Cas9 proteins), and (iiii) Cas9 fusion polypeptides that include an internal insertion of a heterologous polypeptide; as well as methods that employ the above polypeptides.

RNA-Guided Polypeptide Polypeptides

The present disclosure provides RNA-guided polypeptides. To generate a subject RNA-guided polypeptide, a protein coding sequence of a parent protein (a parent RNA-guided polypeptide) is rearranged so that an N-terminal fragment (portion) is removed and fused to a C-terminal fragment of the parent protein (the N-terminal end of the N-terminal fragment is fused to the C-terminal end of a C-terminal fragment) (e.g., in some cases the N-terminal fragment is fused to the remaining C-terminal fragment). A subject RNA-guided polypeptide is the resulting protein. Thus, in some cases, a subject RNA-guided polypeptide includes, in order from N-terminus to C-terminus: (a) a C-terminal fragment of a parent RNA-guided polypeptide; (b) a linker; and (c) an N-terminal fragment of the parent RNA-guided polypeptide (e.g., in some cases the remaining N-terminal fragment of the parent RNA-guided polypeptide). In some embodiments, the parent RNA-guided polypeptide includes, in order from N- to C-terminus: i) a first RuvC subdomain; ii) a second RuvC subdomain; iii) an HNH domain; and iv) a third RuvC subdomain.

In some cases, a subject RNA-guided polypeptide is referred to as a circular permutant of the parent protein (i.e., a "circular permuted protein"). In some cases, the parent protein is a Cas9 protein and the subject RNA-guided polypeptide can be referred to as a circular permuted Cas9 protein (i.e., a circular permutant of a Cas9 protein). The term "circular permutant" refers to a variant polypeptide (e.g., of a subject Cas9 protein) in which one section of the primary amino acid sequence has been moved to a different position within the primary amino acid sequence of the polypeptide, but where the local order of amino acids has not been changed, and where the three dimensional architecture of the protein is generally conserved. For example, a circular permutant of a wild type 500 amino acid polypeptide may have an N-terminal residue of number 50 (relative to the wild type protein), where residues 1-49 of the wild type protein are added to the C-terminus. Such a circular permutant, relative to the wild type protein sequence would have, from N-terminus to C-terminus, amino acid numbers 50-500 of the wild-type polypeptide followed by amino acids numbers 1-49 of the wild-type polypeptide (amino acid 49 would be the C-terminal residue). Thus, such an example circular permutant would have the same total number of amino acids as the wild type reference protein, and the amino acids would even be in the same order (locally), but the overall primary amino acid sequence is changed.

As used herein with reference to the terms "circular permuted Cas9 protein", or "circular permutant of a Cas9 protein", a circular permutation refers to a situation in which a protein coding sequence is rearranged so that an N-terminal fragment (portion) is removed, and then fused to the remaining C-terminal fragment. The term "circular permutant" can be used to describe the resulting protein. As used herein, a circular permutant can be associated with a number that defines the size (in amino acids) of the N-terminal fragment that is removed. A circular permutant of a Cas9 protein (i.e., a "circular permuted Cas9 protein") is in some cases referred to herein as a "cpCas9." Thus, for example, the term "cpCas9-182D" refers to a circular permuted Cas9 protein in which the first 182 amino acids (amino acid 182 in this particular example is 182D, e.g., see SEQ ID NO: 111) were removed from the N-terminus of a Cas9 protein, and were fused to the C-terminus. The resulting protein (the circular permuted Cas9 protein) therefore ends with former amino acid number 182, while the former C- and N-termini are internal within the primary sequence and are fused to one another (in some cases with a linker). In other words, as used herein, a given circular permuted Cas9 protein can be numbered according to last amino acid of the N-terminal fragment that is moved to become the new C-terminus (with the exception, of course, that one or more fusion partners can be fused to the new N- and/or C-termini, as discussed in more detail below).

FIG. 1 provides sequences for 16 different examples of subject RNA-guided polypeptides that are circular permuted Cas9 proteins (SEQ ID NOs: 1-16). In all 16 examples depicted, the starting Cas9 protein (the reference protein, the 'parent' RNA-guided polypeptide) was a dCas9 version of *S. pyogenes* Cas9 protein, set forth as SEQ ID NO: 111 (also shown in FIG. 1) (this protein includes D10A and H840A mutations relative to a wild type *S. pyogenes* Cas9 protein set forth as SEQ ID NO: 111, and therefore lacks a catalytically active RuvC domain and lacks a catalytically active HNH domain) The size of the N-terminal fragment that was removed (and then fused to the C-terminus) in the 16 different examples depicted in FIG. 1 was 182, 200, 231, 271, 311, 1011, 1017, 1024, 1029, 1030, 1032, 1042, 1245, 1249, 1250, and 1283 amino acids. In other words, the C-terminal amino acid of the N-terminal fragment that was removed (and then fused to the C-terminus) in the 16 different examples depicted in FIG. 1 was 182D, 200P, 231G, 271Y, 311E, 1011G, 1017D, 1024K, 1029I, 1030G, 1032A, 1042I, 1245L, 1249P, 1250E, and 1283A. Table 2 also provides amino acid positions for which functional circular permutants were experimentally identified (numbered using the same criteria as above).

TABLE 2

This table provides examples of amino acid positions for which functional circular permutants were experimentally identified. Amino acid positions are numbered according to the *S. pyogenes* Cas9 protein, set forth as SEQ ID NO: 111.

| Amino Acid Position | Log2 Fold Change |
|---|---|
| 1 | 16.56429 |
| 3 | 18.83088 |
| 5 | 19.92972 |
| 114 | 13.06206 |
| 178 | 14.34326 |
| 180 | 16.89046 |
| 182 | 17.10231 |
| 197 | 17.95169 |
| 200 | 17.72408 |
| 201 | 18.07842 |
| 214 | 18.54478 |
| 231 | 17.1985 |
| 232 | 18.07692 |
| 260 | 16.19355 |
| 265 | 9.577471 |
| 271 | 16.74354 |
| 274 | 14.62859 |
| 311 | 15.63764 |
| 314 | 9.984564 |
| 368 | 14.39728 |
| 385 | 11.61423 |
| 436 | 10.04488 |
| 459 | 14.53978 |
| 482 | 10.11188 |
| 489 | 9.791507 |
| 559 | 11.43016 |
| 686 | 11.31306 |
| 687 | 10.58275 |
| 698 | 7.188802 |
| 720 | 11.34764 |
| 801 | 10.12201 |
| 942 | 8.642517 |
| 945 | 7.959645 |
| 951 | 11.52082 |
| 973 | 12.62613 |
| 1010 | 11.66908 |
| 1011 | 17.29628 |
| 1012 | 16.86725 |
| 1013 | 14.6297 |
| 1016 | 17.38947 |
| 1017 | 16.95127 |
| 1018 | 17.92764 |
| 1024 | 15.54797 |
| 1026 | 14.09482 |
| 1028 | 12.2608 |
| 1030 | 14.71636 |
| 1031 | 18.53817 |
| 1040 | 14.35428 |
| 1042 | 17.75641 |
| 1055 | 9.647103 |
| 1090 | 9.681419 |
| 1116 | 13.86313 |
| 1117 | 16.4131 |
| 1118 | 15.0705 |
| 1148 | 14.2175 |
| 1150 | 17.97223 |
| 1160 | 17.78713 |
| 1240 | 14.68468 |
| 1241 | 17.74714 |
| 1243 | 17.81765 |
| 1246 | 17.80269 |
| 1247 | 17.40867 |
| 1248 | 16.28186 |
| 1250 | 18.0722 |
| 1253 | 17.47862 |

TABLE 2-continued

This table provides examples of amino acid positions for which functional circular permutants were experimentally identified. Amino acid positions are numbered according to the S. pyogenes Cas9 protein, set forth as SEQ ID NO: 111.

| Amino Acid Position | Log2 Fold Change |
|---|---|
| 1260 | 15.76726 |
| 1261 | 16.01141 |
| 1262 | 14.499 |
| 1263 | 13.76254 |
| 1265 | 13.42231 |
| 1283 | 18.01082 |
| 1285 | 16.04644 |
| 1298 | 14.78686 |
| 1299 | 12.49114 |
| 1337 | 15.05646 |
| 1366 | 18.45318 |
| 1369 | 16.99543 |

In the examples depicted in FIG. 1, 20 Xs denote where the N-terminal fragment is fused to the C-terminus. In some cases, the N-terminal fragment is fused directly to the C-terminus, and thus in such cases the depicted 20 Xs are not present. In some cases, as discussed in more detail below, the N-terminal fragment (at its N-terminus) is fused to the C-terminus (C-terminus of the remaining C-terminal fragment) via a linker (e.g., a cleavable linker). The linker need not be a polypeptide linker and can be a variety of sizes (e.g., in some cases greater than 20 amino acids in length). Thus, the depicted Xs in FIG. 1 are meant only to show clearly where a linker can be present and are in no way intended to be limiting (e.g., with regard to type of linker and/or size of linker). The sequences set forth in SEQ ID NOs: 21-36 are the same 16 circular permuted Cas9 proteins as those set forth in SEQ ID NOs: 1-16, but for SEQ ID NOs: 21-36 the Xs are a 20 amino acid linker that was used in the examples section below. The linker was $(GGS)_n$, so for the 20 amino acid linker, GGSGGSGGSGGSGGSGGSGG (SEQ ID NO: 44) was used.

In some cases, the process of generating a subject RNA-guided polypeptide (e.g., circular permuted Cas9 protein) (e.g., see FIG. 2) results in added and/or mutated nucleotides at the N-terminus of the generated protein (e.g., circular permuted Cas9 protein). For example, the transposon-mediated process depicted in FIG. 2 results in an altered N-terminus. This is not a required feature of a subject circular permuted Cas9 protein, but can be present. FIG. 1 notes the change to the N-terminus that was present for each of the example circular permuted Cas9 proteins depicted (e.g., see "new start-"). As an illustrative example, for the first circular permuted Cas9 protein depicted in FIG. 1, a 182 amino acid N-terminal fragment (amino acids 1M-182D) was fused to the C-terminus, and the new N-terminus would start with amino acid 183 K (KLFIQ . . . ); however, due to the method by which the circular permuted Cas9 protein was generated, an MMD sequence was added to the new N-terminus.

Thus, in some cases, a subject circular permuted Cas9 protein includes an N-terminal fragment of a Cas9 protein fused to the C-terminus of the Cas9 protein (e.g., in some cases via a linker, e.g., a cleavable linker), where the C-terminal amino acid of the N-terminal fragment (i.e., the C-terminus of the N-terminal fragment) includes an amino acid corresponding to amino acid 182D, 200P, 231G, 271Y, 311E, 1011G, 1017D, 1024K, 1029I, 1030G, 1032A, 1042I, 1245L, 1249P, 1250E, or 1283A of the Cas9 protein sequence set forth in SEQ ID NO: 17 or 111. In some cases, a subject circular permuted Cas9 protein includes an N-terminal fragment of a Cas9 protein fused to the C-terminus of the Cas9 protein (e.g., in some cases via a linker, e.g., a cleavable linker), where the N-terminal fragment includes an amino acid sequence corresponding to amino acids 1-182, 1-200, 1-231, 1-271, 1-311, 1-1011, 1-1017, 1-1024, 1-1029, 1-1030, 1-1032, 1-1042, 1-1245, 1-1249, 1-1250, or 1-1283 of the Cas9 protein sequence set forth in SEQ ID NO: 17 or 111.

Thus, in some cases, a subject circular permuted Cas9 protein (cpCas9) is selected from: cpCas9-182, cpCas9-200, cpCas9-231, cpCas9-271, cpCas9-311, cpCas9-1011, cpCas9-1017, cpCas9-1024, cpCas9-1029, cpCas9-1030, cpCas9-1032, cpCas9-1042, cpCas9-1245, cpCas9-1249, cpCas9-1250, and cpCas9-1283.

By "corresponding" it is meant herein that the amino acid of one protein is the positional equivalent of the other. For example, a protein alignment can be performed between two (or more) RNA-guided polypeptides (e.g., two (or more) Cas9 proteins each from a different species), and the alignment can be used to determine which amino acids are corresponding amino acids. Corresponding amino acids can be identified using primary sequence alignments, and can also be identified using crystal structure overlays if/when such information is available. Any convenient method can be used to identify corresponding amino acids and multiple suitable methods will be known to one of ordinary skill in the art.

Figure 5:
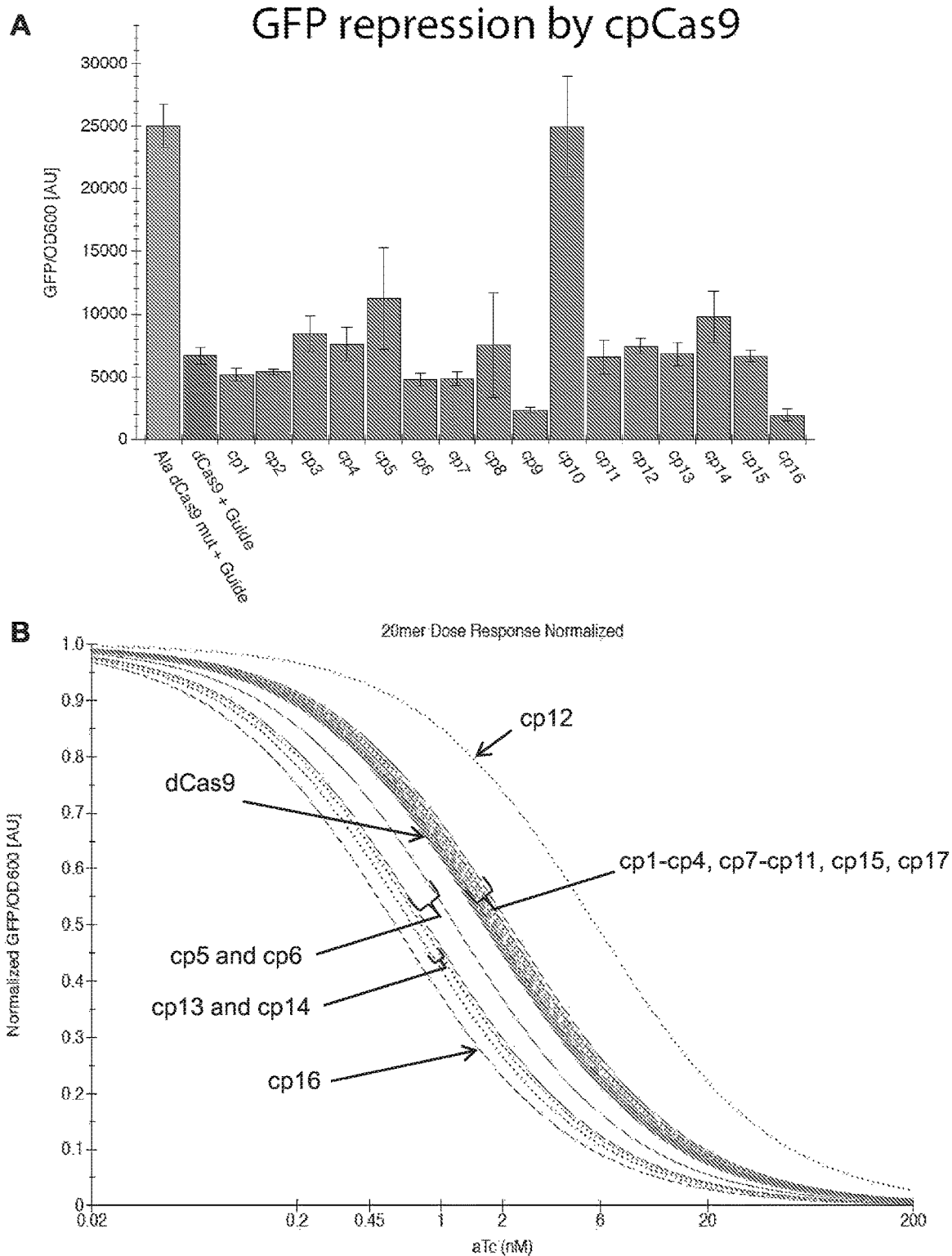
FIG. 5 (panels A-B) presents data related to sequence specific RNA guided binding and repression of a genomic target by circular permuted Cas9 proteins (cpCas9s) recovered from the screen presented in FIG. 3.

In some cases, a subject RNA-guided polypeptide (e.g., circular permuted Cas9 protein) includes an N-terminal fragment of a Cas9 protein fused to the C-terminus of the Cas9 protein (e.g., in some cases via a linker, e.g., a cleavable linker), where the C-terminal amino acid of the N-terminal fragment (i.e., the C-terminus of the N-terminal fragment) includes an amino acid corresponding to amino acid 311E, 1011G, 1245L, 1249P, or 1283A of the Cas9 protein sequence set forth in SEQ ID NO: 17 or 111. In some cases, a subject circular permuted Cas9 protein includes an N-terminal fragment of a Cas9 protein fused to the C-terminus of the Cas9 protein (e.g., in some cases via a linker, e.g., a cleavable linker), where the N-terminal fragment includes an amino acid sequence corresponding to amino acids 1-311, 1-1011, 1-1245, 1-1249, or 1-1283 of the Cas9 protein sequence set forth in SEQ ID NO: 17 or 111. For example, see cp5, 6, 13, 14, and 16 as shown in FIG. 5. Thus, in some cases, a subject circular permuted Cas9 protein (cpCas9) is selected from: cpCas9-311, cpCas9-1011, cpCas9-1245, cpCas9-1249, and cpCas9-1283.

In some cases, a subject RNA-guided polypeptide (e.g., circular permuted Cas9 protein) includes an N-terminal fragment of a Cas9 protein fused (at the N-terminal end of the N-terminal fragment) to the C-terminus of the Cas9 protein (e.g., in some cases via a linker, e.g., a cleavable linker), where the C-terminal amino acid of the N-terminal fragment (i.e., the C-terminus of the N-terminal fragment) includes an amino acid corresponding to amino acid 182D, 200P, 231G, 271Y, 1017D, 1024K, 1029I, 1030G, 1032A, 1042I, or 1250E of Cas9 protein sequence set forth in SEQ ID NO: 17 or 111. In some cases, a subject RNA-guided polypeptide (e.g., circular permuted Cas9 protein) includes an N-terminal fragment of a Cas9 protein fused to the C-terminus of the Cas9 protein (e.g., in some cases via a linker, e.g., a cleavable linker), where the N-terminal fragment includes an amino acid sequence corresponding to amino acids 1-182, 1-200, 1-231, 1-271, 1-1017, 1-1024, 1-1029, 1-1030, 1-1032, 1-1042, or 1-1250 of the Cas9 protein sequence set forth in SEQ ID NO: 17 or 111. For example, see cp1-4, 7-11, 12, and 15 as shown in FIG. 5. Thus, in some cases, a subject circular permuted Cas9 protein (cpCas9) is selected from: cpCas9-182, cpCas9-200, cpCas9-231, cpCas9-271, cpCas9-1017, cpCas9-1024, cpCas9-1029, cpCas9-1030, cpCas9-1032, cpCas9-1042, and cpCas9-1250.

In some cases, a subject RNA-guided polypeptide (e.g., circular permuted Cas9 protein) includes an N-terminal fragment of a Cas9 protein fused to the C-terminus of the Cas9 protein (e.g., in some cases via a linker, e.g., a cleavable linker), where the C-terminal amino acid of the N-terminal fragment (i.e., the C-terminus of the N-terminal fragment) includes an amino acid corresponding to amino acid 182D, 200P, 231G, 271Y, 1017D, 1024K, 1029I, 1030G, 1032A, or 1250E of the Cas9 protein sequence set forth in SEQ ID NO: 17 or 111. In some cases, a subject circular permuted Cas9 protein includes an N-terminal fragment of a Cas9 protein fused to the C-terminus of the Cas9 protein (e.g., in some cases via a linker, e.g., a cleavable linker), where the N-terminal fragment includes an amino acid sequence corresponding to amino acids 1-182, 1-200, 1-231, 1-271, 1-1017, 1-1024, 1-1029, 1-1030, 1-1032, or 1-1250 of Cas9 protein sequence set forth in SEQ ID NO: 17 or 111. For example, see cp1-4, 7-11, and 15 as shown in FIG. 5. Thus, in some cases, a subject circular permuted Cas9 protein (cpCas9) is selected from: cpCas9-182, cpCas9-200, cpCas9-231, cpCas9-271, cpCas9-1017, cpCas9-1024, cpCas9-1029, cpCas9-1030, cpCas9-1032, and cpCas9-1250.

Figure 6:
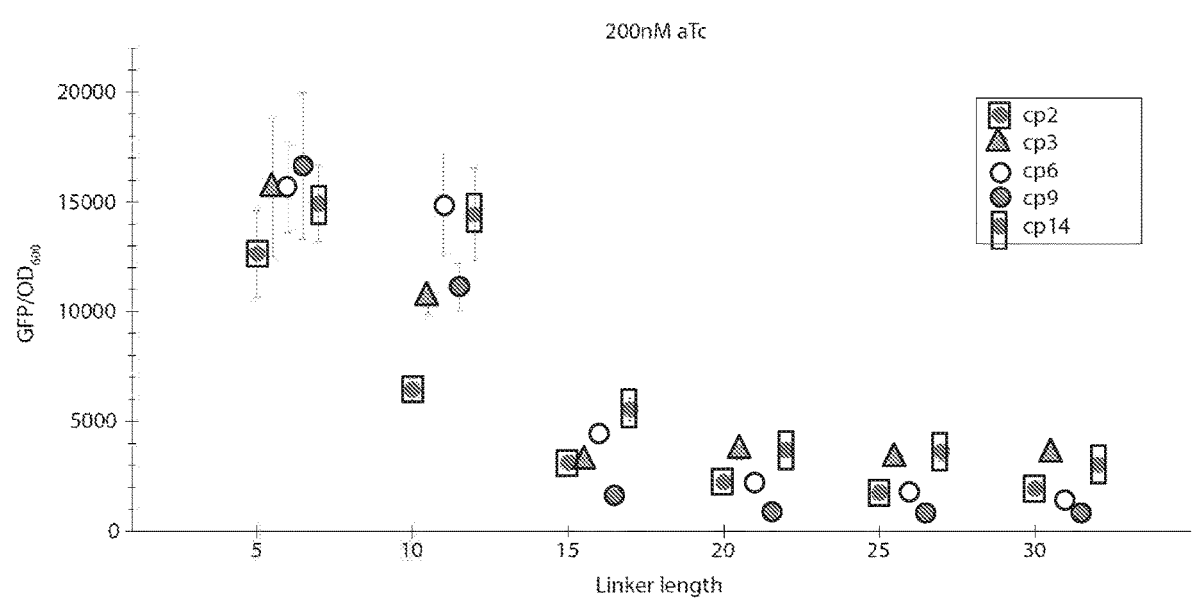
FIG. 6 presents data related to activity (RNA guided sequence specific target DNA binding activity) of circular permuted Cas9 proteins when the linker lengths were modified.

In some cases, a subject RNA-guided polypeptide (e.g., circular permuted Cas9 protein) includes an N-terminal fragment of a Cas9 protein fused to the C-terminus of the Cas9 protein (e.g., in some cases via a linker, e.g., a cleavable linker), where the C-terminal amino acid of the N-terminal fragment (i.e., the C-terminus of the N-terminal fragment) includes an amino acid corresponding to amino acid 200P, 231G, 1011G, 1029I, or 1249P of the Cas9 protein sequence set forth in SEQ ID NO: 17 or 111. In some cases, a subject circular permuted Cas9 protein includes an N-terminal fragment of a Cas9 protein fused to the C-terminus of the Cas9 protein (e.g., in some cases via a linker, e.g., a cleavable linker), where the N-terminal fragment includes an amino acid sequence corresponding to amino acids 1-200, 1-231, 1-1011, 1-1029, or 1-1249 of the Cas9 protein sequence set forth in SEQ ID NO: 17 or 111. For example, see cp2, 3, 6, 9, and 14 as shown in FIG. 6. Thus, in some cases, a subject circular permuted Cas9 protein (cpCas9) is selected from: cpCas9-200, cpCas9-231, cpCas9-1011, cpCas9-1029, and cpCas9-1249.

In some cases, a subject circular permuted Cas9 protein includes an N-terminal fragment of a Cas9 protein fused to the C-terminus of the Cas9 protein (e.g., in some cases via a linker, e.g., a cleavable linker), where the C-terminal amino acid of the N-terminal fragment (i.e., the C-terminus of the N-terminal fragment) includes an amino acid corresponding to any one of the amino acid positions listed in Table 2 (which are numbered according to the Cas9 protein sequence set forth in SEQ ID NO: 111). In some cases, a subject circular permuted Cas9 protein includes an N-terminal fragment of a Cas9 protein fused to the C-terminus of the Cas9 protein (e.g., in some cases via a linker, e.g., a cleavable linker), where the N-terminal fragment includes an amino acid sequence corresponding to amino acids 1-x, where X can be any one of the amino acid positions listed in Table 2.

Thus, in some cases, a subject circular permuted Cas9 protein (cpCas9) is selected from: cpCas9-x, where X can be any one of the amino acid positions listed in Table 2.

Cas9 Polypeptide

As noted above, in some cases, the parent RNA-guided polypeptide is a Cas9 protein. The parent RNA-guided polypeptide is in some cases a wild-type RNA-guided polypeptide. The parent RNA-guided polypeptide is in some cases a non-naturally-occurring (e.g., a variant) RNA-guided polypeptide. A "parent RNA-guided polypeptide" is also referred to herein as a "reference RNA-guided polypeptide." Examples of naturally occurring Cas9 proteins, each of which is suitable to be a 'parent RNA-guided polypeptide', include, but are not limited to, those provided as SEQ ID NOs: 111-912. In some cases, a parent RNA-guided polypeptide has 70% or more identity (e.g. 75% or more, 80% or more, 85% or more, 90% or more, 95% or more, 97% or more, 98% or more, 99% or more, or 100% identity) with the sequence set forth in any one of SEQ ID NOs: 17 and 111-912. For example, in some cases, a parent RNA-guided polypeptide has 80% or more identity (e.g. 85% or more, 90% or more, 95% or more, 97% or more, 98% or more, 99% or more, or 100% identity) with the sequence set forth in any one of SEQ ID NOs: 17 and 111-912. In some cases, a parent RNA-guided polypeptide has 85% or more identity (e.g. 90% or more, 95% or more, 97% or more, 98% or more, 99% or more, or 100% identity) with the sequence set forth in any one of SEQ ID NOs: 17 and 111-912.

As would be known to one of ordinary skill in the art, a Cas9 protein includes an HNH nuclease domain and a RuvC nuclease domain. In a wild type Cas9 protein the RuvC domain cleaves the non-complementary strand (the strand that does not directly hybridized with the guide RNA) of a dsDNA target while the HNH domain cleaves the complementary strand (the strand that does directly hybridized with the guide RNA). Thus, for example (and as described in more detail elsewhere herein) a Cas9 protein lacking a catalytically active RuvC domain cannot cleave the non-complementary strand of a target dsDNA, but may be able to cleave the complementary strand (e.g., if the HNH domain is intact). Likewise, a Cas9 protein lacking a catalytically active HNH domain cannot cleave the complementary strand of a target dsDNA, but may be able to cleave the non-complementary strand (e.g., if the RuvC domain is intact). If a Cas9 protein lacks a catalytically active HNH domain and lacks a catalytically active RuvC domain, then the protein does not cleave target DNA, unless such an activity is provided by a heterologous protein (e.g., a fusion partner).

The RuvC domain of a wild type Cas9 protein is referred to herein as a split RuvC domain because the primary amino acid sequence of a wild type Cas9 protein includes 3 separate stretches (referred to herein as "RuvC subdomains") of primary amino acid sequence that each make up a portion of the RuvC domain despite the fact that the three separate stretches are separated from one another by intervening primary amino acid sequence. The three subdomains fold to form a RuvC domain. In other words, a wild type Cas9 protein has 3 different regions (sometimes referred to as subdomains RuvC-I, RuvC-II, and RucC-III), that are not contiguous with respect to the primary amino acid sequence of the Cas9 protein, but fold together to form a RuvC domain once the protein is produced and folds. As would be known to one of ordinary skill in the art, a wild type Cas9 protein includes, in order: i) a first RuvC subdomain; ii) a second RuvC subdomain; iii) an HNH domain; and iv) a third RuvC subdomain Cas9 proteins can be said to share at least 4 key motifs with a conserved architecture. Motifs 1, 2, and 4 are RuvC like motifs (from RuvC-I, RuvC-II, and RuvC-III subdomains, respectively) while motif 3 is an HNH-motif from the HNH domain. The motifs set forth in Table 1 may not represent the entire RuvC-like (RuvC subdomains) and/or HNH domains as accepted in the art, but Table 1 does present motifs that can be used to help determine whether a given protein is a Cas9 protein.

TABLE 1

Table 1 lists 4 motifs that are present in Cas9 sequences from various species.

| Motif # | Motif | Amino acids (residue #s) | Highly conserved |
|---|---|---|---|
| 1 | RuvC-like I | IGLDIGTNSVGWAVI (7-21 of wild type) (SEQ ID NO: 37) | D10, G12, G17 |
| 2 | RuvC-like II | IVIEMARE (759-766 of wild type) (SEQ ID NO: 38) | E762 |
| 3 | HNH-motif | DVDHIVPQSFLKDDS IDNKVLTRSDKN (837-863 of wild type) (SEQ ID NO: 39) | H840, N854, N863 |
| 4 | RuvC-like II | HHAHDAYL (982-989 of wild type) (SEQ ID NO: 40) | H982, H983, A984, D986, A987 |

The amino acids listed here are from the wild type Cas9 protein from *S. pyogenes* (D10 and H840 are bold and underlined) set forth as SEQ ID NO: 111.

In some cases, a suitable a parent RNA-guided polypeptide and/or a subject RNA-guided polypeptide (e.g., a circular permutant of the parent), includes an amino acid sequence having 4 motifs, each of motifs 1-4 having 60% or more amino acid sequence identity (e.g., 70% or more, 75% or more, 80% or more, 85% or more, 90% or more, 95% or more, 99% or more or 100% amino acid sequence identity) to motifs 1-4 set forth in SEQ ID NOs: 37-40, respectively, as depicted in Table 1, or to the corresponding portions in any of the amino acid sequences set forth in SEQ ID NOs: 111-912. In some cases, a suitable a parent RNA-guided polypeptide and/or a subject RNA-guided polypeptide (e.g., a circular permutant of the parent), includes an amino acid sequence having 4 motifs, each of motifs 1-4 having 80% or more amino acid sequence identity (e.g., 85% or more, 90% or more, 95% or more, 99% or more or 100% amino acid sequence identity) to motifs 1-4 set forth in SEQ ID NOs: 37-40, respectively, as depicted in Table 1, or to the corresponding portions in any of the amino acid sequences set forth in SEQ ID NOs: 111-912. In some cases, a suitable a parent RNA-guided polypeptide and/or a subject RNA-guided polypeptide (e.g., a circular permutant of the parent), includes an amino acid sequence having 4 motifs, each of motifs 1-4 having 90% or more amino acid sequence identity (e.g., 95% or more, 99% or more or 100% amino acid sequence identity) to motifs 1-4 set forth in SEQ ID NOs: 37-40, respectively, as depicted in Table 1, or to the corresponding portions in any of the amino acid sequences set forth in SEQ ID NOs: 111-912.

As discussed in more elsewhere herein, a suitable a parent RNA-guided polypeptide and/or a subject RNA-guided polypeptide (e.g., a circular permutant of the parent) can include one or more amino acid mutations that render the protein to be a nickase or a nuclease inactive (e.g., RuvC domain and HNH domain catalytically inactive) protein.

Protein Variants

Any Cas9 protein can be used as a parent RNA-guided polypeptide (as described above) or as a Cas9 polypeptide portion of a subject Cas9 fusion polypeptide (described in more detail below). A subject RNA-guided polypeptide (e.g., circular permutant Cas9 protein) and/or a subject Cas9 fusion polypeptide can lack a catalytically active RuvC domain and/or can lack a catalytically active HNH domain. Thus, a subject RNA-guided polypeptide (e.g., circular permutant Cas9 protein) and/or a subject Cas9 fusion polypeptide can be nickase or can be a catalytically inactive protein.

In some cases, a subject RNA-guided polypeptide (e.g., circular permutant Cas9 protein) and/or a subject Cas9 fusion polypeptide includes a Cas9 polypeptide portion that has reduced catalytic activity (e.g., a Cas9 protein with nickase activity or a Cas9 protein that is catalytically inactive, e.g., dCas9). For example, when a Cas9 protein has a mutation at one or more amino acid positions corresponding to D10, G12, G17, E762, H840, N854, N863, H982, H983, A984, D986, and/or a A987 of the Cas9 protein set forth in SEQ ID NO: 111 (e.g., D10A, G12A, G17A, E762A, H840A, N854A, N863A, H982A, H983A, A984A, and/or D986A), the variant Cas9 protein can still bind to target DNA in a site-specific manner (because it is still guided to a target DNA sequence by a guide RNA) as long as it retains the ability to interact with the guide RNA.

In some cases, the a subject RNA-guided polypeptide (e.g., circular permutant Cas9 protein) and/or a subject Cas9 fusion polypeptide is a nickase (e.g., cleaves one strand of a double stranded target nucleic acid but not the other strand) (e.g., the Cas9 polypeptide portion of a subject Cas9 fusion polypeptide can be a nickase, e.g., can include one or more amino acid mutations that make it a nickase). For example, in some cases the subject RNA-guided polypeptide (e.g., circular permutant Cas9 protein) and/or a subject Cas9 fusion polypeptide has a mutation in a catalytic domain (e.g., a mutation in a RuvC or HNH domain).

For example, in some cases, a subject RNA-guided polypeptide (e.g., circular permutant Cas9 protein) and/or a subject Cas9 fusion polypeptide can cleave the complementary strand of a target nucleic acid but has reduced ability to cleave the non-complementary strand of a target nucleic acid. For example, the subject RNA-guided polypeptide (e.g., circular permutant Cas9 protein) and/or a subject Cas9 fusion polypeptide can have a mutation (amino acid substitution) that reduces the function of the RuvC domain. As a non-limiting example, in some cases, a subject RNA-guided polypeptide (e.g., circular permutant Cas9 protein) and/or a subject Cas9 fusion polypeptide has a mutation at residue D10 (e.g., D10A, aspartate to alanine) of SEQ ID NO: 111 (or the corresponding position of any of the proteins set forth in SEQ ID NOs: 112-912) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). Examples of such amino acid positions in a RuvC domain can include (as depicted in Table 1): D10, G12, G17, E762, H982, H983, A984, D986, and/or A987 of the Cas9 protein set forth in SEQ ID NO: 5 (e.g., D10A, G12A, G17A, E762A, H982A, H983A, A984A, and/or D986A).

In some cases, subject RNA-guided polypeptide (e.g., circular permutant Cas9 protein) and/or a subject Cas9 fusion polypeptide can cleave the non-complementary strand of a target nucleic acid but has reduced ability to cleave the complementary strand of the target nucleic acid. For example, the subject RNA-guided polypeptide (e.g., circular permutant Cas9 protein) and/or a subject Cas9 fusion polypeptide can have a mutation (amino acid substitution) that reduces the function of the HNH domain Thus, the subject RNA-guided polypeptide (e.g., circular permutant Cas9 protein) and/or a subject Cas9 fusion polypeptide can be a nickase that cleaves the non-complementary strand, but does not cleave the complementary strand (e.g., does not cleave a single stranded target nucleic acid). As a non-limiting example, in some embodiments, the subject RNA-guided polypeptide (e.g., circular permutant Cas9 protein) and/or a subject Cas9 fusion polypeptide has a mutation at position H840 (e.g., an H840A mutation, histidine to alanine) of SEQ ID NO: 111 (or the corresponding position of any of the proteins set forth as SEQ ID NOs: 112-912 and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid). Examples of such amino acid positions in an HNH domain can include (as depicted in Table 1): H840, N854, and/or N863 of the Cas9 protein set forth in SEQ ID NO: 111 (e.g., H840A, N854A, and/or N863A).

In some cases, a subject RNA-guided polypeptide (e.g., circular permutant Cas9 protein) and/or a subject Cas9 fusion polypeptide has a reduced ability to cleave both the complementary and the non-complementary strands of a double stranded target nucleic acid. In some cases, the parent RNA-guided polypeptide (used to generate a subject RNA-guided polypeptide, e.g., a circular permuted Cas9 protein) is a dCas9 protein. As a non-limiting example, in some cases, the subject RNA-guided polypeptide (e.g., circular permutant Cas9 protein) and/or a subject Cas9 fusion polypeptide harbors mutations at residues D10 and H840 (e.g., D10A and H840A) of SEQ ID NO: 111 (or the corresponding residues of any of the proteins set forth as SEQ ID NOs: 112-912) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. For example, a subject RNA-guided polypeptide (e.g., circular permutant Cas9 protein) and/or a subject Cas9 fusion polypeptide can have a mutation in one or more of amino acid positions in (i) a RuvC domain (as depicted in Table 1): D10, G12, G17, E762, H982, H983, A984, D986, and/or A987 of the Cas9 protein set forth in SEQ ID NO: 111 (e.g., D10A, G12A, G17A, E762A, H982A, H983A, A984A, and/or D986A); and one or more of amino acid positions in (ii) an HNH domain (as depicted in Table 1): H840, N854, and/or N863 of the Cas9 protein set forth in SEQ ID NO: 111 (e.g., H840A, N854A, and/or N863A).

In some cases, the parent RNA-guided polypeptide (used to generate a subject RNA-guided polypeptide, e.g., a circular permuted Cas9 protein) is a high fidelity (HF) Cas9 polypeptide (e.g., see Kleinstiver et al. (2016) Nature 529: 490), and thus the generated subject RNA-guided polypeptide (e.g., circular permuted Cas9 protein) includes the same amino acid mutations that caused the parent protein to be high fidelity. For example, amino acids N497, R661, Q695, and Q926 of the amino acid sequence set forth as (SEQ ID NO:111) (or the corresponding position of another Cas9 protein, e.g., a protein having the amino acid sequence of any of the sequences set forth as SEQ ID NOs: 112-912) can be substituted, e.g., with alanine. For example, an HF parent Cas9 polypeptide can comprise an amino acid sequence having at least 90%, at least 95%, at least 98%, at least 99%, or 100%, amino acid sequence identity to the amino acid sequence set forth as SEQ ID NO: 111 where amino acids N497, R661, Q695, and Q926 are substituted, e.g., with alanine.

In some cases, a suitable parent RNA-guided polypeptide is a Cas9 polypeptide that exhibits altered PAM specificity. See, e.g., Kleinstiver et al. (2015) Nature 523:481.

"Protospacer Adjacent Motif" (PAM)

A wild type CRISPR/Cas protein (e.g., Cas9 protein) normally has nuclease activity that cleaves a target nucleic acid (e.g., a double stranded DNA (dsDNA)) at a target site defined by the region of complementarity between the guide sequence of the guide RNA and the target nucleic acid. In some cases, site-specific targeting to the target nucleic acid occurs at locations determined by both (i) base-pairing complementarity between the guide nucleic acid and the target nucleic acid; and (ii) a short motif referred to as the "protospacer adjacent motif" (PAM) in the target nucleic acid. For example, when a Cas9 protein binds to (in some cases cleaves) a dsDNA target nucleic acid, the PAM sequence that is recognized (bound) by the Cas9 polypeptide is present on the non-complementary strand (the strand that does not hybridize with the targeting segment of the guide nucleic acid) of the target DNA. In some cases, a PAM sequence has a length in a range of from 1 nt to 15 nt (e.g., 1 nt to 14 nt, 1 nt to 13 nt, 1 nt to 12 nt, 1 nt to 11 nt, 1 nt to 10 nt, 1 nt to 9 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 15 nt, 2 nt to 14 nt, 2 nt to 13 nt, 2 nt to 12 nt, 2 nt to 11 nt, 2 nt to 10 nt, 2 nt to 9 nt, 2 nt to 8 nt, 2 nt to 7 nt, 2 nt to 6 nt, 2 nt to 5 nt, 2 nt to 4 nt, 2 nt to 3 nt, 2 nt, or 3 nt).

CRISRPR/Cas (e.g., Cas9) proteins from different species can have different PAM sequence requirements. For example, in some embodiments (e.g., when the Cas9 protein is derived from *S. pyogenes* or a closely related Cas9 is used; see for example, Chylinski et al., RNA Biol. 2013 May; 10(5):726-37; and Jinek et al., Science. 2012 Aug. 17; 337(6096):816-21; both of which are hereby incorporated by reference in their entirety), the PAM sequence can be NRG because the *S. pyogenes* Cas9 PAM (PAM sequence) is NAG or NGG (or NRG where "R" is A or G). For example, a Cas9 PAM sequence for *S. pyogenes* Cas9 can be: NGG, NAG, AGG, CGG, GGG, TGG, AAG, CAG, GAG, and TAG. In some cases, the PAM is NGG.

In some cases (e.g., when a Cas9 protein is derived from the Cas9 protein of *Neisseria meningitidis* or a closely related Cas9 is used), the PAM sequence (e.g., of a target nucleic acid) can be 5'-NNNNGANN-3', 5'-NNNNGTTN-3', 5'-NNNNGNNT-3', 5'-NNNNGTNN-3', 5'-NNNNG-NTN-3', or 5'-NNNNGATT-3', where N is any nucleotide. In some embodiments (e.g., when a Cas9 protein is derived from *Streptococcus thermophilus* #1 or a closely related Cas9 is used), the PAM sequence (e.g., of a target nucleic acid) can be 5'-NNAGAA-3', 5'-NNAGGA-3', 5'-NNG-GAA-3', 5'-NNANAA-3', or 5'-NNGGGA-3' where N is any nucleotide. In some embodiments (e.g., when a Cas9 protein is derived from *Treponema denticola* (TD) or a closely related Cas9 is used), the PAM sequence (e.g., of a target nucleic acid) can be 5'-NAAAAN-3', 5'-NAAAAC-3', 5'-NAAANC-3', 5'-NANAAC-3', or 5'-NNAAAC-3', where N is any nucleotide. As would be known by one of ordinary skill in the art, additional PAM sequences for other Cas9 polypeptides can readily be determined using bioinformatic analysis (e.g., analysis of genomic sequencing data), and/or routine experimentation. See Esvelt et al., Nat Methods. 2013 November; 10(11):1116-21, for additional information.

Linker of an RNA-Guided Polypeptide

A subject RNA-guided polypeptide includes a linker connecting the N-terminal end of an N-terminal fragment of a parent RNA-guided polypeptide to the C-terminal end of a C-terminal fragment of the parent RNA-guided polypeptide (e.g., connecting the N-terminal end of an N-terminal fragment to the C-terminal end of the remaining C-terminal fragment).

The inventors have discovered that in some cases, when the linker is short (e.g., a 5 amino acid linker, a 7 amino acid linker, a 10 amino acid linker) the subject RNA-guided polypeptide (e.g., circular permuted Cas9 protein) has reduced activity (in some cases no detectable activity) compared to when the linker is longer (e.g., 15 amino acids, 20 amino acids, etc.) (e.g., refer to FIG. 6). For example the subject RNA-guided polypeptide can have reduced site specific binding activity (guide RNA guided sequence specific target nucleic acid biding activity), e.g., in some cases no detectable site specific binding activity.

Thus, in some cases, a subject RNA-guided polypeptide (e.g., circular permuted Cas9 protein) includes a linker that is has a length equivalent to (e.g., having a length of) 11 amino acids or greater (e.g., 12 amino acids or greater, 13 amino acids or greater, 14 amino acids or greater, 15 amino acids or greater, 16 amino acids or greater, etc.). In some cases, a subject RNA-guided polypeptide (e.g., circular permuted Cas9 protein) includes a linker that is has a length equivalent to (e.g., having a length of) 15 amino acids or greater (e.g., 16 amino acids or greater, etc.). In some cases, a subject RNA-guided polypeptide (e.g., circular permuted Cas9 protein) includes a linker that is has a length equivalent to (e.g., having a length in) a range of from 11 to 300 amino acids (e.g., 11-250, 11-200, 11-150, 11-100, 11-75, 11-50, 11-30, 12-300, 12-250, 12-200, 12-150, 12-100, 12-75, 12-50, 12-30, 13-300, 13-250, 13-200, 13-150, 13-100, 13-75, 13-50, 13-30, 14-300, 14-250, 14-200, 14-150, 14-100, 14-75, 14-50, 14-30, 15-300, 15-250, 15-200, 15-150, 15-100, 15-75, 15-50, or 15-30 amino acids). In some cases, a subject RNA-guided polypeptide (e.g., circular permuted Cas9 protein) includes a linker that is has a length equivalent to (e.g., having a length in) a range of from 15 to 300 amino acids (e.g., 15-250, 15-200, 15-150, 15-100, 15-75, 15-50, or 15-30 amino acids).

The linker (connecting the N-terminal fragment to the C-terminal fragment) of a subject RNA-guided polypeptide (e.g., circular permuted Cas9 protein) need not be a polypeptide linker. For example, in some cases, the RNA-guided polypeptide is not produced as one single polypeptide molecule. For example, in some cases the RNA-guided polypeptide can be generated by separately producing the N- and C-terminal fragments, which can be linked to one another using a chemical linker. Because the linkers used in the examples section below were polypeptide linkers, and the length of linkers can affect protein activity (discussed in more detail below), linker length (e.g., when meaning to encompass all linkers, not just polypeptide linkers) is referred to herein as "equivalent to" a length of a given number of amino acids. Thus, a linker having a length equivalent to 11 amino acids encompasses a polypeptide linker that is 11 amino acids in length, and also encompasses a non-polypeptide linker having the same length (e.g., measured in units of amino acids, amino acid equivalents, even though the linker itself is not necessarily made of amino acids). Thus, when a linker is said to have a length 'equivalent to' X amino acids, or a length 'equivalent to' a range of from X-X amino acids, such a linker can be a polypeptide linker, but is not necessarily a polypeptide linker. If the above linker is a polypeptide linker, then the linker can also be said to have a length of X amino acids, or a length in a range of from X-X amino acids, respectively. The unfolded contour length of a peptide can be taken to be 4±0.2 Angstroms (Å) x the number of amino acids.

The inventors have also discovered that when the linker is short (e.g., a 5 amino acid linker, a 7 amino acid linker, a 10 amino acid linker) and the subject RNA-guided polypeptide (e.g., circular permuted Cas9 protein) has reduced activity (e.g., guide RNA guided sequence specific target nucleic acid binding activity) compared to when the linker is longer (e.g., 15 amino acids, 20 amino acids, etc.), that cleavage of the linker (i.e., post-translational cleavage) restores activity (e.g., refer to FIG. 10). Without wishing to be bound by theory, this appears to be due to a three dimensional constraint that is imposed on the subject RNA-guided polypeptide (e.g., circular permuted Cas9 protein) by a short linker, and when the linker is cleaved the constraint is removed. Thus, the linker can be present at the DNA level such that the protein is translated as one continuous polypeptide (that likely cannot fold quite right), and post-translational cleavage of the linker allows a functional protein to form (e.g., one that can fold properly) despite the fact that it is now is made up of two separate polypeptides (due to the cleavage). Such an RNA-guided polypeptide is therefore conditionally active, having reduced activity (in some cases no activity) when the cleavable linker is intact (uncleaved) relative to when the cleavable linker is cleaved. A conditionally active RNA-guided polypeptide (e.g., a conditionally active circular permuted Cas9 protein) is sometimes referred to herein as a "caged RNA-guided polypeptide (e.g., "caged circular permuted Cas9 protein").

As noted above, cleavage of the cleavable linker of a subject conditionally active RNA-guided polypeptide (e.g., a conditionally active circular permuted Cas9 protein) causes an increase in activity of the RNA-guided polypeptide. The activity referred to is the RNA guided sequence specific target DNA binding activity of the subject RNA-guided polypeptide (e.g., circular permuted Cas9 protein). This can be measured in a number of different ways and any convenient method can be used. For example, in cases where the subject RNA-guided polypeptide (e.g., circular permuted Cas9 protein) has target DNA cleavage activity (e.g., the ability to make a double strand break or the ability to make single strand break, e.g., nickase activity), cleavage of the target nucleic acid can be detected directly (e.g., via visualization the substrate and/or product nucleic acids), or can be detected indirectly (e.g., via detecting mutations in the target nucleic acid that result from cleavage of the target, detecting changes in a detectable signal such as fluorescence from green fluorescent protein (GFP) that result from target cleavage, detecting changes in gene expression that result from target cleavage, and the like). In cases where the subject RNA-guided polypeptide (e.g., circular permuted Cas9 protein) does not have cleavage activity and/or has some other detectable activity (e.g., some form of target nucleic acid modification other than cleavage such as methylation, some form of transcriptional modulation activity, some form of protein modification activity such as histone modification activity, and the like), activity can be detected by measuring a readout corresponding to the expected activity. For example, in some cases where the subject RNA-guided polypeptide (e.g., circular permuted Cas9 protein) has no cleavage activity a change in target gene expression can be detected, e.g., because a catalytically inactive dCas9, and therefore in some cases a catalytically inactive subject RNA-guided polypeptide, can act as a transcriptional repressor.

In some cases, activity of the subject RNA-guided polypeptide (e.g., circular permuted Cas9 protein) when the cleavable linker is cleaved is 1.1-fold or more (e.g., 1.2-fold or more, 1.3-fold or more, 1.4-fold or more, 1.5-fold or more, 1.6-fold or more, 1.8-fold or more, 2-fold or more, 2.5-fold or more, 3-fold or more, 4-fold or more, 5-fold or more, 8-fold or more, or 10-fold or more) relative to activity when the cleavable linker is intact (uncleaved). In some cases, activity of the subject RNA-guided polypeptide when the cleavable linker is cleaved is 1.5-fold or more (e.g., 1.6-fold or more, 1.8-fold or more, 2-fold or more, 2.5-fold or more, 3-fold or more, 4-fold or more, 5-fold or more, 8-fold or more, or 10-fold or more) relative to activity when the cleavable linker is intact (uncleaved). In some cases, activity of the subject RNA-guided polypeptide when the cleavable linker is cleaved is 2-fold or more (e.g., 2.5-fold or more, 3-fold or more, 4-fold or more, 5-fold or more, 8-fold or more, or 10-fold or more) relative to activity when the cleavable linker is intact (uncleaved). In some cases, activity of the subject RNA-guided polypeptide when the cleavable linker is cleaved is 5-fold or more (e.g., 2.5-fold or more, 3-fold or more, 4-fold or more, 5-fold or more, 8-fold or more, or 10-fold or more) relative to activity when the cleavable linker is intact (uncleaved).

In some cases, activity of the subject RNA-guided polypeptide (e.g., circular permuted Cas9 protein) when the cleavable linker is cleaved relative to the activity when the cleavable linker is intact (uncleaved) is in a range of from 1.1-fold to 100-fold (e.g., from 1.1-fold to 50-fold, from 1.1-fold to 20-fold, from 1.1-fold to 10-fold, from 1.2-fold to 100-fold, from 1.2-fold to 50-fold, from 1.2-fold to 20-fold, from 1.2-fold to 10-fold, from 1.3-fold to 100-fold, 1.3-fold to 50-fold, from 1.3-fold to 20-fold, from 1.3-fold to 10-fold, from 1.5-fold to 100-fold, 1.5-fold to 50-fold, from 1.5-fold to 20-fold, from 1.5-fold to 10-fold, from 1.8-fold to 100-fold, 1.8-fold to 50-fold, from 1.8-fold to 20-fold, from 1.8-fold to 10-fold, from 2-fold to 100-fold, 2-fold to 50-fold, from 2-fold to 20-fold, from 2-fold to 10-fold, from 2.5-fold to 100-fold, 2.5-fold to 50-fold, from 2.5-fold to 20-fold, from 2.5-fold to 10-fold, from 3-fold to 100-fold, 3-fold to 50-fold, from 3-fold to 20-fold, from 3-fold to 10-fold, from 4-fold to 100-fold, 4-fold to 50-fold, from 4-fold to 20-fold, from 4-fold to 10-fold, from 5-fold to 100-fold, 5-fold to 50-fold, from 5-fold to 20-fold, from 5-fold to 10-fold, from 10-fold to 100-fold, 10-fold to 50-fold, or from 10-fold to 20-fold). In some cases, activity of the subject RNA-guided polypeptide (e.g., circular permuted Cas9 protein) when the cleavable linker is cleaved relative to the activity when the cleavable linker is intact (uncleaved) is in a range of from 5-fold to 100-fold. In some cases, activity of the subject RNA-guided polypeptide (e.g., circular permuted Cas9 protein) when the cleavable linker is cleaved relative to the activity when the cleavable linker is intact (uncleaved) is in a range of from 3-fold to 50-fold.

In other words, in some cases, the increase in activity caused by cleavage of the cleavable linker is 1.1-fold or more (e.g., 1.2-fold or more, 1.3-fold or more, 1.4-fold or more, 1.5-fold or more, 1.6-fold or more, 1.8-fold or more, 2-fold or more, 2.5-fold or more, 3-fold or more, 4-fold or more, 5-fold or more, 8-fold or more, or 10-fold or more). In some cases, the increase in activity caused by cleavage of the cleavable linker is 1.5-fold or more (e.g., 1.6-fold or more, 2-fold or more, 2-fold or more, 2.5-fold or more, 3-fold or more, 4-fold or more, 5-fold or more, 8-fold or more, or 10-fold or more). In some cases, the increase in activity caused by cleavage of the cleavable linker is 2-fold or more (e.g., 2.2-fold or more, 2.5-fold or more, 3-fold or more, 4-fold or more, 5-fold or more, 8-fold or more, or 10-fold or more).

In some cases, the increase in activity caused by cleavage of the cleavable linker is in a range of from 1.1-fold to 100-fold (e.g., from 1.1-fold to 50-fold, from 1.1-fold to 20-fold, from 1.1-fold to 10-fold, from 1.2-fold to 100-fold, from 1.2-fold to 50-fold, from 1.2-fold to 20-fold, from 1.2-fold to 10-fold, from 1.3-fold to 100-fold, 1.3-fold to 50-fold, from 1.3-fold to 20-fold, from 1.3-fold to 10-fold, from 1.5-fold to 100-fold, 1.5-fold to 50-fold, from 1.5-fold to 20-fold, from 1.5-fold to 10-fold, from 1.8-fold to 100-fold, 1.8-fold to 50-fold, from 1.8-fold to 20-fold, from 1.8-fold to 10-fold, from 2-fold to 100-fold, 2-fold to 50-fold, from 2-fold to 20-fold, from 2-fold to 10-fold, from 2.5-fold to 100-fold, 2.5-fold to 50-fold, from 2.5-fold to 20-fold, from 2.5-fold to 10-fold, from 3-fold to 100-fold, 3-fold to 50-fold, from 3-fold to 20-fold, from 3-fold to 10-fold, from 4-fold to 100-fold, 4-fold to 50-fold, from 4-fold to 20-fold, from 4-fold to 10-fold, from 5-fold to 100-fold, 5-fold to 50-fold, from 5-fold to 20-fold, from 5-fold to 10-fold, from 10-fold to 100-fold, 10-fold to 50-fold, or from 10-fold to 20-fold). In some cases, the increase in activity caused by cleavage of the cleavable linker is in a range of from 1.5-fold to 100-fold. In some cases, the increase in activity caused by cleavage of the cleavable linker is in a range of from 2-fold to 100-fold. In some cases, the increase in activity caused by cleavage of the cleavable linker is in a range of from 3-fold to 100-fold. In some cases, the increase in activity caused by cleavage of the cleavable linker is in a range of from 3-fold to 50-fold.

As noted above, the linker of a subject RNA-guided polypeptide (e.g., a conditionally active RNA-guided polypeptide) need not be a polypeptide linker. If the subject RNA-guided polypeptide is a conditionally active RNA-guided polypeptide, the presence of the linker causes reduced protein activity and cleavage of the linker (or cleavage followed by lengthening of the linker) results in an increase in activity. Examples of suitable cleavable linker types include but are not limited to: acid-labile linkers, photolabile linkers, dimethyl linkers, proteolytically cleavable linkers (i.e., cleavable by a protease), and disulfide containing linkers (e.g., which can be cleavable by glutathione). Thus, in some cases, the linker is one or more of: an acid-labile linker, a photolabile linker, a dimethyl linker, a proteolytically cleavable linker (i.e., cleavable by a protease), and a disulfide containing linker (e.g., which can be cleavable by glutathione). In other words, in some cases the linker is selected from: an acid-labile linker, a photolabile linker, a dimethyl linker, a proteolytically cleavable linker (i.e., cleavable by a protease), and a disulfide containing linker (e.g., which can be cleavable by glutathione).

In some embodiments in which a subject RNA-guided polypeptide is conditionally active (e.g., where cleavage of the cleavable linker causes an increase in activity of the RNA-guided polypeptide), the RNA-guided polypeptide, e.g., circular permuted Cas9 protein, includes a cleavable linker connecting the N-terminal end of an N-terminal fragment of a parent protein (e.g., Cas9 protein) to the C-terminal end of a C-terminal fragment (e.g., the C-terminal end of the remaining C-terminal fragment) the cleavable linker is a polypeptide linker having a length equivalent to (e.g., having a length in) a range of from 1-14 amino acids (e.g., 1-13, 1-12, 1-11, 1-10, 1-9, 1-8, 1-7, 1-6, 1-5, 2-14, 2-13, 2-12, 2-11, 2-10, 2-9, 2-8, 2-7, 2-6, 2-5, 3-14, 3-13, 3-12, 3-11, 3-10, 3-9, 3-8, 3-7, 3-6, 3-5, 4-14, 4-13, 4-12, 4-11, 4-10, 4-9, 4-8, 4-7, 4-6, 4-5, 5-14, 5-13, 5-12, 5-11, 5-10, 5-9, 5-8, 5-7, or 5-6 amino acids). In some cases, the cleavable linker is a polypeptide linker having a length equivalent to (e.g., having a length in) a range of from 1-10 amino acids (e.g., 1-9, 1-8, 1-7, 1-6, 1-5, 2-10, 2-9, 2-8, 2-7, 2-6, 2-5, 3-10, 3-9, 3-8, 3-7, 3-6, 3-5, 4-10, 4-9, 4-8, 4-7, 4-6, 4-5, 5-10, 5-9, 5-8, 5-7, or 5-6 amino acids). In some cases, the cleavable linker is a polypeptide linker having a length equivalent to (e.g., having a length in) a range of from 5-10 amino acids (e.g., 5-9, 5-8, 5-7, or 5-6 amino acids).

In some cases, the cleavable linker is a polypeptide linker. In some cases, the polypeptide linker comprises a target sequence for a protease (i.e., a protease cleavage site) (e.g., a bacterial protease; a viral protease; a eukaryotic cell protease; a mammalian cell protease; a protease upregulated during disease/ailment such as cancer, atherosclerosis, osteoporosis, Alzheimer disease, hypertension, inflammation, neurodegenerative disorders, rheumatoid arthritis, bronchiectasis, chronic asthma, cystic fibrosis, HIV associated dementia, stroke, and/or bone disease) (e.g., see Choi et al., Theranostics. 2012; 2(2):156-78; and Alan Barrett, Neil Rawlings, and J. Woessner: Handbook of Proteolytic Enzymes, Academic Press, Dec. 3, 2012, ISBN: 978-0-12-382219-2). Suitable polypeptide linkers can include those that can be cleaved by (is cleavable by) the following non-exhaustive and non-limiting list of proteases: a cysteine cathepsin (e.g., Cathepsin K, Cathepsin B, Cathepsin L), an aspartic cathepsin (e.g., Cathepsin E, Cathepsin D), enterokinase, a Kallikrein (hK) (e.g., hK1, hK2, PSA (hK 3), hK10, hK15), a serine protease (e.g., uPA, uPAR), tissue plasminogen activator (tPA), afurin, a matrix metalloproteinase (e.g., MMP-1, MMP-2, MMP-3, MMP-7, MMP-8, MMP-9, MMP-10, MMP-11, MMP-13, MMP-14), a membrane metalloproteinase (e.g., MT1-MMP, MT2-MMP), a caspase (e.g., caspase-3), CP, FAP, plasmin, TOP, Thrombin, and Trypsin. For example in some cases, a subject circular permuted Cas9 protein includes a cleavable polypeptide linker that can be cleaved by (is cleavable by) a protease selected from: a cysteine cathepsin (e.g., Cathepsin K, Cathepsin B, Cathepsin L), an aspartic cathepsin (e.g., Cathepsin E, Cathepsin D), a Kallikrein (hK) (e.g., hK1, hK2, PSA (hK 3), hK10, hK15), a serine protease (e.g., uPA, uPAR), a matrix metalloproteinase (e.g., MMP-1, MMP-2, MMP-3, MMP-7, MMP-8, MMP-9, MMP-10, MMP-11, MMP-13, MMP-14), a membrane metalloproteinase (e.g., MT1-MMP, MT2-MMP), a caspase (e.g., caspase-3), CP, FAP, plasmin, TOP, Thrombin, and Trypsin.

In some cases, the polypeptide linker comprises a target sequence for a protease upregulated in cancer (e.g., upregulated in a cancerous cell) (e.g., see Choi et al., Theranostics. 2012; 2(2):156-78. doi: 10.7150/thno.4068; Rakashanda et al., October 2012, Biotechnology and Molecular Biology Review Vol. 7(4), pp. 90-101; and Chan et al., PLoS One. 2012; 7(1):e30397. doi: 10.1371/journal.pone.0030397). Suitable polypeptide linkers can include those that can be cleaved by (is cleavable by) the following non-exhaustive and non-limiting list of cancer-associated proteases: Caspase-3, Cathepsin B, CP, FAP, Kallikrein 2 (hK2), MMP-2, MMP-7, MMP-9, MMP-14, plasmin, PSA, TOP, uPA, Thrombin, Trypsin, uPA, and PRSS23. For example in some cases, a subject circular permuted Cas9 protein includes a cleavable polypeptide linker that can be cleaved by (is cleavable by) a protease selected from: Caspase-3, Cathepsin B, CP, FAP, Kallikrein 2 (hK2), MMP-2, MMP-7, MMP-9, MMP-14, plasmin, PSA, TOP, uPA, Thrombin, Trypsin, uPA, and PRSS23.

Examples of proteases include, but are not limited to: alanine carboxypeptidase, Armillaria mellea astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, IgA-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase.

Thus, in some cases, the polypeptide linker comprises a target sequence for a protease (a 'protease cleavage site', a 'protease recognition sequence'), where the protease is selected from (i.e., where the cleavable linker is cleavable by): alanine carboxypeptidase, Armillaria mellea astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, IgA-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase.

In some cases, the linker is a cleavable polypeptide linker that can be cleaved by (is cleavable by) a viral, fungal, or bacterial protease. Examples of suitable viral and bacterial proteases include but are not limited to: (1) a Potyviridae protease (e.g., Tobacco Etch Virus (TEV) protease, a Turnip Mosaic Virus (TuMV) protease, Plum Pox Virus (PPV) protease, Potato virus Y (PVY) protease, Cassava brown streak virus (CBSV) protease, and the like); (2) a Picornaviridae protease (e.g., a Human rhinovirus protease such as PreScission protease (3C), and the like); (3) a Herpesviridae protease (e.g., a Epstein-Barr virus (EBV) protease—also called human herpesvirus 4, HHV-4—such as BVRF2, a Kaposi's sarcoma-associated herpesvirus (KSHV) protease—also called human herpesvirus 8, HHV-8, a Cytomegalovirus (CMV) protease—also called human herpesvirus 5, HHV-5—such as UL80 APNG, and the like); (4) a Flaviviridae protease (e.g., a Flavivirus protease, e.g., a Zika virus (ZV) protease, a Yellow fever virus (YFV) protease, a Dengue virus protease such as a DENV2 protease, a west nile virus (WNV) protease, a pestivirus protease, and the like, such as an NS3 protease, a NS2B/NS3pro protease, and the like); (5) a AvrPphB protease (e.g., a *P. syringae* pv. *phaseolicola* protease); (6) an AvrRpt2 protease (e.g., a *Pseudomonas syringae* pv. tomato protease); (7) a *Yersinia pestis* (plauge) protease (e.g., a yopT protease); (8) a Togaviridae protease (e.g., a alphavirus genus protease); and (9) a SARS virus protease such as a 3c-like endopeptidase.

Thus, in some cases, the linker is a cleavable polypeptide linker that can be cleaved by (is cleavable by) a viral or bacterial protease selected from: (1) a Potyviridae protease (e.g., Tobacco Etch Virus (TEV) protease, a Turnip Mosaic Virus (TuMV) protease, Plum Pox Virus (PPV) protease, Potato virus Y (PVY) protease, Cassava brown streak virus (CBSV) protease, and the like); (2) a Picornaviridae protease (e.g., a Human rhinovirus protease such as PreScission protease (3C), and the like); (3) a Herpesviridae protease (e.g., a Epstein-Barr virus (EBV) protease—also called human herpesvirus 4, HHV-4—such as BVRF2, a Kaposi's sarcoma-associated herpesvirus (KSHV) protease—also called human herpesvirus 8, HHV-8, a Cytomegalovirus (CMV) protease—also called human herpesvirus 5, HHV-5—such as UL80 APNG, and the like); (4) a Flaviviridae protease (e.g., a Flavivirus protease, e.g., a Zika virus (ZV) protease, a Yellow fever virus (YFV) protease, a Dengue virus protease such as a DENV2 protease, a West Nile virus (WNV) protease, a pestivirus protease, and the like, such as an NS3 protease, a NS2B/NS3pro protease, and the like); (5) a AvrPphB protease (e.g., a *P. syringae* pv. *phaseolicola* protease); (6) a AvrRpt2 protease (e.g., a *Pseudomonas syringae* pv. tomato protease); (7) a *Yersinia pestis* (plague) protease (e.g., a yopT protease); (8) a Togaviridae protease (e.g., a alphavirus genus protease); and (9) a SARS virus protease such as a 3c-like endopeptidase. In some cases, a subject circular permuted Cas9 protein includes a cleavable polypeptide linker that can be cleaved by (is cleavable by) a Tobacco Etch Virus (TEV) protease (e.g., in some cases the linker includes the sequence ENLYFQG (SEQ ID NO: 50).

Examples of cleavage sequences for various proteases include, but are not limited to: DDDDK (SEQ ID NO: 77), cleaved by enterokinase; LVPR (SEQ ID NO: 78), cleaved by thrombin; Val-Gly-Arg, cleaved by uPA and tPA; Pro-X-X-Hy (wherein, X represents an arbitrary residue; Hy, a hydrophobic residue), e.g., Pro-X-X-Hy-(Ser/Thr), e.g., Pro-Leu/Gln-Gly-Met-Thr-Ser (SEQ ID NO:74) or Pro-Leu/Gln-Gly-Met-Thr (SEQ ID NO:75), cleaved by MMP-9; SLLKSRMVPNFN (SEQ ID NO: 79) or SLLIARRMPNFN (SEQ ID NO: 80) cleaved by cathepsin B; SKLVQASASGVN (SEQ ID NO: 81) or SSYLKAS-DAPDN (SEQ ID NO: 82) cleaved by an Epstein-Barr virus protease; RPKPQQFFGLMN (SEQ ID NO: 83) cleaved by MMP-3 (stromelysin); SLRPLALWRSFN (SEQ ID NO: 84) cleaved by MMP-7 (matrilysin); SPQGIAGQRNFN (SEQ ID NO: 85) cleaved by MMP-9; DVDER-DVRGFASFL (SEQ ID NO: 86) cleaved by a thermolysin-like MMP; SLPLGLWAPNFN (SEQ ID NO: 87) cleaved by matrix metalloproteinase 2 (MMP-2); SLLIFRSWANFN (SEQ ID NO: 88) cleaved by cathespin L; SGVVIATVIVIT (SEQ ID NO: 89) cleaved by cathespin D; SLGPQGIWGQFN (SEQ ID NO: 90) cleaved by matrix metalloproteinase 1 (MMP-1); KKSPGRVVGGSV (SEQ ID NO: 91) cleaved by urokinase-type plasminogen activator; PQGLLGAPGILG (SEQ ID NO: 92) cleaved by membrane type 1 matrix metalloproteinase (MT-MMP); HGPEGLRVGFYESDVMGRGHARLVHVEEPHT (SEQ ID NO: 93) cleaved by stromelysin 3 (or MMP-11), thermolysin, fibroblast collagenase and stromelysin-1; GPQGLAGQRGIV (SEQ ID NO: 94) cleaved by matrix metalloproteinase 13 (collagenase-3); GGSGQRGRKALE (SEQ ID NO: 95) cleaved by tissue-type plasminogen activator (tPA); SLSALLSSDIFN (SEQ ID NO: 96) cleaved by human prostate-specific antigen; SLPRFKIIGGFN (SEQ ID NO: 97) cleaved by kallikrein (bK3): SLLGIAVPGNFN (SEQ ID NO: 98) cleaved by neutrophil elastase; FFKNIVT-PRTPP (SEQ ID NO: 99), cleaved by calpain (calcium activated neutral protease); LEVLFQGP (SEQ ID NO: 100), cleaved by PreScission protease (a fusion protein comprising human rhinovirus 3C protease and glutathione-S-transferase; Walker et al. (1994) Biotechnol. 12:601); and CGLVPAGSGP (SEQ ID NO: 101), cleaved by thrombin.

Amino acid sequences (target sequences) that can be cleaved by various proteases are known in the art and any convenient sequence can be used. Examples of such sequences include, but are not limited to those presented in Table 3.

TABLE 3

Examples cleavable amino acid sequences that can be included in a cleavable linker (that is cleavage by a viral protease) of a subject RNA-guided polypeptide (e.g., conditionally active RNA-guided polypeptide).

| Pathogen Family | Pathogen genus | Protease from | Example target sequence | SEQ ID NO: |
|---|---|---|---|---|
| Poty-virus | Poty-viridae | Tobacco Etch Virus (TEV) | ENLYFQ^G | 50 |
| | | | ENLYTQ^S | 76 |
| | | | ENLYFQSM | 102 |
| | | Turnip Mosaic Virus (TuMV) | EVVHQ^AK | 51 |
| | | | GGCSHQ^S | 52 |
| | | | AAVRHQ^S | 53 |
| | | Plum Pox Virus (PPV) | QVVVHQ^SK | 54 |
| | | | DVRHQ^RS | 55 |
| | | | VXHQ^S | 56 |
| | | Potato virus Y (PVY) | YDVRHQSR | 103 |
| | | Cassava brown streak virus (CBSV) protease | GLVEVQ^GR | 57 |
| | | Poty universal (consensus) | EGVGHQSK | 18 |
| | | Poty universal (consensus) | VGHQSVGHQS | 19 |
| Picorn-aviridae | Entero-virus | PreScission' (e.g., Human rhinovirus B14) | LEVLFQ^GP | 58 |
| Herpes-viridae | Lympho-crypto-virus | Epstein-Barr virus (EBV), also called human herpes-virus 4 (HHV-4) | KKLVQA^SAS | 59 |
| | | | YLKA^S | 60 |
| | Rhadino-virus | KSHV (HHV-8) | YLQA^S | 61 |
| | Cytomega-lovirus | CMV (HHV-5) | GVVN^ASCR | 62 |
| | | | YVKA^S | 63 |
| Flavivi-ridae | Flavi-virus | Zika virus (ZV) | KERKRR^GAD | 64 |
| | | | KERKRRGA | 104 |
| | | Yellow fever virus (YFV) | SSRKRR^SHD | 65 |
| | | | SSRKRRSH | 106 |
| | | | ARRR^SQ | 66 |
| | | Dengue (e.g., DENV2) | NRRRR^SAG | 67 |
| | | | LKRR^GG | 68 |
| | | | TTSTRR | 69 |
| | | Westnile virus (WNV) | SKQKKR^GGK | 70 |
| | | | LQYTKR^GG | 71 |
| | | | KQKKR^GG | 72 |
| | | | KQKKR^GGK | 105 |
| | | Flavi universal (consensus) | LKRR^SGS | 73 |

Cas9 Fusion Polypeptides (Internal Insertions)

A heterologous polypeptide (or heterologous amino acid such as a cysteine residue or a non-natural amino acid) can be inserted at several positions within a Cas9 polypeptide to generate a subject Cas9 fusion polypeptide. For example, by screening for circular permuted Cas9 proteins that retain target binding function, the inventors discovered several sites that tolerate insertions without substantially affecting the function of the Cas9 protein (e.g., without substantially affecting the cleaving of a target nucleic acid and/or the binding of a target nucleic acid). For example, a position that can be the sight of a circular permutation (such as those described above and in the Examples section below) can instead be the site for an internal insertion into the Cas9 protein without generating a circular permutant.

The present disclosure provides Cas9 fusion polypeptides that include one or more heterologous polypeptides inserted internally within a Cas9 protein at one or more internal insertion sites. In some embodiments, the heterologous amino acid or heterologous polypeptide is inserted at a position that is immediately adjacent and C-terminal to an amino acid residue corresponding to a residue selected from: 182, 200, 231, 271, 311, 1011, 1017, 1024, 1029, 1030, 1032, 1042, 1245, 1249, 1250, and 1283 (in some cases selected from the residues listed in Table 2), based on the numbering of the Cas9 protein set forth in SEQ ID NO: 111. In other words, in some cases, the heterologous amino acid or heterologous polypeptide is inserted at a position that is immediately adjacent and C-terminal to an amino acid residue corresponding to a residue selected from: 182D, 200P, 231G, 271Y, 311E, 1011G, 1017D, 1024K, 1029I, 1030G, 1032A, 1042I, 1245L, 1249P, 1250E, and 1283A (and in some cases the amino acid positions listed in Table 2) of the Cas9 protein set forth in SEQ ID NO: 111. If the Cas9 polypeptide is a protein other than the protein set forth as SEQ ID NO: 111 (e.g., any of the proteins set forth in SEQ ID NOs: 112-912, or any other Cas9 protein, of which many will be known to one of ordinary skill in the art), sequence alignments can be used to determine which amino acid 'corresponds' to the amino acid above. In other words, the amino acid positions listed above use the protein set forth in SEQ ID NO: 111 as the reference sequence, but any Cas9 protein can serve as the reference sequence and the 'corresponding' amino acid position can be readily determined, e.g., using a sequence and/or structural alignment.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to an amino acid residue corresponding to a residue selected from 182D, 200P, 231G, 271Y, 311E, 1011G, 1017D, 1024K, 1029I, 1030G, 1032A, 1042I, 1245L, 1249P, 1250E, and 1283A (and in some cases the amino acid positions listed in Table 2) of the protein set forth in SEQ ID NO: 111.

In some cases, a Cas9 fusion polypeptide of the present disclosure has 70% or more identity (e.g. 75% or more, 80% or more, 85% or more, 90% or more, 95% or more, 97% or more, 98% or more, 99% or more, or 100% identity) with the sequence set forth in any one of SEQ ID NOs: 17 and 111-912; and the heterologous amino acid or heterologous polypeptide is inserted at a position that is immediately adjacent and C-terminal to an amino acid residue corresponding to a residue selected from 182D, 200P, 231G, 271Y, 311E, 1011G, 1017D, 1024K, 1029I, 1030G, 1032A, 1042I, 1245L, 1249P, 1250E, and 1283A (and in some cases the amino acid positions listed in Table 2) of the protein set forth in SEQ ID NO: 111. For example, in some cases, a Cas9 fusion polypeptide of the present disclosure has 80% or more identity (e.g. 85% or more, 90% or more, 95% or more, 97% or more, 98% or more, 99% or more, or 100% identity) with the sequence set forth in any one of SEQ ID NOs: 17 and 111-912; and the heterologous amino acid or heterologous polypeptide is inserted at a position that is immediately adjacent and C-terminal to an amino acid residue corresponding to a residue selected from 182D, 200P, 231G, 271Y, 311E, 1011G, 1017D, 1024K, 1029I, 1030G, 1032A, 1042I, 1245L, 1249P, 1250E, and 1283A (and in some cases the amino acid positions listed in Table 2) of the protein set forth in SEQ ID NO: 111. In some cases, a Cas9 fusion polypeptide of the present disclosure has 85% or more identity (e.g. 90% or more, 95% or more, 97% or more, 98% or more, 99% or more, or 100% identity) with the sequence set forth in any one of SEQ ID NOs: 17 and 111-912; and the heterologous amino acid or heterologous polypeptide is inserted at a position that is immediately adjacent and C-terminal to an amino acid residue corresponding to a residue selected from 182D, 200P, 231G, 271Y, 311E, 1011G, 1017D, 1024K, 1029I, 1030G, 1032A, 1042I, 1245L, 1249P, 1250E, and 1283A (and in some cases the amino acid positions listed in Table 2) of the protein set forth in SEQ ID NO: 111.

In some cases, a Cas9 fusion polypeptide of the present disclosure includes an amino acid sequence having 4 motifs, each of motifs 1-4 having 60% or more amino acid sequence identity (e.g., 70% or more, 75% or more, 80% or more, 85% or more, 90% or more, 95% or more, 99% or more or 100% amino acid sequence identity) to motifs 1-4 set forth in SEQ ID NOs: 37-40, respectively, as depicted in Table 1, or to the corresponding portions in any of the amino acid sequences set forth in SEQ ID NOs: 111-912; and the heterologous amino acid or heterologous polypeptide is inserted at a position that is immediately adjacent and C-terminal to an amino acid residue corresponding to a residue selected from 182D, 200P, 231G, 271Y, 311E, 1011G, 1017D, 1024K, 1029I, 1030G, 1032A, 1042I, 1245L, 1249P, 1250E, and 1283A (and in some cases the amino acid positions listed in Table 2) of the protein set forth in SEQ ID NO: 111. In some cases, a Cas9 fusion polypeptide of the present disclosure includes an amino acid sequence having 4 motifs, each of motifs 1-4 having 80% or more amino acid sequence identity (e.g., 85% or more, 90% or more, 95% or more, 99% or more or 100% amino acid sequence identity) to motifs 1-4 set forth in SEQ ID NOs: 37-40, respectively, as depicted in Table 1, or to the corresponding portions in any of the amino acid sequences set forth in SEQ ID NOs: 111-912; and the heterologous amino acid or heterologous polypeptide is inserted at a position that is immediately adjacent and C-terminal to an amino acid residue corresponding to a residue selected from 182D, 200P, 231G, 271Y, 311E, 1011G, 1017D, 1024K, 1029I, 1030G, 1032A, 1042I, 1245L, 1249P, 1250E, and 1283A (and in some cases the amino acid positions listed in Table 2) of the protein set forth in SEQ ID NO: 111. In some cases, a Cas9 fusion polypeptide of the present disclosure includes an amino acid sequence having 4 motifs, each of motifs 1-4 having 90% or more amino acid sequence identity (e.g., 95% or more, 99% or more or 100% amino acid sequence identity) to motifs 1-4 set forth in SEQ ID NOs: 37-40, respectively, as depicted in Table 1, or to the corresponding portions in any of the amino acid sequences set forth in SEQ ID NOs: 111-912; and the heterologous amino acid or heterologous polypeptide is inserted at a position that is immediately adjacent and C-terminal to an amino acid residue corresponding to a residue selected from 182D, 200P, 231G, 271Y, 311E, 1011G, 1017D, 1024K, 1029I, 1030G, 1032A, 1042I, 1245L, 1249P, 1250E, and 1283A (and in some cases the amino acid positions listed in Table 2) of the protein set forth in SEQ ID NO: 111.

In some cases, a Cas9 fusion polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 182D of the protein set forth in SEQ ID NO: 111. In some cases, the heterologous amino acid or heterologous polypeptide is inserted at a position that is immediately adjacent and C-terminal to an amino acid residue corresponding to amino acid 200P of the protein set forth in SEQ ID NO: 111. In some cases, the heterologous amino acid or heterologous polypeptide is inserted at a position that is immediately adjacent and C-terminal to an amino acid residue corresponding to amino acid 231G of the protein set forth in SEQ ID NO: 111. In some cases, the heterologous amino acid or heterologous polypeptide is inserted at a position that is immediately adjacent and C-terminal to an amino acid residue corresponding to amino acid 271Y of the protein set forth in SEQ ID NO: 111. In some cases, the heterologous amino acid or heterologous polypeptide is inserted at a position that is immediately adjacent and C-terminal to an amino acid residue corresponding to amino acid 311E of the protein set forth in SEQ ID NO: 111. In some cases, the heterologous amino acid or heterologous polypeptide is inserted at a position that is immediately adjacent and C-terminal to an amino acid residue corresponding to amino acid 1011G of the protein set forth in SEQ ID NO: 111. In some cases, the heterologous amino acid or heterologous polypeptide is inserted at a position that is immediately adjacent and C-terminal to an amino acid residue corresponding to amino acid 1017D of the protein set forth in SEQ ID NO: 111. In some cases, the heterologous amino acid or heterologous polypeptide is inserted at a position that is immediately adjacent and C-terminal to an amino acid residue corresponding to amino acid 1024K of the protein set forth in SEQ ID NO: 111. In some cases, the heterologous amino acid or heterologous polypeptide is inserted at a position that is immediately adjacent and C-terminal to an amino acid residue corresponding to amino acid 1029I of the protein set forth in SEQ ID NO: 111. In some cases, the heterologous amino acid or heterologous polypeptide is inserted at a position that is immediately adjacent and C-terminal to an amino acid residue corresponding to amino acid 1030G of the protein set forth in SEQ ID NO: 111. In some cases, the heterologous amino acid or heterologous polypeptide is inserted at a position that is immediately adjacent and C-terminal to an amino acid residue corresponding to amino acid 1032A of the protein set forth in SEQ ID NO: 111. In some cases, the Cas9 polypeptide, where the heterologous amino acid or heterologous polypeptide is inserted at a position that is immediately adjacent and C-terminal to an amino acid residue corresponding to amino acid 1042I of the protein set forth in SEQ ID NO: 111. In some cases, the heterologous amino acid or heterologous polypeptide is inserted at a position that is immediately adjacent and C-terminal to an amino acid residue corresponding to amino acid 1245L of the protein set forth in SEQ ID NO: 111. In some cases, the heterologous amino acid or heterologous polypeptide is inserted at a position that is immediately adjacent and C-terminal to an amino acid residue corresponding to amino acid 1249P of the protein set forth in SEQ ID NO: 111. In some cases, the heterologous amino acid or heterologous polypeptide is inserted at a position that is immediately adjacent and C-terminal to an amino acid residue corresponding to amino acid 1250E of the protein set forth in SEQ ID NO: 111. In some cases, the heterologous amino acid or heterologous polypeptide is inserted at a position that is immediately adjacent and C-terminal to an amino acid residue corresponding to amino acid 1283 of the protein set forth in SEQ ID NO: 111. In some cases, the heterologous amino acid or heterologous polypeptide is inserted at a position that is immediately adjacent and C-terminal to an amino acid residue corresponding to amino acid positions listed in Table 2 of the protein set forth in SEQ ID NO: 111.

The Cas9 fusion polypeptide retains at least some RNA guided sequence specific target DNA binding activity. In some cases, the Cas9 fusion polypeptide retains (has) activity (e.g., cleavage and/or binding activity) relative to the activity of the Cas9 polypeptide without the inserted heterologous amino acid or heterologous polypeptide, where the Cas9 polypeptide without the inserted heterologous amino acid or heterologous polypeptide is also referred to as the "parent Cas9 polypeptide." For example, in some cases, the Cas9 fusion polypeptide has (retains) 50% or more of the activity (e.g., cleavage and/or binding activity) of the corresponding parent Cas9 polypeptide (the Cas9 polypeptide that does not have the insertion). For example, in some cases, the Cas9 fusion polypeptide has (retains) 60% or more (70% or more, 80% or more, 90% or more, 92% or more, 95% or more, 98% or more, or 100%) of the activity (e.g., cleavage and/or binding activity) of the corresponding parent Cas9 polypeptide (the Cas9 polypeptide that does not have the insertion).

In some cases, the Cas9 fusion polypeptide retains (has) target nucleic acid binding activity relative to the activity of the Cas9 polypeptide without the inserted heterologous amino acid or heterologous polypeptide. For example, in some cases, the Cas9 fusion polypeptide has (retains) 50% or more of the binding activity of the corresponding Cas9 polypeptide (the Cas9 polypeptide that does not have the insertion). For example, in some cases, the Cas9 fusion polypeptide has (retains) 60% or more (70% or more, 80% or more, 90% or more, 92% or more, 95% or more, 98% or more, or 100%) of the binding activity of the corresponding Cas9 polypeptide (the Cas9 polypeptide that does not have the insertion).

In some cases, the Cas9 fusion polypeptide retains (has) target nucleic acid binding and/or cleavage activity relative to the activity of the Cas9 polypeptide without the inserted heterologous amino acid or heterologous polypeptide. For example, in some cases, the Cas9 fusion polypeptide has (retains) 50% or more of the binding and/or cleavage activity of the corresponding Cas9 polypeptide (the Cas9 polypeptide that does not have the insertion). For example, in some cases, the Cas9 fusion polypeptide has (retains) 60% or more (70% or more, 80% or more, 90% or more, 92% or more, 95% or more, 98% or more, or 100%) of the binding and/or cleavage activity of the corresponding Cas9 polypeptide (the Cas9 polypeptide that does not have the insertion). Methods of measuring cleaving and/or binding activity of a Cas9 polypeptide and/or a Cas9 fusion polypeptide will be known to one of ordinary skill in the art and any convenient method can be used.

Heterologous Polypeptides

A variety of heterologous polypeptides are suitable for inclusion in a subject RNA-guided polypeptide (e.g., a circular permuted Cas9 protein, e.g., conditionally active circular permuted Cas9 protein) and/or a subject Cas9 fusion polypeptide of the present disclosure. In some embodiments, the heterologous polypeptide is fused to one or more internal portions (i.e., a portion other than the N- or C-terminus) of the protein. In some embodiments, a heterologous polypeptide is fused to the C-terminus of a subject RNA-guided polypeptide and/or a subject Cas9 fusion polypeptide. In some embodiments, a heterologous polypeptide is fused to the N-terminus of a subject RNA-guided polypeptide and/or a subject Cas9 fusion polypeptide. In some embodiments, a heterologous polypeptide is fused to the N-terminus of a subject RNA-guided polypeptide and/or a subject Cas9 fusion polypeptide, and a heterologous polypeptide is fused to the C-terminus of a subject RNA-guided polypeptide and/or a subject Cas9 fusion polypeptide.

An RNA-guided polypeptide (e.g., a circular permuted Cas9 protein) and/or a Cas9 fusion polypeptide of the present disclosure can contain any convenient number of heterologous polypeptides at one or more insertion sites (include the N- and/or C-termini) Thus, the subject RNA-guided polypeptide (e.g., a circular permuted Cas9 protein) and/or a subject Cas9 fusion polypeptide can contain one or more, e.g., 2 or more, 3 or more, 4 or more, 5 or more, 7 or more, including 10 or more heterologous polypeptides, and can contain 15 or fewer, e.g., 12 or fewer, 10 or fewer, 8 or fewer, 6 or fewer, 4 or fewer, 3 or fewer, including 2 or fewer distinct heterologous polypeptides. In some cases, the subject RNA-guided polypeptide (e.g., a circular permuted Cas9 protein) and/or a subject Cas9 fusion polypeptide contains between 1 to 10, e.g., between 1 to 8, between 1 to 5, between 1 to 4, between 1 to 3, including between 1 to 2 heterologous polypeptides. Where the subject RNA-guided polypeptide (e.g., a circular permuted Cas9 protein) and/or a subject Cas9 fusion polypeptide contains more than one heterologous polypeptide, any two of the heterologous polypeptides may be the same or may be distinct heterologous polypeptides. In some cases, a subject Cas9 fusion polypeptide of the present disclosure comprises a single heterologous polypeptide inserted at a site internal to the Cas9 polypeptide. In some cases, a Cas9 fusion polypeptide of the present disclosure comprises 2 heterologous polypeptides inserted at two different sites internal to the Cas9 polypeptide.

For a subject RNA-guided polypeptide (e.g., a circular permuted Cas9 protein, e.g., conditionally active RNA-guided polypeptide), a heterologous polypeptide (fusion partner) can be fused to the N-terminus, the C-terminus, or both. In some cases, a heterologous polypeptide (fusion partner) can be fused internally to a subject RNA-guided polypeptide (e.g., a circular permuted Cas9 protein).

A heterologous polypeptide to which a subject RNA-guided polypeptide (e.g., a circular permuted Cas9 protein, e.g., conditionally active RNA-guided polypeptide) and/or subject Cas9 fusion polypeptide can be fused is referred to herein as a 'fusion partner.'

In some cases the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a fusion partner has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a fusion partner has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used as a fusion partner to increase transcription include but are not limited to: transcriptional activators such as VP16, VP64, VP48, VP160, p65 subdomain (e.g., from NFkB), and activation domain of EDLL and/or TAL acitvation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used as a fusion partner to decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme, e.g., an APOBEC protein such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, a protein of the present disclosure (e.g., a subject RNA-guided polypeptide, e.g., a conditionally active RNA-guided polypeptide, a circular permuted Cas9 protein, a subject Cas9 fusion polypeptide, and the like) is fused to a polypeptide selected from: a domain for increasing transcription (e.g., a VP16 domain, a VP64 domain), a domain for decreasing transcription (e.g., a KRAB domain, e.g., from the Kox1 protein), a core catalytic domain of a histone acetyltransferase (e.g., histone acetyltransferase p300), a protein/domain that provides a detectable signal (e.g., a fluorescent protein such as GFP), a nuclease domain (e.g., a FokI nuclease), and a base editor (e.g., cytidine deaminase such as APOBEC1).

In some cases the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of a suitable fusion partners are (i) a dihydrofolate reductase (DHFR) destabilization domain (e.g., to generate a chemically controllable subject RNA-guided polypeptide, e.g., a circular permuted Cas9 protein, e.g., conditionally active RNA-guided polypeptide, and/or subject Cas9 fusion polypeptide), and (ii) a chloroplast transit peptide. Suitable chloroplast transit peptides include, but are not limited to:

(SEQ ID NO: 913)
MASMISSSAVTTVSRASRGQSAAMAPFGGLKSMTGFPVRKVNTDITS

ITSNGGRVKCMQVWPPIGKKKFETLSYLPPLTRDSRA;

(SEQ ID NO: 914)
MASMISSSAVTTVSRASRGQSAAMAPFGGLKSMTGFPVRKVNTDITS

ITSNGGRVKS;

(SEQ ID NO: 915)
MASSMLSSATMVASPAQATMVAPFNGLKSSAAFPATRKANNDITSIT

SNGGRVNCMQVWPPIEKKKFETLSYLPDLTDSGGRVNC;

(SEQ ID NO: 916)
MAQVSRICNGVQNPSLISNLSKSSQRKSPLSVSLKTQQHPRAYPISS

SWGLKKSGMTLIGSELRPLKVMSSVSTAC;

(SEQ ID NO: 917)
MAQVSRICNGVWNPSLISNLSKSSQRKSPLSVSLKTQQHPRAYPISS

SWGLKKSGMTLIGSELRPLKVMSSVSTAC;

(SEQ ID NO: 918)
MAQINNMAQGIQTLNPNSNFHKPQVPKSSSFLVFGSKKLKNSANSML

VLKKDSIFMQLFCSFRISASVATAC;

(SEQ ID NO: 919)
MAALVTSQLATSGTVLSVTDRFRRPGFQGLRPRNPADAALGMRTVGA

SAAPKQSRKPHRFDRRCLSMVV;

(SEQ ID NO: 920)
MAALTTSQLATSATGFGIADRSAPSSLLRHGFQGLKPRSPAGGDATS

LSVTTSARATPKQQRSVQRGSRRFPSVVVC;

(SEQ ID NO: 921)
MASSVLSSAAVATRSNVAQANMVAPFTGLKSAASFPVSRKQNLDITS

IASNGGRVQC;

(SEQ ID NO: 922)
MESLAATSVFAPSRVAVPAARALVRAGTVVPTRRTSSTSGTSGVKCS

AAVTPQASPVISRSAAAA;
and (SEQ ID NO: 923)
MGAAATSMQSLKFSNRLVPPSRRLSPVPNNVTCNNLPKSAAPVRTVK

CCASSWNSTINGAAATTNGASAASS.

In some cases, a subject RNA-guided polypeptide (e.g., a circular permuted Cas9 protein, e.g., conditionally active RNA-guided polypeptide) and/or subject Cas9 fusion polypeptide of the present disclosure can include an endosomal escape peptide. In some cases, an endosomal escape polypeptide comprises the amino acid sequence GLFX-ALLXLLXSLWXLLLXA (SEQ ID NO: 924), wherein each X is independently selected from lysine, histidine, and arginine. In some cases, an endosomal escape polypeptide comprises the amino acid sequence GLF-HALLHLLHSLWHLLLHA (SEQ ID NO: 925).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al., J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et al., Cell. 2013 Jul. 18; 154(2):442-51; Kearns et al., Nat Methods. 2015 May; 12(5):401-3; Mendenhall et al., Nat Biotechnol. 2013 December; 31(12):1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA. 2003 Jul. 22; 100(15):8688-91; Tan et al., J Virol. 2006 February; 80(4):1939-48; Tan et al., Proc Natl Acad Sci USA. 2003 Oct. 14; 100(21):11997-2002; Papworth et al., Proc Natl Acad Sci USA. 2003 Feb. 18; 100(4):1621-6; Sanjana et al., Nat Protoc. 2012 Jan. 5; 7(1):171-92; Beerli et al., Proc Natl Acad Sci USA. 1998 Dec. 8; 95(25):14628-33; Snowden et al., Curr Biol. 2002 Dec. 23; 12(24):2159-66; Xu et al., Cell Discov. 2016 May 3; 2:16009; Komor et al., Nature. 2016 Apr. 20; 533(7603): 420-4; Chaikind et al., Nucleic Acids Res. 2016 Aug. 11; Choudhury et al., Oncotarget. 2016 Jun. 23; Du et al., Cold Spring Harb Protoc. 2016 Jan. 4; Pham et al., Methods Mol Biol. 2016; 1358:43-57; Balboa et al., Stem Cell Reports. 2015 Sep. 8; 5(3):448-59; Hara et al., Sci Rep. 2015 Jun. 9; 5:11221; Piatek et al., Plant Biotechnol J. 2015 May; 13(4): 578-89; Hu et al., Nucleic Acids Res. 2014 April; 42(7): 4375-90; Cheng et al., Cell Res. 2013 October; 23(10):1163-71; and Maeder et al., Nat Methods. 2013 October; 10(10): 977-9.

Non-limiting examples of fusion partners for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

A fusion partner can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP 51, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyade-nylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as a fusion partner have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.).

Examples of various suitable fusion partners include, but are not limited to those described in the following patents and applications (which disclose Cas9 proteins fused with various fusion partners): PCT patent applications: WO2010075303, WO2012068627, and WO2013155555; U.S. Pat. Nos. 8,906,616; 8,895,308; 8,889,418; 8,889,356; 8,871,445; 8,865,406; 8,795,965; 8,771,945; and 8,697,359; and U.S. patent applications: 20160304846, 20160215276, 20150166980, 20150071898, 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a subject RNA-guided polypeptide (e.g., a circular permuted Cas9 protein, e.g., conditionally active RNA-guided polypeptide) and/or subject Cas9 fusion polypeptide does not include a NLS so that the protein is not targeted to the nucleus (which can be advantageous, e.g., when the target nucleic acid is an RNA that is present in the cyosol). In some embodiments, a fusion partner can provide a tag (i.e., the heterologous polypeptide is a detectable label) for ease of tracking and/or purification (e.g., a fluorescent protein, e.g., green fluorescent protein (GFP), yellow fluorescent protein (YFP), red fluorescent protein (RFP), cyan fluorescent protein (CFP), mCherry, tdTomato, and the like; a histidine tag, e.g., a 6×His tag; a hemagglutinin (HA) tag; a FLAG tag; a Myc tag; and the like).

In some cases a subject RNA-guided polypeptide (e.g., a circular permuted Cas9 protein, e.g., conditionally active RNA-guided polypeptide) and/or subject Cas9 fusion polypeptide includes (is fused to) a nuclear localization signal (NLS) (e.g., in some cases 2 or more, 3 or more, 4 or more, or 5 or more NLSs). Thus, in some cases, a subject RNA-guided polypeptide (e.g., a circular permuted Cas9 protein, e.g., conditionally active RNA-guided polypeptide) and/or subject Cas9 fusion polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a subject RNA-guided polypeptide (e.g., a circular permuted Cas9 protein, e.g., conditionally active RNA-guided polypeptide) and/or subject Cas9 fusion polypeptide includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a subject RNA-guided polypeptide (e.g., a circular permuted Cas9 protein, e.g., conditionally active RNA-guided polypeptide) and/or subject Cas9 fusion polypeptide includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 926); the NLS from nucleoplasmin (e.g., the nucleoplasmin bipartite NLS with the sequence KRPAATKKAGQAKKKK (SEQ ID NO: 927)); the c-myc NLS having the amino acid sequence PAAKRVKLD (SEQ ID NO: 928) or RQRRNELKRSP (SEQ ID NO: 929); the hRNPA1 M9 NLS having the sequence NQSSNFGPMKGGNFGGRSSGPYGGGGQYFAKPRNQGGY (SEQ ID NO: 930); the sequence RMRIZFKNKGKDTAELRRRRVEVSVELRKAKKDEQILKRRNV (SEQ ID NO: 931) of the IBB domain from importin-alpha; the sequences VSRKRPRP (SEQ ID NO: 932) and PPKKARED (SEQ ID NO: 933) of the myoma T protein; the sequence PQPKKKPL (SEQ ID NO: 934) of human p53; the sequence SALIKKKKKMAP (SEQ ID NO: 935) of mouse c-abl IV; the sequences DRLRR (SEQ ID NO: 936) and PKQKKRK (SEQ ID NO: 937) of the influenza virus NS1; the sequence RKLKKKIKKL (SEQ ID NO: 938) of the Hepatitis virus delta antigen; the sequence REKKKFLKRR (SEQ ID NO: 939) of the mouse Mx1 protein; the sequence KRKGDEVDGVDEVAKKKSKK (SEQ ID NO: 940) of the human poly(ADP-ribose) polymerase; and the sequence RKCLQAGMNLEARKTKK (SEQ ID NO: 941) of the steroid hormone receptors (human) glucocorticoid. In general, NLS (or multiple NLSs) are of sufficient strength to drive accumulation of a subject RNA-guided polypeptide (e.g., a circular permuted Cas9 protein, e.g., conditionally active RNA-guided polypeptide) and/or subject Cas9 fusion polypeptide in a detectable amount in the nucleus of a eukaryotic cell. Detection of accumulation in the nucleus may be performed by any suitable technique. For example, a detectable marker may be fused to a subject RNA-guided polypeptide (e.g., a circular permuted Cas9 protein, e.g., conditionally active RNA-guided polypeptide) and/or subject Cas9 fusion polypeptide such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a subject RNA-guided polypeptide (e.g., a circular permuted Cas9 protein, e.g., conditionally active RNA-guided polypeptide) and/or subject Cas9 fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus of a subject RNA-guided polypeptide (e.g., a circular permuted Cas9 protein, e.g., conditionally active RNA-guided polypeptide) and/or subject Cas9 fusion polypeptide. In some embodiments, a PTD is covalently linked to the carboxyl terminus of a subject RNA-guided polypeptide (e.g., a circular permuted Cas9 protein, e.g., conditionally active RNA-guided polypeptide) and/or subject Cas9 fusion polypeptide. In some cases, the PTD is inserted internally in the subject RNA-guided polypeptide (e.g., a circular permuted Cas9 protein, e.g., conditionally active RNA-guided polypeptide) and/or subject Cas9 fusion polypeptide at a suitable insertion site. In some cases, a subject RNA-guided polypeptide (e.g., a circular permuted Cas9 protein, e.g., conditionally active RNA-guided polypeptide) and/or subject Cas9 fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a subject RNA-guided polypeptide (e.g., a circular permuted Cas9 protein, e.g., conditionally active RNA-guided polypeptide) and/or subject Cas9 fusion polypeptide includes one or more NLSs (e.g., 2 or more, 3 or more, 4 or more, or 5 or more NLSs). Examples of PTDs include but are not limited to a minimal undecapeptide protein transduction domain (corresponding to residues 47-57 of HIV-1 TAT comprising YGRKKRRQRRR; SEQ ID NO: 942); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO: 943); Transportan GWTLNSAGYLLGKINLKALAALAKKIL (SEQ ID NO: 944); KALAWEAKLAKALAKA-LAKHLAKALAKALKCEA (SEQ ID NO: 945); and RQIKIWFQNRRMKWKK (SEQ ID NO: 946). Exemplary PTDs include but are not limited to, YGRKKRRQRRR (SEQ ID NO: 947), RKKRRQRRR (SEQ ID NO: 948); an arginine homopolymer of from 3 arginine residues to 50 arginine residues; Exemplary PTD domain amino acid sequences include, but are not limited to, any of the following: YGRKKRRQRRR (SEQ ID NO: 949); RKKRRQRRR (SEQ ID NO: 950); YARAAARQARA (SEQ ID NO: 951); THRLPRRRRRR (SEQ ID NO: 952); and GGR-RARRRRRR (SEQ ID NO: 953). In some embodiments, the PTD is an activatable CPP (ACPP) (Aguilera et al. (2009) *Integr Biol* (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers

In some embodiments, a subject Cas9 fusion polypeptide can include a Cas9 polypeptide that is linked to an internally inserted heterologous amino acid or heterologous polypeptide (a heterologous amino acid sequence) via a linker polypeptide (e.g., one or more linker polypeptides). In some embodiments, a subject RNA-guided polypeptide (e.g., a circular permuted Cas9 protein, e.g., conditionally active RNA-guided polypeptide) can be linked at the C-terminal and/or N-terminal end to a heterologous polypeptide (fusion partner) via a linker polypeptide (e.g., one or more linker polypeptides) [e.g., in addition to the linker connecting the N-terminal fragment of the parent protein to the C-terminal fragment].

The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers are generally produced by using synthetic, linker-encoding oligonucleotides to couple the proteins. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Example linker polypeptides include glycine polymers $(G)_n$, glycine-serine polymers (including, for example, (GS)$_n$, GSGGS$_n$ (SEQ ID NO: 45), GGSGGS$_n$ (SEQ ID NO: 46), and GGGS$_n$ (SEQ ID NO: 47), where n is an integer of at least one), glycine-alanine polymers, alanine-serine polymers. Example linkers can comprise amino acid sequences including, but not limited to, GGSG (SEQ ID NO: 48), GGSGG (SEQ ID NO: 41), GSGSG (SEQ ID NO: 49), GSGGG (SEQ ID NO: 108), GGGSG (SEQ ID NO: 109), GSSSG (SEQ ID NO: 110), and the like. The ordinarily skilled artisan will recognize that design of a peptide conjugated to any elements described above can include linkers that are all or partially flexible, such that the linker can include a flexible linker as well as one or more portions that confer less flexible structure.

Cas9 Guide RNA

A nucleic acid molecule that binds to a CRISPR/Cas protein (e.g., a Cas9 protein) and targets the complex to a specific location within a target nucleic acid is referred to herein as a "guide RNA". When the guide RNA is for a Cas9 protein, e.g., a subject Cas9 fusion polypeptide, it is referred to as a "Cas9 guide RNA." When the parent RNA-guided polypeptide of a subject RNA-guided polypeptide (e.g., a circular permutant) is a Cas9 protein (i.e., when the subject RNA-guided polypeptide is a circular permuted Cas9 protein), a Cas9 guide RNA can be used to guide the protein to the target sequence.

A Cas9 guide RNA can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid.

A Cas9 guide RNA and a Cas9 protein, e.g., a fusion Cas9 polypeptide, form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein, e.g., a fusion Cas9 polypeptide, to any desired sequence of any desired target nucleic acid, with the exception (e.g., as described herein) that the PAM sequence can be taken into account. Thus, for example, a Cas9 guide RNA can have a targeting segment with a sequence that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a subject Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA." In some cases, a guide RNA can include one or more DNA nucleotides, but the term "guide RNA" as used herein is meant to encompass such hybrid molecules.

A Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

Targeting Segment of a Cas9 Guide RNA

The first segment of a subject guide nucleic acid includes a guide sequence (i.e., a targeting sequence)(a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 17 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the guide sequence can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the guide sequence has a length of from 15 nt to 30 nt. In some cases, the guide sequence has a length of from 15 nt to 25 nt. In some cases, the guide sequence has a length of from 17 nt to 30 nt. In some cases, the guide sequence has a length of from 17 nt to 25 nt. In some cases, the guide sequence has a length of from 17 nt to 22 nt In some cases, the guide sequence has a length of from 18 nt to 22 nt.

The percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Protein-Binding Segment of a Cas9 Guide RNA

The protein-binding segment of a subject Cas9 guide RNA interacts with a Cas9 protein. The Cas9 guide RNA guides the bound Cas9 protein to a specific nucleotide sequence within target nucleic acid via the above mentioned targeting segment. The protein-binding segment of a Cas9 guide RNA comprises two stretches of nucleotides that are complementary to one another and hybridize to form a double stranded RNA duplex (dsRNA duplex). Thus, the protein-binding segment includes a dsRNA duplex. In some cases, the protein-binding segment also includes stem loop 1 (the "*nexus*") of a Cas9 guide RNA. For example, in some cases, the activator of a Cas9 guide RNA (dgRNA or sgRNA) includes (i) a duplex forming segment that contributes to the dsRNA duplex of the protein-binding segment; and (ii) nucleotides 3' of the duplex forming segment, e.g., that form stem loop 1 (the "*nexus*"). For example, in some cases, the protein-binding segment includes stem loop 1 (the "*nexus*") of a Cas9 guide RNA. In some cases, the protein-binding segment includes 5 or more nucleotides (nt) (e.g., 6 or more, 7 or more, 8 or more, 9 or more, 10 or more, 11 or more, 12 or more, 15 or more, 20 or more, 30 or more, 40 or more, 50 or more, 60 or more, 70 or more, 75 or more, or 80 or more nt) 3' of the dsRNA duplex (where 3' is relative to the duplex-forming segment of the activator sequence).

The dsRNA duplex of the guide RNA (sgRNA or dgRNA) that forms between the activator and targeter is sometimes referred to herein as the "stem loop". In addition, the activator (activator RNA, tracrRNA) of many naturally existing Cas9 guide RNAs (e.g., *S. pyogenes* guide RNAs) has 3 stem loops (3 hairpins) that are 3' of the duplex-forming segment of the activator. The closest stem loop to the duplex-forming segment of the activator (3' of the duplex forming segment) is called "stem loop 1" (and is also referred to herein as the "*nexus*"); the next stem loop is called "stem loop 2" (and is also referred to herein as the "hairpin 1"); and the next stem loop is called "stem loop 3" (and is also referred to herein as the "hairpin 2").

In some cases, a Cas9 guide RNA (sgRNA or dgRNA) (e.g., a full length Cas9 guide RNA) has stem loops 1, 2, and 3. In some cases, an activator (of a Cas9 guide RNA) has stem loop 1, but does not have stem loop 2 and does not have stem loop 3. In some cases, an activator (of a Cas9 guide RNA) has stem loop 1 and stem loop 2, but does not have stem loop 3. In some cases, an activator (of a Cas9 guide RNA) has stem loops 1, 2, and 3.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the additional nucleotides 3' of the duplex forming segment form stem loop 1. In some cases, the activator (e.g., tracr sequence) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment. In some cases, the activator (activator RNA) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the stretch of nucleotides 3' of the duplex forming segment has a length in a range of from 5 to 200 nucleotides (nt) (e.g., from 5 to 150 nt, from 5 to 130 nt, from 5 to 120 nt, from 5 to 100 nt, from 5 to 80 nt, from 10 to 200 nt, from 10 to 150 nt, from 10 to 130 nt, from 10 to 120 nt, from 10 to 100 nt, from 10 to 80 nt, from 12 to 200 nt, from 12 to 150 nt, from 12 to 130 nt, from 12 to 120 nt, from 12 to 100 nt, from 12 to 80 nt, from 15 to 200 nt, from 15 to 150 nt, from 15 to 130 nt, from 15 to 120 nt, from 15 to 100 nt, from 15 to 80 nt, from 20 to 200 nt, from 20 to 150 nt, from 20 to 130 nt, from 20 to 120 nt, from 20 to 100 nt, from 20 to 80 nt, from 30 to 200 nt, from 30 to 150 nt, from 30 to 130 nt, from 30 to 120 nt, from 30 to 100 nt, or from 30 to 80 nt). In some cases, the nucleotides of the 3' tail of an activator RNA are wild type sequences. Although a number of different alternative sequences can be used, an example Cas9 single guide RNA (based on crRNA and tracrRNA from *S. pyogenes*, where the dsRNA duplex of the protein-binding segment is truncated relative to the dsRNA duplex present in the wild type dual guide RNA) can include the sequence set forth in SEQ ID NO: 958 (This example sequence does not include the guide sequence. The guide sequence, which varies depending on the target, would be 5' of this example sequence. The activator in this example is 66 nucleotides long).

Additional Resources

More information (including examples) related to various Cas9 guide RNAs, Cas9 proteins, and Cas9 PAMs can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al., Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20160304846, 20160215276, 20150166980, 20150071898, 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233;

20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Nucleic Acids

The present disclosure provides a nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like). The present disclosure provides a nucleic acid/protein complex comprising: a) an RNA-guided polypeptide (e.g., a circular permuted Cas9 protein, a conditionally active circular permuted Cas9 protein, and the like) of the present disclosure; and b) a guide RNA. The present disclosure provides a nucleic acid/protein complex comprising: a) a fusion Cas9 polypeptide of the present disclosure; and b) a guide RNA.

The present disclosure provides one or more nucleic acids (e.g., RNA and/or DNA) comprising one or more of: a donor polynucleotide sequence, a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like), a Cas9 guide RNA (which can include two separate nucleotide sequences in the case of dual guide RNA format or which can include a single nucleotide sequence in the case of single guide RNA format), and a nucleotide sequence encoding a Cas9 guide RNA.

The present disclosure provides a nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like). The present disclosure provides a recombinant expression vector that comprises a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like). The present disclosure provides a recombinant expression vector that comprises a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like). The present disclosure provides a recombinant expression vector that comprises: a) a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like); and b) a nucleotide sequence encoding a Cas9 guide RNA(s). The present disclosure provides a recombinant expression vector that comprises: a) a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like); and b) a nucleotide sequence encoding a Cas9 guide RNA(s). In some cases, the nucleotide sequence encoding the protein of the present disclosure (e.g., a subject RNA-guided polypeptide, e.g., a conditionally active RNA-guided polypeptide, a circular permuted Cas9 protein, a subject Cas9 fusion polypeptide, and the like) and/or the nucleotide sequence encoding the Cas9 guide RNA is operably linked to a promoter that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding an RNA-guided polypeptide (e.g., a circular permuted Cas9 protein) and/or a Cas9 fusion polypeptide of the present disclosure is codon optimized. This type of optimization can entail a mutation of a protein-coding (e.g., Cas9-encoding) nucleotide sequence to mimic the codon preferences of the intended host organism or cell while encoding the same protein. Thus, the codons can be changed, but the encoded protein remains unchanged. For example, if the intended target cell was a human cell, a human codon-optimized protein-encoding (e.g., Cas9-encoding) nucleotide sequence could be used. As another non-limiting example, if the intended host cell were a mouse cell, then a mouse codon-optimized protein-encoding (e.g., Cas9-encoding) nucleotide sequence could be generated. As another non-limiting example, if the intended host cell were a plant cell, then a plant codon-optimized protein-encoding (e.g., Cas9-encoding) nucleotide sequence could be generated. As another non-limiting example, if the intended host cell were an insect cell, then an insect codon-optimized protein-encoding (e.g., Cas9-encoding) nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a Cas9 guide RNA that hybridizes to a target sequence of the target locus of the targeted genome (e.g., a single or dual guide RNA) (e.g., operably linked to a promoter that is operable in a target cell such as a eukaryotic cell); and (iii) a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a Cas9 guide RNA that hybridizes to a target sequence of the target locus of the targeted genome (e.g., a single or dual guide RNA) (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a Cas9 guide RNA that hybridizes to a target sequence of the target locus of the targeted genome (e.g., a single or dual guide RNA) (e.g., operably linked to a promoter that is operable in a target cell such as a eukaryotic cell); and (ii) a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a Cas9 guide RNA is operably linked to a control element, e.g., a transcriptional control element, such as a promoter. In some embodiments, a nucleotide sequence encoding an RNA-guided polypeptide (e.g., a circular permuted Cas9 protein) or a Cas9 fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to a subject protein, thus resulting in a chimeric polypeptide.

In some embodiments, a nucleotide sequence encoding a subject RNA-guided polypeptide (e.g., a circular permuted Cas9 protein), a subject Cas9 fusion polypeptide, and/or a subject Cas9 guide RNA is operably linked to an inducible promoter. In some embodiments, a nucleotide sequence encoding a subject RNA-guided polypeptide (e.g., a circular permuted Cas9 protein), a subject Cas9 fusion polypeptide, and/or a subject Cas9 guide RNA is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a Cas9 guide RNA is operably linked to (under the control of) a promoter operable in a eukaryotic cell (e.g., a U6 promoter, an enhanced U6 promoter, an H1 promoter, and the like). In some cases, a nucleotide sequence encoding a subject RNA-guided polypeptide (e.g., a circular permuted Cas9 protein) or a subject Cas9 fusion polypeptide is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a subject RNA-guided polypeptide (e.g., a circular permuted Cas9 protein), a subject Cas9 fusion polypeptide, and/or a Cas9 guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a subject RNA-guided polypeptide (e.g., a circular permuted Cas9 protein) or a subject Cas9 fusion polypeptide can be provided as RNA. The RNA can be provided by direct chemical synthesis or may be transcribed in vitro from a DNA (e.g., encoding the protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Minis Bio LLC. See also Beumer et al. (2008) PNAS 105(50):19821-19826.

Vectors may be provided directly to a target host cell. In other words, the cells can be contacted with vectors comprising the subject nucleic acids such that the vectors are taken up by the cells. Methods for contacting cells with nucleic acid vectors that are plasmids include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding Cas9 guide RNA and/or a protein of the present disclosure (e.g., a subject RNA-guided polypeptide, e.g., a conditionally active RNA-guided polypeptide, a circular permuted Cas9 protein, a subject Cas9 fusion polypeptide, and the like) to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a Cas9 guide RNA and/or a protein of the present disclosure (e.g., a subject RNA-guided polypeptide, e.g., a conditionally active RNA-guided polypeptide, a circular permuted Cas9 protein, a subject Cas9 fusion polypeptide, and the like) to a cell may include nucleic acid sequences that encode for selectable markers in the target cells, so as to identify cells that have taken up the Cas9 guide RNA and/or subject protein.

A nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like), is in some cases an RNA. Thus, a protein of the present disclosure (e.g., a subject RNA-guided polypeptide, e.g., a conditionally active RNA-guided polypeptide, a circular permuted Cas9 protein, a subject Cas9 fusion polypeptide, and the like) can be introduced into cells as RNA. Methods of introducing RNA into cells are known in the art and may include, for example, direct injection, transfection, or any other method used for the introduction of DNA. A protein of the present disclosure (e.g., a subject RNA-guided polypeptide, e.g., a conditionally active RNA-guided polypeptide, a circular permuted Cas9 protein, a subject Cas9 fusion polypeptide, and the like) may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a protein of the present disclosure (e.g., a subject RNA-guided polypeptide, e.g., a conditionally active RNA-guided polypeptide, a circular permuted Cas9 protein, a subject Cas9 fusion polypeptide, and the like) may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO: 946). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A protein of the present disclosure (e.g., a subject RNA-guided polypeptide, e.g., a conditionally active RNA-guided polypeptide, a circular permuted Cas9 protein, a subject Cas9 fusion polypeptide, and the like) may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a Cas9 guide RNA, encoding a protein of the present disclosure, e.g., a subject RNA-guided polypeptide, e.g., a circular permuted Cas9 protein, a subject Cas9 fusion polypeptide, and the like), and proteins of the present disclosure (e.g., a subject RNA-guided polypeptide, e.g., a circular permuted Cas9 protein, a subject Cas9 fusion polypeptide, and the like) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A protein of the present disclosure (e.g., a subject RNA-guided polypeptide, e.g., a conditionally active RNA-guided polypeptide, a circular permuted Cas9 protein, a subject Cas9 fusion polypeptide, and the like) may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A protein of the present disclosure (e.g., a subject RNA-guided polypeptide, e.g., a conditionally active RNA-guided polypeptide, a circular permuted Cas9 protein, a subject Cas9 fusion polypeptide, and the like) may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a protein of the present disclosure (e.g., a subject RNA-guided polypeptide, e.g., a conditionally active RNA-guided polypeptide, a circular permuted Cas9 protein, a subject Cas9 fusion polypeptide, and the like) is at least 80% pure, at least 85% pure, at least 90% pure, at least 95% pure, at least 98% pure, or at least 99% pure (e.g., free of contaminants, non-desired proteins or other macromolecules, etc.).

In cases in which two or more different targeting complexes are provided to the cell (e.g., two different Cas9 guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a Cas9 guide RNA that does not change when the guide sequence is changed to hybridized to a desired target sequence (e.g., sequences that contribute to the Cas9 binding aspect of the guide RNA, e.g, the sequences that contribute to the dsRNA duplex(es) of the Cas9 guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a Cas9 guide RNA, except that the portion encoding the guide sequence portion of the guide RNA is an insertion sequence (an insertion site). An insertion site is any nucleotide sequence used for the insertion of a the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Introducing Components into a Target Cell

A Cas9 guide RNA (or a nucleic acid comprising a nucleotide sequence encoding same), and/or a protein of the present disclosure (e.g., a subject RNA-guided polypeptide, e.g., a conditionally active RNA-guided polypeptide, a circular permuted Cas9 protein, a subject Cas9 fusion polypeptide, and the like) (or a nucleic acid comprising a nucleotide sequence encoding same) and/or a donor template polynucleotide can be introduced into a host cell by any of a variety of well-known methods. A Cas9 guide RNA can be provided directly (e.g., as one or more RNA molecules), or can be provided as a DNA encoding the guide RNA.

Methods of introducing a nucleic acid (mRNA and/or DNA) into a cell (e.g., prokaryotic cell, eukaryotic cell, plant cell, vertebrate cell, mammalian cell, primate cell, non-human primate cell, human cell, and the like) are known in the art, and any convenient method can be used to introduce a nucleic acid (e.g., an expression construct) into a target cell. Suitable methods include, e.g., viral infection, transfection, conjugation, protoplast fusion, lipofection, nucleofection, electroporation, calcium phosphate precipitation, polyethyleneimine (PEI)-mediated transfection, DEAE-dextran mediated transfection, liposome-mediated transfection, particle gun technology, calcium phosphate precipitation, *agrobacterium*-mediated transformation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. Any or all of the components can be introduced into a cell as a composition [e.g., including any convenient combination of: a subject RNA-guided polypeptide (e.g., a circular permuted Cas9 protein) (or a nucleic acid comprising a nucleotide sequence encoding same), a Cas9 fusion protein with an internal insertion (or a nucleic acid comprising a nucleotide sequence encoding same), a Cas9 guide RNA (or a DNA comprising a nucleotide sequence encoding same), a donor polynucleotide, etc.] using known methods, e.g., such as nucleofection.

In some cases, a protein of the present disclosure (e.g., a subject RNA-guided polypeptide, e.g., a conditionally active RNA-guided polypeptide, a circular permuted Cas9 protein, a subject Cas9 fusion polypeptide, and the like) is provided as a nucleic acid (e.g., an mRNA, a DNA, a plasmid, an expression vector, a viral vector, etc.) that encodes protein. In some cases, a protein of the present disclosure (e.g., a subject RNA-guided polypeptide, e.g., a conditionally active RNA-guided polypeptide, a circular permuted Cas9 protein, a subject Cas9 fusion polypeptide, and the like) is provided as a protein.

A protein of the present disclosure (e.g., a subject RNA-guided polypeptide, e.g., a conditionally active RNA-guided polypeptide, a circular permuted Cas9 protein, a subject Cas9 fusion polypeptide, and the like) can be introduced into a cell (provided to the cell) by any convenient method; such methods are known to those of ordinary skill in the art. As an illustrative example, a protein of the present disclosure (e.g., a subject RNA-guided polypeptide, e.g., a conditionally active RNA-guided polypeptide, a circular permuted Cas9 protein, a subject Cas9 fusion polypeptide, and the like) can be injected directly into a cell (e.g., with or without a Cas9 guide RNA, with or without a nucleic acid encoding a Cas9 guide RNA, and with or without a donor polynucleotide). As another example, a preformed complex of a protein of the present disclosure (e.g., a subject RNA-guided polypeptide, e.g., a conditionally active RNA-guided polypeptide, a circular permuted Cas9 protein, a subject Cas9 fusion polypeptide, and the like) plus a Cas9 guide RNA is referred to as a ribonucleoprotein (RNP) complex, can be introduced into a cell (e.g., via nucleofection; via injection; via a protein transduction domain (PTD) conjugated to one or more components, e.g., conjugated to the protein, conjugated to a guide RNA, and the like). As noted above, a Cas9 guide RNA can be introduced into a cell as RNA or as DNA encoding the RNA (e.g., an expression vector encoding the Cas9 guide RNA).

Host Cells (Modified Cells, e.g., Genetically Modified Cells)

The present disclosure provides host cells comprising (e.g., genetically modified to comprise) a protein and/or nucleic acid of the present disclosure. The present disclosure provides host cells comprising (e.g., modified to comprise, e.g., genetically modified to comprise) a recombinant vector of the present disclosure. The present disclosure provides host cells comprising a protein of the present disclosure (e.g., a subject RNA-guided polypeptide, e.g., a conditionally active RNA-guided polypeptide, a circular permuted Cas9 protein, a subject Cas9 fusion polypeptide, and the like). The present disclosure provides host cells comprising a nucleic acid molecule that includes a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like). In some cases, the nucleotide sequence encoding a protein of the present disclosure is integrated into the genome of the host cell. In some cases, the nucleotide sequence encoding a protein of the present disclosure is not integrated into the genome of the host cell (e.g., in some cases it is maintained episomally). The modified host cells are in some cases in vitro host cells. In some cases, the modified host cells are in vivo host cells.

Suitable host cells include, e.g. a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, cnidarian, echinoderm, nematode, etc.); a cell from a vertebrate animal (e.g., fish, amphibian, reptile, bird, mammal); a cell from a mammal (e.g., a cell from a rodent, a cell from a human, etc.); and the like.

A suitable host cell can be a stem cell (e.g. an embryonic stem (ES) cell, an induced pluripotent stem (iPS) cell); a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures include cultures that may have been passaged 0 times, 1 time, 2 times, 4 times, 5 times, 10 times, or 15 times, but not enough times go through the crisis stage. Primary cell lines can be maintained for fewer than 10 passages in vitro. Host cells are in many embodiments unicellular organisms, or are grown in culture.

If the cells are primary cells, they may be harvest from an organism (e.g., an individual) by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, e.g., from 5-25 mM. Convenient buffers include HEPES, phosphate buffers, lactate buffers, etc. The cells may be used immediately, or they may be stored, frozen, for long periods of time, being thawed and capable of being reused. In such cases, the cells can be frozen in 10% dimethyl sulfoxide (DMSO), 50% serum, 40% buffered medium, or some other such solution as is commonly used in the art to preserve cells at such freezing temperatures, and thawed in a manner as commonly known in the art for thawing frozen cultured cells.

In some embodiments, a subject genetically modified host cell is in vitro. In some embodiments, a subject genetically modified host cell is in vivo. In some embodiments, a subject genetically modified host cell is a prokaryotic cell or is derived from a prokaryotic cell. In some embodiments, a subject genetically modified host cell is a bacterial cell or is derived from a bacterial cell. In some embodiments, a subject genetically modified host cell is an archaeal cell or is derived from an archaeal cell. In some embodiments, a subject genetically modified host cell is a eukaryotic cell or is derived from a eukaryotic cell. In some embodiments, a subject genetically modified host cell is a plant cell or is derived from a plant cell. In some embodiments, a subject genetically modified host cell is an animal cell or is derived from an animal cell. In some embodiments, a subject genetically modified host cell is an invertebrate cell or is derived from an invertebrate cell. In some embodiments, a subject genetically modified host cell is a vertebrate cell or is derived from a vertebrate cell. In some embodiments, a subject genetically modified host cell is a mammalian cell or is derived from a mammalian cell. In some embodiments, a subject genetically modified host cell is a rodent cell or is derived from a rodent cell. In some embodiments, a subject genetically modified host cell is a human cell or is derived from a human cell. In some embodiments, a subject genetically modified host cell is a non-human mammalian cell or is derived from a non-human mammalian cell. In some embodiments, a subject genetically modified host cell is a non-human primate cell or is derived from a non-human primate cell. In some embodiments, a subject genetically modified host cell is an insect cell or is derived from an insect cell. In some embodiments, a subject genetically modified host cell is an arachnid cell or is derived from an arachnid cell.

The present disclosure further provides progeny of a subject genetically modified cell, where the progeny can comprise the same exogenous nucleic acid or polypeptide as the subject genetically modified cell from which it was derived. The present disclosure further provides a composition comprising a subject genetically modified host cell.

In some cases, a subject modified cell (e.g., genetically modified cell) includes a subject conditionally active RNA-guided polypeptide (e.g., a conditionally active circular permuted Cas9 protein) [and/or a nucleic acid encoding the same], and the cell can be considered a biosensor cell. In the presence of a cellular input signal (signal present in the cell, e.g., the presence of an active form of a protease such as a viral or cancer-associated protease), the cleavable linker is cleaved, activating the conditionally active RNA-guided polypeptide, and activation leads to a cellular output signal. As an illustrative example, a cellular output signal could be repressed expression of a fluorescent protein such as GFP, and a decrease in fluorescence would be considered the cellular output signal. For example, if a subject conditionally active RNA-guided polypeptide (e.g., a conditionally active circular permuted Cas9 protein) lacks a catalytic HNH domain and lack a RuvC domain, activation of the polypeptide might increase the polypeptide's RNA-guided sequence specific binding ability, and therefore allow the protein to act as a transcriptional repressor (in the present of an appropriately targeted Cas9 guide RNA). In such a case, GFP expression may be detectable prior to activation (e.g., prior to cleavable of the cleavable linker), but cleavage of the cleavable linker would activate the conditionally active RNA-guided polypeptide, turning the protein into an active repressor, which would bind to the DNA encoding the GFP, effectively blocking transcription of the GFP protein and decreasing that amount of detectable signal. In such a case, a decrease of signal would be considered the cellular output. The cellular input could be any input that leads to cleavage of the cleavable linker. As an illustrative example, if the linker is cleavable by a viral protease, then presence of an active viral protease could be considered to be the cellular input, which would thereby lead to cleavage of the cleavable linker (and therefore activation of the conditionally active RNA-guided polypeptide).

Donor Polynucleotide (Donor Template)

In some cases, the contacting occurs under conditions that are permissive for nonhomologous end joining or homology-directed repair. In some cases, the method further comprises contacting the target DNA with a donor polynucleotide, wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, Cas9 guide RNA and a protein of the present disclosure (e.g., a subject RNA-guided polypeptide, e.g., a conditionally active RNA-guided polypeptide, a circular permuted Cas9 protein, a subject Cas9 fusion polypeptide, and the like) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, a complex comprising a Cas9 guide RNA and a protein of the present disclosure (e.g., a subject RNA-guided polypeptide, e.g., a conditionally active RNA-guided polypeptide, a circular permuted Cas9 protein, a subject Cas9 fusion polypeptide, and the like) is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into a target DNA sequence, a polynucleotide comprising a donor sequence to be inserted is also provided to the cell. By a "donor sequence" or "donor polynucleotide" it is meant a nucleic acid sequence to be inserted at the cleavage site induced by a protein of the present disclosure (e.g., a subject RNA-guided polypeptide, e.g., a conditionally active RNA-guided polypeptide, a circular permuted Cas9 protein, a subject Cas9 fusion polypeptide, and the like). The donor polynucleotide will contain sufficient homology to a genomic sequence at the cleavage site, e.g. 70%, 80%, 85%, 90%, 95%, or 100% homology with the nucleotide sequences flanking the cleavage site, e.g. within about 50 bases or less of the cleavage site, e.g. within about 30 bases, within about 15 bases, within about 10 bases, within about 5 bases, or immediately flanking the cleavage site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) will support homology-directed repair. Donor sequences can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described above for nucleic acids encoding a Cas9 guide RNA and/or a protein of the present disclosure (e.g., a subject RNA-guided polypeptide, e.g., a conditionally active RNA-guided polypeptide, a circular permuted Cas9 protein, a subject Cas9 fusion polypeptide, and the like) and/or donor polynucleotide.

Non-Human Modified Organisms

If a modified cell (e.g., genetically modified cell, as described above) is a eukaryotic single-cell organism, then the modified cell can be considered a genetically modified organism. In some embodiments, a subject non-human modified organism (e.g., non-human genetically modified organism) is a transgenic multicellular organism, in which a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) is integrated into the genome of the organism.

In some embodiments, a subject genetically modified non-human host cell (e.g., a cell that has been genetically modified with an exogenous nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) can generate a subject genetically modified non-human organism (e.g., a rodent, a mouse, a fish, an amphibian, a frog, a reptile, an ungulate, a fly, a worm, an insect, an arachnid, an annelid, a plant, etc.). For example, if the genetically modified host cell is a pluripotent stem cell (i.e., PSC) or a germ cell (e.g., sperm, oocyte, etc.), an entire genetically modified organism can be derived from the genetically modified host cell. In some embodiments, the genetically modified host cell is a pluripotent stem cell (e.g., ESC, iPSC, pluripotent plant stem cell, etc.) or a germ cell (e.g., sperm cell, oocyte, etc.), either in vivo or in vitro, that can give rise to a genetically modified organism. In some embodiments the genetically modified host cell is a vertebrate PSC (e.g., ESC, iPSC, etc.) and is used to generate a genetically modified organism (e.g. by injecting a PSC into a blastocyst to produce a chimeric/mosaic animal, which could then be mated to generate non-chimeric/non-mosaic genetically modified organisms; grafting in the case of plants; etc.). Any convenient method/protocol for producing a genetically modified organism is suitable for producing a genetically modified host cell comprising an exogenous nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like). Methods of producing genetically modified organisms are known in the art. For example, see Cho et al., Curr Protoc Cell Biol. 2009 March; Chapter 19:Unit 19.11: Generation of transgenic mice; Gama et al., Brain Struct Funct. 2010 March; 214(2-3):91-109. Epub 2009 Nov. 25: Animal transgenesis: an overview; Husaini et al., GM Crops. 2011 June-December; 2(3):150-62. Epub 2011 Jun. 1: Approaches for gene targeting and targeted gene expression in plants.

In some embodiments, a genetically modified organism comprises a target cell for methods of the invention, and thus can be considered a source for target cells. For example, if a genetically modified cell comprising one or more exogenous nucleic acids comprising nucleotide sequences encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) is used to generate a genetically modified organism, then the cells of the genetically modified organism comprise the one or more exogenous nucleic acids comprising nucleotide sequences encoding the protein. In some such embodiments, the DNA of a cell or cells of the genetically modified organism can be targeted for modification by introducing into the cell or cells a Cas9 guide RNA (e.g., a truncated Cas9 guide RNA) (or a nucleic acid encoding the Cas9 guide RNA). For example, the introduction of a Cas9 guide RNA (or a DNA encoding the same) into a subset of cells (e.g., brain cells, intestinal cells, kidney cells, lung cells, blood cells, etc.) of the genetically modified organism can target the DNA of such cells for modification, the genomic location of which will depend on the targeting sequence of the introduced Cas9 guide RNA.

In some cases, a genetically modified organism is a source of target cells for methods of the invention. For example, a genetically modified organism comprising cells that are genetically modified with an exogenous nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) can provide a source of genetically modified cells, for example PSCs (e.g., ESCs, iPSCs, sperm, oocytes, etc.), neurons, progenitor cells, cardiomyocytes, etc.

In some cases, a genetically modified cell is a PSC comprising an exogenous nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like). As such, the PSC can be a target cell such that the DNA of the PSC can be targeted for modification by introducing into the PSC a Cas9 guide RNA (or a nucleic acid encoding the Cas9 guide RNA), and optionally a donor nucleic acid (donor polynucleotide), and the genomic location of the modification will depend on the targeting sequence of the introduced Cas9 guide RNA. Thus, in some embodiments, the methods described herein can be used to modify the DNA (e.g., delete and/or replace any desired genomic location) of PSCs derived from a subject genetically modified organism. Such modified PSCs can then be used to generate organisms having both (i) an exogenous nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) and (ii) a DNA modification that was introduced into the PSC.

An exogenous nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter, EF1α promoter), inducible promoters (e.g., heat shock promoter, Tetracycline-regulated promoter, Steroid-regulated promoter, Metal-regulated promoter, estrogen receptor-regulated promoter, etc.), spatially restricted and/or temporally restricted promoters (e.g., a tissue specific promoter, a cell type specific promoter, etc.), etc.

A subject genetically modified non-human organism can be any organism other than a human, including for example, a plant (e.g., a tobacco plant, a fruiting tree, a dicot, a monocot, a soy plant, a legume, a wheat plant, a barley plant, a rice plant, a tomato plant, a corn plant, a crop plant, and the like); algae; an invertebrate (e.g., a cnidarian, an echinoderm, a worm, an insect, an arachnid, an annelid, a fly, etc.); a vertebrate (e.g., a fish (e.g., zebrafish, puffer fish, gold fish, etc.), an amphibian (e g, salamander, frog, etc.), a reptile, a bird, a mammal, etc.); an ungulate (e.g., a goat, a pig, a sheep, a cow, etc.); a rodent (e.g., a mouse, a rat, a hamster, a guinea pig); a lagomorpha (e.g., a rabbit); etc.

Transgenic Non-Human Animals

As described above, in some embodiments, a subject nucleic acid (e.g., one or more nucleic acids comprising nucleotide sequences encoding a protein of the present disclosure (e.g., a subject RNA-guided polypeptide, e.g., a conditionally active RNA-guided polypeptide, a circular permuted Cas9 protein, a subject Cas9 fusion polypeptide, and the like), e.g., a recombinant expression vector, is used as a transgene to generate a transgenic animal that produces a protein of the present disclosure (e.g., a subject RNA-guided polypeptide, e.g., a conditionally active RNA-guided polypeptide, a circular permuted Cas9 protein, a subject Cas9 fusion polypeptide, and the like). Thus, the present disclosure further provides a transgenic non-human animal, which animal comprises a transgene comprising a subject nucleic acid comprising a nucleotide sequence encoding protein of the present disclosure (e.g., a subject RNA-guided polypeptide, e.g., a conditionally active RNA-guided polypeptide, a circular permuted Cas9 protein, a subject Cas9 fusion polypeptide, and the like). In some embodiments, the genome of the transgenic non-human animal comprises a subject nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like). In some embodiments, the transgenic non-human animal is homozygous for the genetic modification. In some embodiments, the transgenic non-human animal is heterozygous for the genetic modification. In some embodiments, the transgenic non-human animal is a vertebrate, for example, a fish (e.g., zebra fish, gold fish, puffer fish, cave fish, etc.), an amphibian (frog, salamander, etc.), a bird (e.g., chicken, turkey, etc.), a reptile (e.g., snake, lizard, etc.), a mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some embodiments, the transgenic non-human animal is an invertebrate (e.g., an insect, an arachnid, etc.)

Nucleotide sequences encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter, EF1α, and the like), inducible promoters (e.g., heat shock promoter, Tetracycline-regulated promoter, Steroid-regulated promoter, Metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some embodiments, a subject nucleic acid (e.g., one or more nucleic acids comprising nucleotide sequences encoding a protein of the present disclosure (e.g., a subject RNA-guided polypeptide, e.g., a conditionally active RNA-guided polypeptide, a circular permuted Cas9 protein, a subject Cas9 fusion polypeptide, and the like), e.g., a recombinant expression vector, is used as a transgene to generate a transgenic plant that produces a protein of the present disclosure (e.g., a subject RNA-guided polypeptide, e.g., a conditionally active RNA-guided polypeptide, a circular permuted Cas9 protein, a subject Cas9 fusion polypeptide, and the like). Thus, the present disclosure further provides a transgenic plant, which plant comprises a transgene comprising a subject nucleic acid comprising a nucleotide sequence encoding a protein of the present disclosure (e.g., a subject RNA-guided polypeptide, e.g., a conditionally active RNA-guided polypeptide, a circular permuted Cas9 protein, a subject Cas9 fusion polypeptide, and the like). In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, Agrobacterium-mediated transformation and the like. The choice of method is generally dependent on the type of cell being transformed and the circumstances under which the transformation is taking place (i.e. in vitro, ex vivo, or in vivo).

Transformation methods based upon the soil bacterium Agrobacterium tumefaciens are particularly useful for introducing an exogenous nucleic acid molecule into a vascular plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in which the tumor inducing functions are replaced by the nucleic acid sequence of interest to be introduced into the plant host.

Agrobacterium-mediated transformation generally employs cointegrate vectors or binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing Agrobacterium with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A subject nucleic acid may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of Agrobacterium tumefaciens, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for Agrobacterium-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

Also provided by the subject disclosure are transformed plant cells, tissues, plants and products that contain the transformed plant cells. A feature of the subject transformed cells, and tissues and products that include the same is the presence of a subject nucleic acid integrated into the genome, and production by plant cells of a protein of the present disclosure (e.g., a subject RNA-guided polypeptide, e.g., a conditionally active RNA-guided polypeptide, a circular permuted Cas9 protein, a subject Cas9 fusion polypeptide, and the like). Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a protein of the present disclosure (e.g., a subject RNA-guided polypeptide, e.g., a conditionally active RNA-guided polypeptide, a circular permuted Cas9 protein, a subject Cas9 fusion polypeptide, and the like) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Methods

A protein of the present disclosure (e.g., a subject RNA-guided polypeptide, e.g., a conditionally active RNA-guided polypeptide, a circular permuted Cas9 protein, a subject Cas9 fusion polypeptide, and the like) finds use in a variety of methods. A protein of the present disclosure (e.g., a subject RNA-guided polypeptide, e.g., a conditionally active RNA-guided polypeptide, a circular permuted Cas9 protein, a subject Cas9 fusion polypeptide, and the like) can be used in any method that a Cas9 protein can be used. For example, a protein of the present disclosure (e.g., a subject RNA-guided polypeptide, e.g., a conditionally active RNA-guided polypeptide, a circular permuted Cas9 protein, a subject Cas9 fusion polypeptide, and the like) can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Because a method that uses a protein of the present disclosure (e.g., a subject RNA-guided polypeptide, e.g., a conditionally active RNA-guided polypeptide, a circular permuted Cas9 protein, a subject Cas9 fusion polypeptide, and the like) includes binding of the polypeptide to a particular region in a target nucleic acid (by virtue of being targeted there by an associated Cas9 guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid, modulation of translation of the target nucleic acid, genome editing, modulation of a protein associated with the target nucleic acid, isolation of the target nucleic acid, etc.). For examples of suitable methods, see, for example, Jinek et al., Science. 2012 Aug. 17; 337(6096): 816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al. Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20160304846, 20160215276, 20150166980, 20150071898, 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a protein of the present disclosure (e.g., a subject RNA-guided polypeptide, e.g., a conditionally active RNA-guided polypeptide, a circular permuted Cas9 protein, a subject Cas9 fusion polypeptide, and the like) encompass all methods for contacting the target nucleic acid. For example, a protein of the present disclosure (e.g., a subject RNA-guided polypeptide, e.g., a conditionally active RNA-guided polypeptide, a circular permuted Cas9 protein, a subject Cas9 fusion polypeptide, and the like) can be provided as protein, RNA (encoding the polypeptide), or DNA (encoding the polypeptide); while a Cas9 guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) [for the protein], in the form of an RNA [for the guide RNA]), and also encompasses the introduction into the cell of one or more nucleic acids (DNA,RNA) encoding one or more of the components (e.g., nucleic acid(s) having nucleotide sequence(s) encoding a protein of the present disclosure (e.g., a subject RNA-guided polypeptide, e.g., a conditionally active RNA-guided polypeptide, a circular permuted Cas9 protein, a subject Cas9 fusion polypeptide, and the like), nucleic acid(s) having nucleotide sequence(s) encoding guide RNA(s), and the like). Because the methods can also be performed in vitro outside of a cell, a method that includes contacting a target nucleic acid, (unless otherwise specified) encompasses contacting outside of a cell in vitro, inside of a cell in vitro (e.g., a cell line in culture), inside of a cell in vivo, inside of a cell ex vivo, etc.

In some cases, a subject method is a method that includes contacting a target nucleic acid with a protein of the present disclosure (e.g., a subject RNA-guided polypeptide, e.g., a conditionally active RNA-guided polypeptide, a circular permuted Cas9 protein, a subject Cas9 fusion polypeptide, and the like). In some cases, a subject method includes contacting a target nucleic acid with a protein of the present disclosure (e.g., a subject RNA-guided polypeptide, e.g., a conditionally active RNA-guided polypeptide, a circular permuted Cas9 protein, a subject Cas9 fusion polypeptide, and the like) and a Cas9 guide RNA. In some cases, a subject method includes contacting a target nucleic acid with a protein of the present disclosure (e.g., a subject RNA-guided polypeptide, e.g., a conditionally active RNA-guided polypeptide, a circular permuted Cas9 protein, a subject Cas9 fusion polypeptide, and the like) and a Cas9 guide RNA and an agent that cleaves the cleavable linker of a conditionally active RNA-guided polypeptide (e.g., a protease). In some cases, a method is a method of contacting a target nucleic acid with a system. In some cases, the system can include one or more of: (i) a protein of the present disclosure (e.g., a subject RNA-guided polypeptide, e.g., a conditionally active RNA-guided polypeptide, a circular permuted Cas9 protein, a subject Cas9 fusion polypeptide, and the like) and a Cas9 guide RNA; (ii) a protein of the present disclosure (e.g., a subject RNA-guided polypeptide, e.g., a conditionally active RNA-guided polypeptide, a circular permuted Cas9 protein, a subject Cas9 fusion polypeptide, and the like) and a Cas9 guide RNA and an agent that cleaves the cleavable linker of a conditionally active RNA-guided polypeptide (e.g., a protease); (iii) a protein of the present disclosure (e.g., a subject RNA-guided polypeptide, e.g., a conditionally active RNA-guided polypeptide, a circular permuted Cas9 protein, a subject Cas9 fusion polypeptide, and the like) and a Cas9 guide RNA and a donor polynucleotide; or (iv) a protein of the present disclosure (e.g., a subject RNA-guided polypeptide, e.g., a conditionally active RNA-guided polypeptide, a circular permuted Cas9 protein, a subject Cas9 fusion polypeptide, and the like) and a Cas9 guide RNA and a donor polynucleotide and an agent that cleaves the cleavable linker of a conditionally active RNA-guided polypeptide (e.g., a protease).

In some cases, a subject method is a method of generating a biosensor cell (described above) and includes introducing into the cell a conditionally active RNA-guided polypeptide (e.g., a conditionally active circular permuted Cas9 protein).

The inventors have created conditionally active RNA-guided polypeptides (e.g., conditionally active circular permuted Cas9 proteins) that can be used to sense and respond to the cellular environment, i.e., respond to a cellular input signal, e.g., the presence or absence of a protease. Many pathogenic viruses require a protease to complete the viral life cycle and microbes utilize proteases as virulence agents. Thus, a subject conditionally active RNA-guided polypeptide (e.g., conditionally active circular permuted Cas9 protein) can sense and respond to viral/pathogen infection at a subcellular level. For example, in response to the cellular input, a the conditionally active RNA-guided polypeptide can enact can enact outcomes (output signals) such as pathogen tracking, detection and diagnostics, direction of an anti-viral attack, up-regulation of an immune response, a holistic organism based response, and/or cell death (e.g., an 'altruistic' act to stop the spread of infection), e.g., by targeting an essential gene for reduced expression and/or targeting a gene for lethal overexpression (depending on the type of conditionally active RNA-guided polypeptide used).

As one illustrative example, Potyvirus are important plant pathogens leading to substantial losses in a range of crops from potato and cassava to tomatoes and stone fruit. Containing and managing Potyviral infections for stone fruit alone are estimated to have exceeded $10,000 million since 1970. Thus, in some cases, the cleavable linker of a subject conditionally active RNA-guided polypeptide (e.g., conditionally active circular permuted Cas9 protein) can be cleavable by a Potyvirus protease, and in this way cells that are infected will activate the conditionally active polypeptide, leading to a desired outcome, e.g., increased expression of a target protein (e.g., if the conditionally active polypeptide is fused to a transcriptionally activating domain—it can be used to increase expression of desired target proteins only in the presence of the protease that cleaves the cleavable linker). In similar scenarios, subject a conditionally active RNA-guided polypeptide (e.g., conditionally active circular permuted Cas9 protein) can be used to sense and respond to viruses important to human health such as Dengue, Zika, Hepatitis C, Herpes and HIV. Such a sense and respond platform can be used for many research, diagnostic, and clinical applications, and can be utilized in both plant (e.g., agricultural) and animal (e.g., farm animals) settings.

Methods such as these can be applied in agriculturally relevant plant crops, and animals as well as mammalian cells and any desired organism. Moreover the inherent programmability of a subject conditionally active RNA-guided polypeptide (e.g., conditionally active circular permuted Cas9 protein) allows the protein to enact any desired response to protease detection upon pathogen infection. This allows, e.g., for the activation of hypersensitive response (HR) response genes to prevent further plant infection, while also allowing for outcomes such as the activation or repression of other immune genes, viral genome cleavage, host genome cleavage, or activation/repression of reporter genes to allow for pathogen tracking or diagnostics. Additionally, any or all of these outcomes could be enacted simultaneously via the multiplex nature of Cas9 targeting (e.g., using two or more Cas9 guide RNAs).

A subject conditionally active RNA-guided polypeptide (e.g., conditionally active circular permuted Cas9 protein) can sense and respond to the presence of the genetic inputs of organisms, including pathogens such as viruses, bacteria and fungi. More specifically these tools may be used in any situation in which it is desirable to sense a cellular input and, in a downstream manner, control gene expression or alter the sequence of the genome or epigenetic condition. For example, in response to a viral infection, a subject conditionally active RNA-guided polypeptide (e.g., conditionally active circular permuted Cas9 protein) could activate an immune response in plant or animal cells. In some cases, the cell input is an endogenous cellular cue such as the upregulation of a protease if the cell becomes a cancerous cell, and the desired output could be, for example, cell death, e.g., by activating toxic proteins or decreasing expression of essential genes. As noted above, in another embodiment the subject conditionally active RNA-guided polypeptide (e.g., conditionally active circular permuted Cas9 protein) may respond to pathogenic invasion. In yet another embodiment the subject conditionally active RNA-guided polypeptide (e.g., conditionally active circular permuted Cas9 protein) may respond to a synthetic activation such as the expression of a gene in trans or the posttranslational assembly of a protease. In any or all of these cases, one or many outputs can be programmed to occur upon activation of the conditionally active polypeptide. Such programmable outputs will be of broad use for diagnostics, disease prevention, disease treatment, pathogen tracking, immune system up and down regulation, disease vaccination, pest/disease vector control, disease vector vaccination, and plant/animal based agricultural manipulations and disease prevention.

Target Nucleic Acids and Target Cells of Interest

A protein of the present disclosure (e.g., a subject RNA-guided polypeptide, e.g., a conditionally active RNA-guided polypeptide, a circular permuted Cas9 protein, a subject Cas9 fusion polypeptide, and the like), when bound to a guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome, derived from a chromosome, chromosomal, plasmid, viral, extracellular, intracellular, mitochondrial, chloroplast, linear, circular, etc.) and can be from any organism (e.g., as long as the Cas9 guide RNA can hybridize to a target sequence in a target nucleic acid, that target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, cnidarian, echinoderm, nematode, etc.); a cell from a vertebrate animal (e.g., fish, amphibian, reptile, bird, mammal); a cell from a mammal (e.g., a cell from a rodent, a cell from a human, etc.); and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-74 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. An RNA-guided polypeptide comprising, in order from N-terminus to C-terminus: (a) a C-terminal fragment of a parent RNA-guided polypeptide, wherein the parent RNA-guided polypeptide comprises, in order from N- to C-terminus: i) a first RuvC subdomain; ii) a second RuvC subdomain; iii) an HNH domain; and iv) a third RuvC subdomain; (b) a linker; and (c) an N-terminal fragment of the parent RNA-guided polypeptide, 2. The RNA-guided polypeptide of 1, wherein the linker is a polypeptide linker.

3. The RNA-guided polypeptide of 1 or 2, wherein the linker is a cleavable linker.

4. The RNA-guided polypeptide of 3, wherein the cleavable linker is selected from: an acid-labile linker, a photo-labile linker, a dimethyl linker, a linker cleavable by a protease, and a disulfide containing linker.

5. The RNA-guided polypeptide of any one of 3-4, wherein the cleavable linker is a polypeptide linker comprising a target sequence for a protease.

6. The RNA-guided polypeptide of 5, wherein the protease is a viral, fungal, or bacterial protease.

7. The RNA-guided polypeptide of 5, wherein the protease is a viral or bacterial protease selected from: a Potyviridae protease, a Tobacco Etch Virus (TEV) protease, a Turnip Mosaic Virus (TuMV) protease, a Plum Pox Virus (PPV) protease, a Potato virus Y (PVY) protease, a Cassava brown streak virus protease, a Picornaviridae protease, a Human rhinovirus protease, a PreScission protease, a Herpesviridae protease, a Epstein-Barr virus (EBV) protease, a BVRF2 protease, a Kaposi's sarcoma-associated herpesvirus (KSHV) protease, a Cytomegalovirus (CMV) protease, a UL80 APNG protease, a Flaviviridae protease, a Flavivirus protease, a Zika virus protease, a Yellow fever virus protease, a Dengue virus protease, a DENV2 protease, a west nile virus protease, a pestivirus protease, a NS3 protease, a NS2B/NS3pro protease, a AvrPphB protease, a *P. syringae* pv. *phaseolicola* protease, a AvrRpt2 protease, a *Pseudomonas syringae* pv. tomato protease, a *Yersinia pestis* (plauge) protease, a yopT protease, a Togaviridae protease, a alphavirus genus protease, a SARS virus protease, and a 3c-like endopeptidase.

8. The RNA-guided polypeptide of any one of 3-7, wherein the cleavable linker is a polypeptide linker comprising a target sequence for a Tobacco Etch Virus (TEV) protease.

9. The RNA-guided polypeptide of any one of 3-8, wherein the RNA-guided polypeptide is conditionally active, having reduced activity when the cleavable linker is uncleaved relative to when the cleavable linker is cleaved.

10. The RNA-guided polypeptide of 9, wherein activity of the RNA-guided polypeptide when the cleavable linker is cleaved is 1.1-fold or more relative to the activity of the RNA-guided polypeptide when the cleavable linker is uncleaved.

11. The RNA-guided polypeptide of 9 or of 10, wherein the linker has a length equivalent to a range of from 1 to 10 amino acids.

12. The RNA-guided polypeptide of any one of 9-11, wherein the linker has a length equivalent to a range of from 2 to 8 amino acids.

13. The RNA-guided polypeptide of any one of 1-8, wherein the linker has a length equivalent to 11 or more amino acids.

14. The RNA-guided polypeptide of any one of 1-8, wherein the linker has a length equivalent to a range of from 11 to 50 amino acids.

15. The RNA-guided polypeptide of any one of 1-14, wherein the C-terminal amino acid of said N-terminal fragment corresponds to amino acid 182D, 200P, 231G, 271Y, 311E, 1011G, 1017D, 1024K, 1029I, 1030G, 1032A, 1042I, 1245L, 1249P, 1250E, or 1283A (or any one of the amino acid positions listed in Table 2) of the amino acid sequence set forth in SEQ ID NO: 17 or 111.

16. The RNA-guided polypeptide of any one of 1-15, wherein said N-terminal fragment comprises an amino acid sequence corresponding to amino acids 1-182, 1-200, 1-231, 1-271, 1-311, 1-1011, 1-1017, 1-1024, 1-1029, 1-1030, 1-1032, 1-1042, 1-1245, 1-1249, 1-1250, or 1-1283 (or 1-x where x is any one of the amino acid positions listed in Table 2) of the amino acid sequence set forth in SEQ ID NO: 17 or 111.

17. The RNA-guided polypeptide of any one of 1-16, comprising an amino acid sequence having 85% or more identity with the amino acid sequence set forth in any one of SEQ ID NOs: 1-16, wherein the stretch of Xs within the sequences set forth in SEQ ID NOs: 1-16 marks the position of the linker.

18. The RNA-guided polypeptide of any one of 1-16, wherein the parent RNA-guided polypeptide comprises an amino acid sequence having 85% or more identity with the amino acid sequence set forth in any one of SEQ ID NOs: 17 and 111-912.

19. The RNA-guided polypeptide of any one of 1-18, wherein the RNA-guided polypeptide has nickase activity.

20. The RNA-guided polypeptide of any one of 1-19, wherein the RNA-guided polypeptide lacks a catalytically active RuvC domain and/or lacks a catalytically active HNH domain.

21. The RNA-guided polypeptide of any one of 1-20, wherein the RNA-guided polypeptide lacks a catalytically active RuvC domain and lacks a catalytically active HNH domain.

22. The RNA-guided polypeptide of any one of 1-21, wherein the RNA-guided polypeptide is fused to a heterologous polypeptide.

23. The RNA-guided polypeptide of any one of 1-22, wherein the RNA-guided polypeptide is fused to a nuclear localization sequence (NLS).

24. The RNA-guided polypeptide of 22 or 23, wherein the RNA-guided polypeptide is fused to a transcription activation domain.

25. The RNA-guided polypeptide of 22 or 23, wherein the RNA-guided polypeptide is fused to a transcription repressor domain.

26. The RNA-guided polypeptide of 22 or 23, wherein the heterologous polypeptide provides an activity selected from: transcriptional modulation activity; DNA-modifying activity; and protein modifying activity.

27. The RNA-guided polypeptide of 26, wherein the heterologous polypeptide provides a DNA-modifying activity selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

28. The RNA-guided polypeptide of 26, wherein the heterologous polypeptide provides a DNA-modifying activity selected from: nuclease activity, methyltransferase activity, demethylase activity, deamination activity, depurination activity, integrase activity, transposase activity, and recombinase activity.

29. The RNA-guided polypeptide of 22 or 23, wherein the heterologous polypeptide exhibits a histone modification activity.

30. The RNA-guided polypeptide of any one of 22, 23, and 29, wherein the heterologous polypeptide provides a protein modifying activity selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from 0-GlcNAc transferase) and deglycosylation activity.

31. The RNA-guided polypeptide of any one of 22, 23, and 29, wherein the heterologous polypeptide provides a protein modifying activity selected from: methyltransferase activity, demethylase activity, acetyltransferase activity, and deacetylase activity.

32. A Cas9 fusion polypeptide, comprising (a) a Cas9 polypeptide, and (b) a heterologous polypeptide inserted internally within the Cas9 polypeptide, wherein the heterologous polypeptide is inserted at a position that is immediately adjacent and C-terminal to an amino acid residue corresponding to a residue selected from 182D, 200P, 231G, 271Y, 311E, 1011G, 1017D, 1024K, 1029I, 1030G, 1032A, 1042I, 1245L, 1249P, 1250E, and 1283A (or any one of the amino acid positions listed in Table 2) of the amino acid sequence set forth in SEQ ID NO: 17 or 111.

33. The Cas9 fusion polypeptide of 32, wherein the Cas9 fusion polypeptide is fused to a transcription activation domain.

34. The Cas9 fusion polypeptide of 32, wherein the Cas9 fusion polypeptide is fused to a transcription repressor domain.

35. The Cas9 fusion polypeptide of 32, wherein the heterologous polypeptide provides an activity selected from: transcriptional modulation activity; DNA-modifying activity; and protein modifying activity.

36. The Cas9 fusion polypeptide of 32, wherein the heterologous polypeptide provides a DNA-modifying activity selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

37. The Cas9 fusion polypeptide of 32, wherein the heterologous polypeptide provides a DNA-modifying activity selected from: nuclease activity, methyltransferase activity, demethylase activity, deamination activity, depurination activity, integrase activity, transposase activity, and recombinase activity.

38. The Cas9 fusion polypeptide of 32, wherein the heterologous polypeptide exhibits a histone modification activity.

39. The Cas9 fusion polypeptide of 32 or 38, wherein the heterologous polypeptide provides a protein modifying activity selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

40. The Cas9 fusion polypeptide of 32 or 38, wherein the heterologous polypeptide provides a protein modifying activity selected from: methyltransferase activity, demethylase activity, acetyltransferase activity, and deacetylase activity.

41. The Cas9 fusion polypeptide of any one of 32-40, wherein the Cas9 fusion polypeptide has nickase activity.

42. The Cas9 fusion polypeptide of any one of 32-41, wherein the Cas9 fusion polypeptide lacks a catalytically active RuvC domain and/or lacks a catalytically active HNH domain.

43. The Cas9 fusion polypeptide of 42, wherein the Cas9 fusion polypeptide lacks a catalytically active RuvC domain and lacks a catalytically active HNH domain.

44. The Cas9 fusion polypeptide of any one of 32-43, wherein the Cas9 fusion polypeptide is fused to a nuclear localization sequence (NLS).

45. A nucleic acid comprising a nucleotide sequence encoding (a) the RNA-guided polypeptide of any one of 1-31, or (b) the Cas9 fusion polypeptide of any one of 32-44.

46. The nucleic acid of 45, wherein said nucleotide sequence is operably linked to a promoter.

47. The nucleic acid of 46, wherein the promoter is operable in a eukaryotic cell.

48. The nucleic acid of any one of 45-47, wherein said nucleic acid is a recombinant expression vector.

49. The nucleic acid of 48, wherein the recombinant expression vector is selected from: a linear expression vector, a circular expression vector, a plasmid, and a viral expression vector.

50. The nucleic acid of 45, wherein said nucleic acid is an mRNA.

51. A cell, comprising
(a) the RNA-guided polypeptide of any one of 1-31, and/or
(b) the Cas9 fusion polypeptide of any one of 32-44, and/or
(c) the nucleic acid of any one of 45-50 (e.g., in some cases the nucleic acid is integrated into the genome of the cell and in some cases it is not integrated, e.g., is maintained episomally) 52. The cell of 51, wherein the cell is a eukaryotic cell.

53. The cell of 52, wherein the cell is a plant cell, an invertebrate cell, a vertebrate cell, a fish cell, an amphibian cell, an avian cell, a mammalian cell, a rodent cell, a mouse cell, a rat cell, a pig cell, a non-human primate cell, a primate cell, or a human cell.

54. The cell of 51, wherein the cell is a prokaryotic cell.

55. A method of generating a biosensor cell, comprising: introducing into a cell the RNA-guided polypeptide of any one of 1-31, or a nucleic acid encoding said engineered protein, wherein:
(a) the linker is a cleavable linker;
(b) the RNA-guided polypeptide is conditionally active, having reduced activity when the cleavable linker is uncleaved relative to when the cleavable linker is cleaved; and
(c) the cleavable linker is cleaved in the presence of an input signal present in the cell, thereby causing an increase in activity of the RNA-guided polypeptide, wherein said increase in activity generates one or more cellular output signals.

56. The method of 55, wherein the biosensor cell reduces spread of an infectious pathogen, wherein the cleavable linker is cleaved when an infectious pathogen is active in the cell, and wherein the increase in activity of the engineered protein causes a reduction in spread of the infectious pathogen.

57. The method of 56, wherein said one or more cellular output signals include death of the cell, thereby reducing spread of the infectious pathogen.

58. The method of any one of 55-57, wherein said one or more cellular output signals include the generation of a detectable signal.

59. The method of 58, wherein the detectable signal comprises increased expression of a fluorescent protein.

60. The method of 58, wherein the detectable signal comprises increased expression of a protein that can generate a colorimetric and/or fluorescent product when provided with an appropriate substrate.

61. The method of any one of 55-60, wherein said one or more cellular output signals include one or more of: an increase or decrease in the cell's ability to metabolize a compound; an increase or decrease in the cell's ability to divide; an increase or decrease in the cell's ability to communicate with other cells; an increase or decrease in the cell's ability to utilize a carbohydrate source; and an increase or decrease in the cell's ability to utilize a nutrient and/or nutrient source.

62. The method of any one of 55-61, further comprising a step of introducing a guide RNA into the cell.

63. A method of binding a target nucleic acid, comprising contacting a target nucleic acid with a guide RNA and:
(a) the RNA-guided polypeptide of any one of 1-31, or
(b) the Cas9 fusion polypeptide of any one of 32-44.

64. The method of 63, wherein said contacting comprises introducing into a cell a DNA or RNA encoding the RNA-guided polypeptide or the Cas9 fusion polypeptide.

65. The method of 63 or 64, wherein said contacting comprises introducing into a cell a DNA encoding the guide RNA.

66. The method of any one of 63-65, wherein said contacting comprises introducing into a cell a ribonucleoprotein (RNP) complex comprising (i) the guide RNA and (ii) the RNA-guided polypeptide or the Cas9 fusion polypeptide.

67. The method of any one of 63-66, wherein the RNA-guided polypeptide or the Cas9 fusion polypeptide modulates transcription from the target nucleic acid.

68. The method of any one of 63-71, wherein the RNA-guided polypeptide or the Cas9 fusion polypeptide modifies the target nucleic acid.

69. The method according to 68, wherein the wherein the RNA-guided polypeptide or the Cas9 fusion polypeptide cleaves the target nucleic acid.

70. The method of 69, wherein the RNA-guided polypeptide or the Cas9 fusion polypeptide has nickase activity.

71. The method of any one of 68-70, wherein a sequence of a donor template polynucleotide is incorporated into the target nucleic acid.

72. The method of 71, wherein the method comprises introducing the donor template polynucleotide into a cell comprising the target nucleic acid.

73. Any of the above aspects, wherein the parent RNA-guided polypeptide is a Cas9 protein.

74. Any of the above aspects, wherein the RNA-guided polypeptide is a circular permuted Cas9 protein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Generation and Functional Characterization of Circular Permuted Cas9 Proteins

FIG. 2 (panels A-C). (panel A) Schematic of a prototypical CP-Cas9 (circular permuted Cas9 protein, cpCas9) domain rearrangement (panel B) Method for creation of the CP-Cas9 libraries using a 'double backbone' approach, a new plasmid backbone with a promoter, RBS, and stop codons were transposed into Cas9. The original origin, antibiotic resistance marker all the way to the first and last codons of Cas9 were then excised via Type IIS restriction enzyme digest and a new $(GGS)_n$ linker was ligated in place. This effectively created a circularly permuted protein with an $(GGS)_n$ amino acid (AA) linker between the original N- and C-termini (e.g., 5 AA is GGSGG) (SEQ ID NO: 41). (panel C) Validation of the CP-Cas9 libraries by PCR. A primer which binds to the original C-terminus of Cas9 and a primer which binds to the 'new' plasmid backbone were used to amplify. CpCas9 variants had increasingly large fragments inserted after the original C-terminus leading to increasing large band sizes and a smear across the whole of this band size region, ~400 bp-5 kb. (panel D) is a schematic depicting the concept of circular permutation (cp) and the screening methods to identify functional circular permutants (cps).

FIG. 3 (panels A-D). (panel A) Schematic of the RFP repression florescence activated cell sorting (FACS) screen with controls from the experiment depicted to the right. (panel B) Representative FACS data depicting enrichment of each of the Cp-Cas9 libraries for cells which functionally repressed RFP via cpCas9 activity. Over two rounds of sorting each library was enriched for functional clones ~1000 fold. (panel C) PCR using primers from FIG. 2 on all libraries pre and post sorting. It is possible to see that in the 5 AA linker library all recovered clones appeared to have very few if any AA's swapped. However in the 10 AA linker lengths and to a greater extent in the 15 and 20 AA linker length libraries many more bands appeared to be enriched indicating a much greater diversity of Circular permuted Cas9's exist in these libraries. (panel D) deep sequencing data from the circular permutant (cp) library, pre and post screening for cp-dcas9 functionality, identifying the tested hits and internal controls. The sites hit are provided in Table 2.

Figure 4:
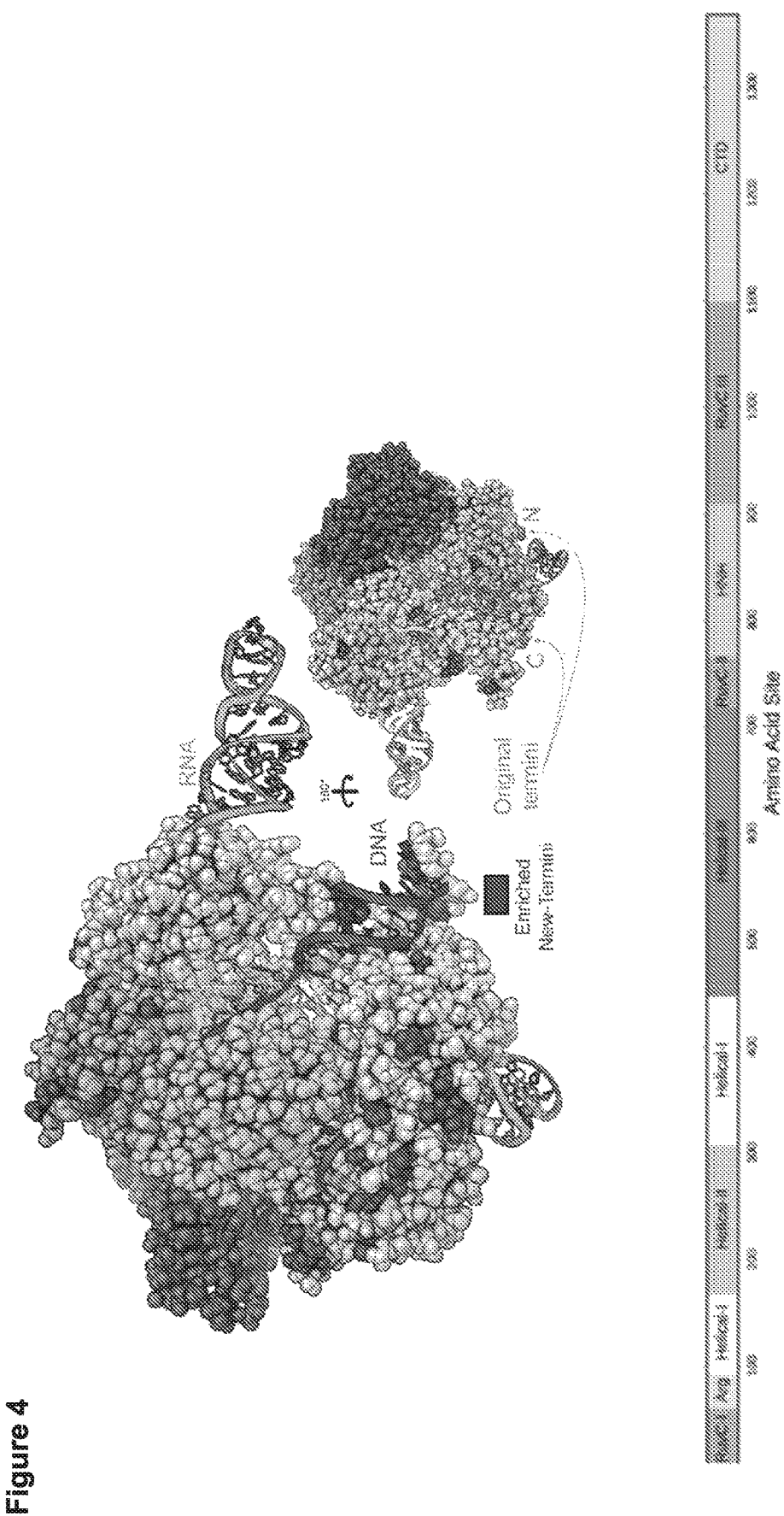
FIG. 4 presents functional cp sites from the deep sequencing data mapped onto the structure and compared to the location of the original N- and C-termini.

FIG. 4. Functional cp sites from the deep sequencing data mapped onto the structure and compared to the location of the original N & C termini.

FIG. 5 (panels A-B). (panel A) Sequence specific RNA guided binding and repression of a genomic target a GFP by individual cpCas9s recovered by picking individual colonies after the RFP repression screen. Negative control is first column, positive control (un-permuted dCas9) is second column. Many of the CPs were nearly as functional or as functional as dCas9 and some displayed better binding and repression activity than dCas9. (panel B) The normalized fits for the induction dose responses for each cpCas9 compared to dCas9 (in green) some (cp5,6,13,14, and 16) appeared to be slightly more active than dCas9 at lower induction doses while others behaved identically or slightly worse (cp1,2,3, 4,7,8,9,10,11,12,15,17).

FIG. 6. Binding and GFP repression (RNA guided binding and repression) exhibited by a subset of cpCas9s as a function of linker length (the linker between the former C-terminus and N-terminus). The generated data show that RNA guided binding (i.e., RNA guided sequence specific target DNA binding activity) can depend on the length of the linker. All linkers tested were repeats of the amino acid sequence GGS (e.g., 5 amino acids was GGSGG (SEQ ID NO: 41), while 10 amino acids was GGSGGSGGSG (SEQ ID NO: 42)).

Figure 7:
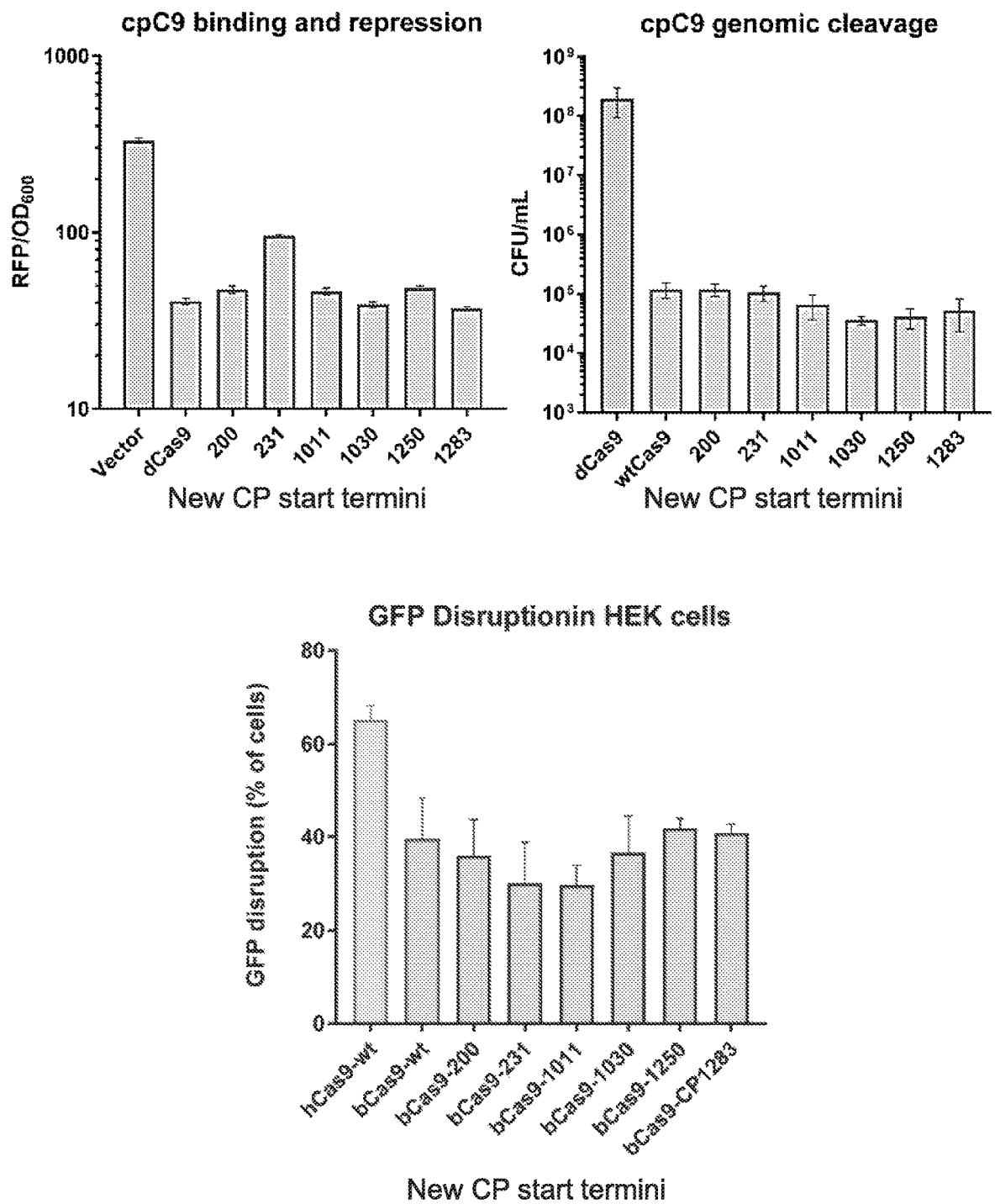
FIG. 7 presents data from a subset of the functional cp sites from the deep sequencing data (e.g., see FIG. 4) tested for: (1) CRISPRi based binding and repression in *Escherichia coli*, (2) genomic cleavage in *E. coli*, and (3) integrated GFP and genomic cleavage in human embryonic kidney cells.

FIG. 7. A subset of the functional cp sites from the deep sequencing data (e.g., see FIG. 4) were tested for: (1) CRISPRi based binding and repression in E. coli, (2) genomic cleavage in E. coli, and (3) integrated GFP and genomic cleavage in human embryonic kidney cells (hcas9 is human codon optimized cas9, bcas9 is bacterial codon optimized cas9).

Figure 8:
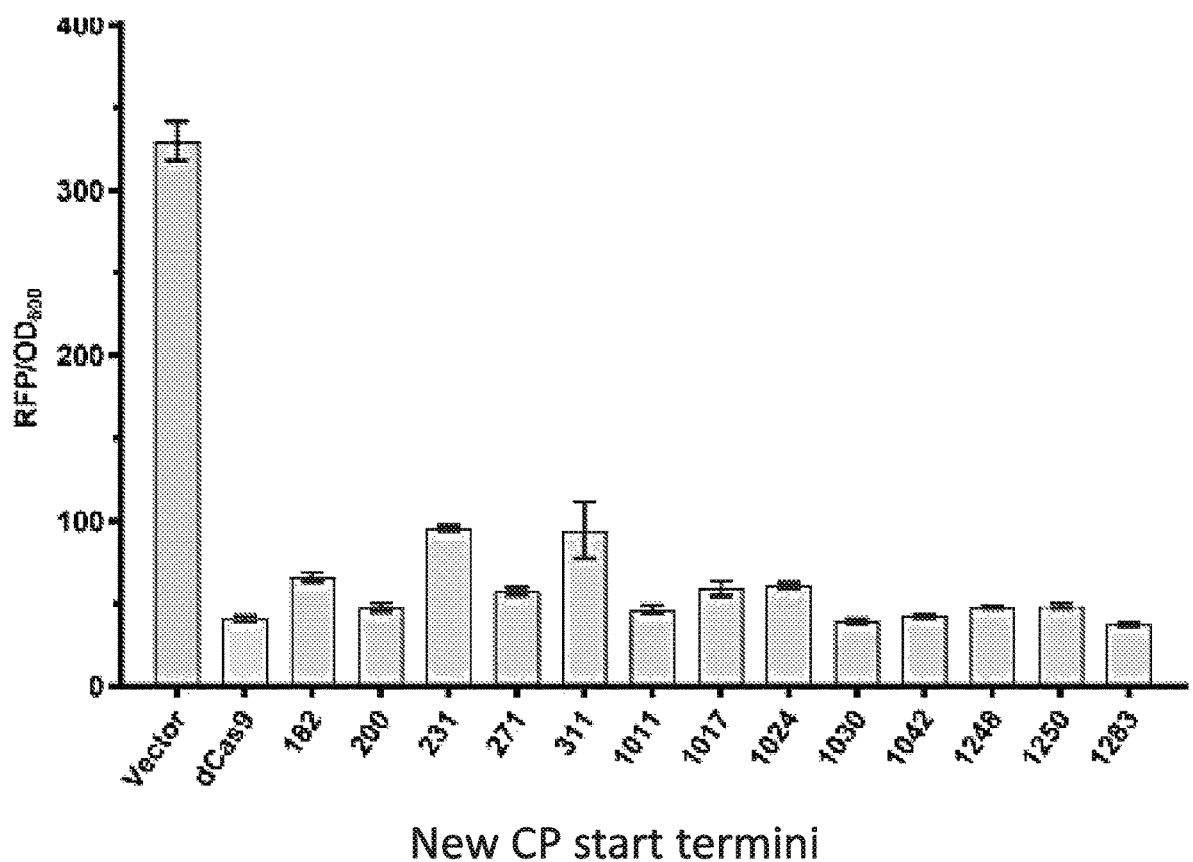
FIG. 8 presents data from a larger subset of the functional cp sites from the deep sequencing data (e.g., see FIG. 4) tested for CRISPRi based binding and repression in *E. coli*.
Figure 9:
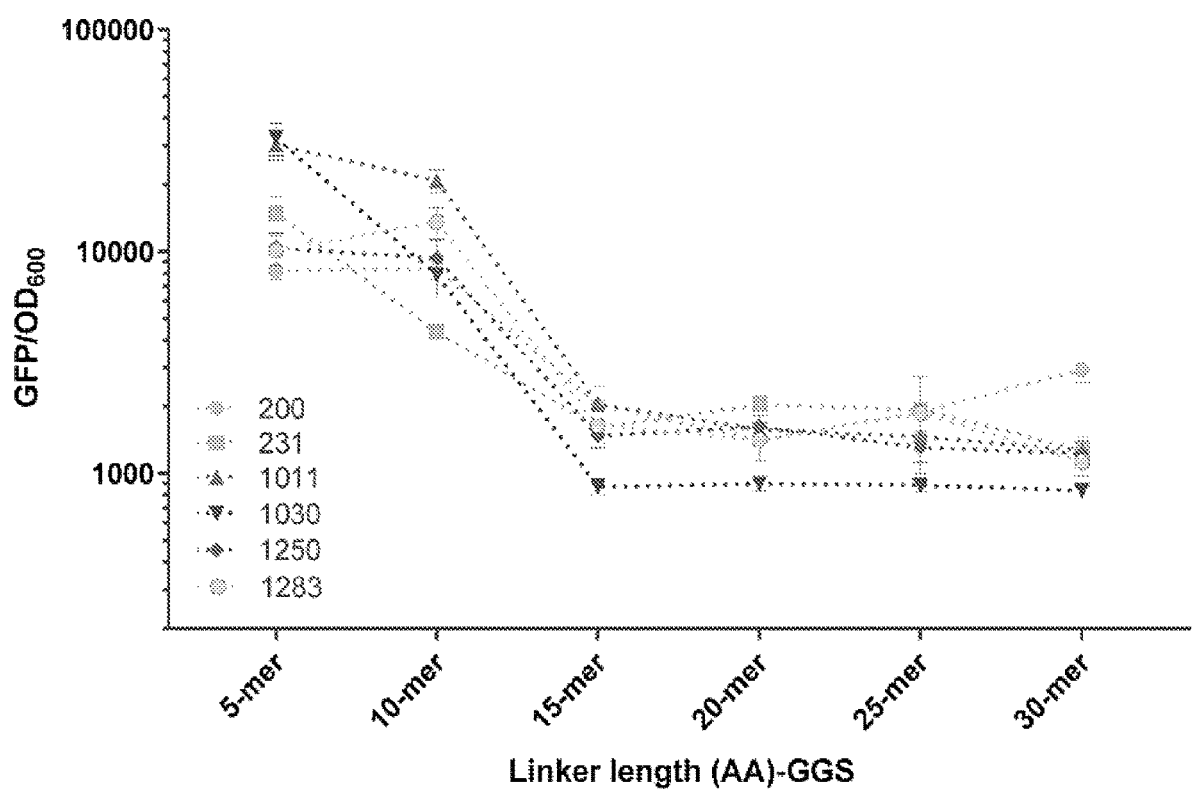
FIG. 9 presents data from a subset of the functional cp sites from the deep sequencing data (e.g., see FIG. 4) tested for CRISPRi based binding and repression in *E. coli* based on the linker length between the original N- and C-termini.

FIG. 8. A larger subset of the functional cp sites from the deep sequencing data (e.g., see FIG. 4) was tested for CRISPRi based binding and repression in E. coli FIG. 9. A subset of the functional cp sites from the deep sequencing data (e.g., see FIG. 4) was tested for CRISPRi based binding and repression in E. coli based on the linker length between the original N& C termini. The data showed that longer linkers worked better, up to 15 amino acids, at which point longer linkers did not improve function further (i.e., linkers above 15-mers worked generally just as well as 15-mer linkers).

FIG. 10 (panels A-B). (panel A) Schematic of the ability to cage cas9 based on linker length (e.g., see FIG. 4 and FIG. 5) and a protease target site as a short linker (panel B) Data demonstrating that specific circular permuted Cas9 proteins with the TEV recognition site (ENLYFQS) as the linker sequence became uncaged (activated) only in the presence of an active TEV protease (e.g., cp2).

Figure 11:
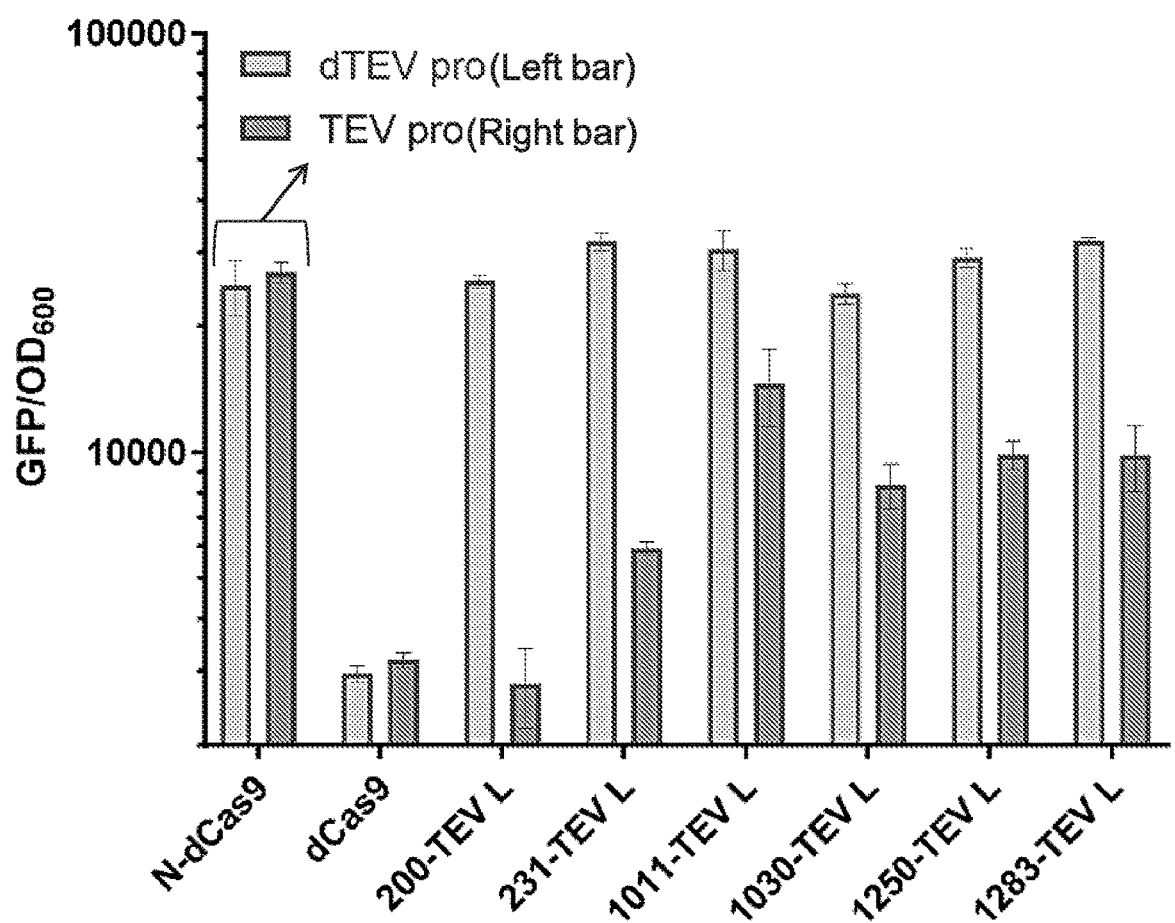
FIG. 11 (panels A-B) presents data from a subset of the functional cp sites from the deep sequencing data (e.g., see FIG. 4) tested for CRISPRi based binding and repression in *E. coli* with a TEV linker (ENLYFQ\S; SEQ ID NO:76) between the N- and C-termini and with or without an active TEV protease in the cells.
Figure 11:
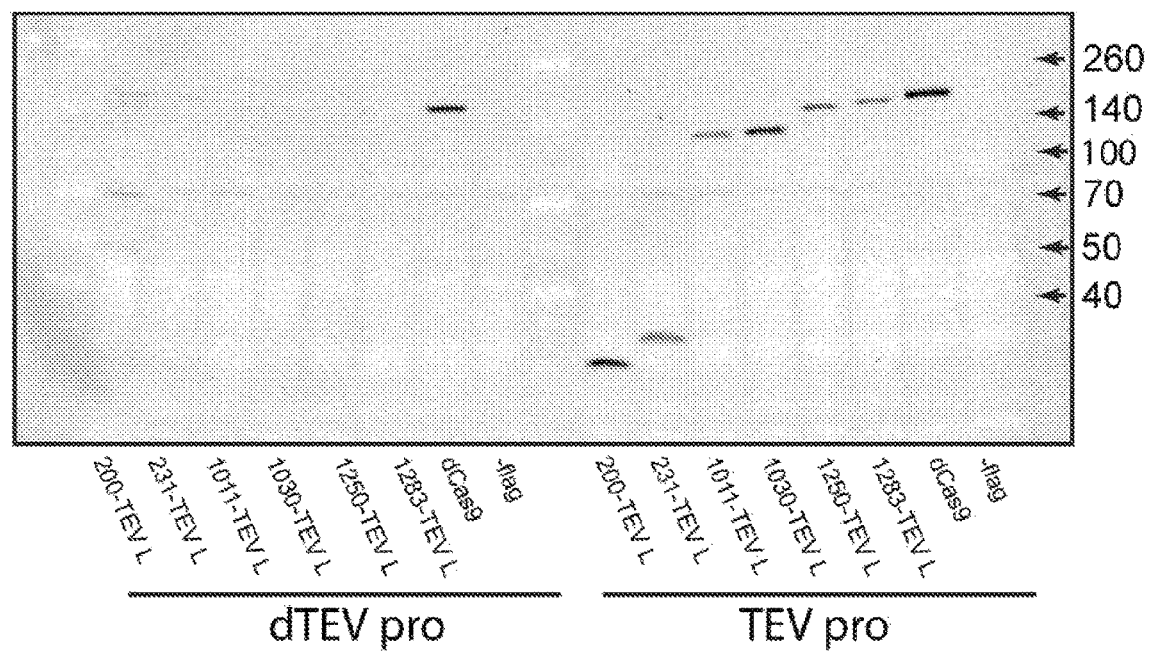

FIG. 11 (panel A) A subset of the functional cp sites from the deep sequencing data (e.g., see FIG. 4) was tested for CRISPRi based binding and repression in E. coli with a TEV linker (ENLYFQ\S) between the N & C termini and with or without an active TEV protease in the cells. dcas9 binding and repression activity was only evident when an active TEV (right) was present in the E. coli cells—indicating switching (switching "on" of the Cas9 cp by cleavage of the linker). (panel B) A western blot from the assay in panel-A demonstrating that the CPs were cleaved at the correct location when an active TEV protease was present in the cell.

Figure 12:
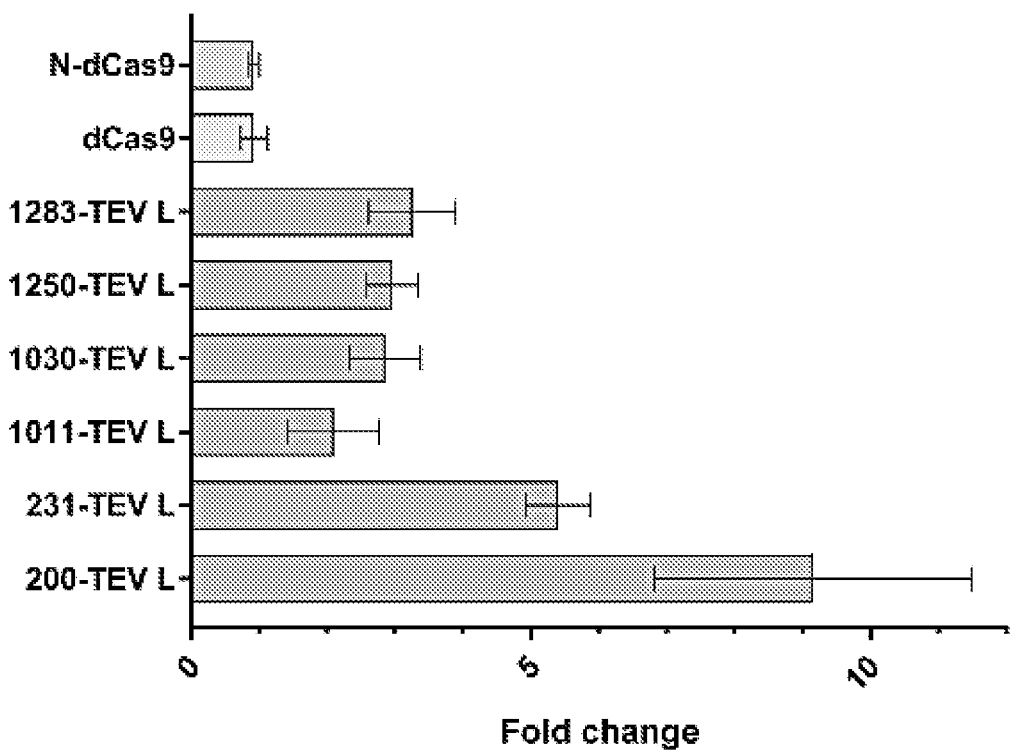
FIG. 12 (panels A-B) presents fold change data for activity from the previous assay demonstrating TEV based activation of the Cas9 circular permutant (cp); and presents single cell analysis of the Switching TEV constructs.
Figure 12:
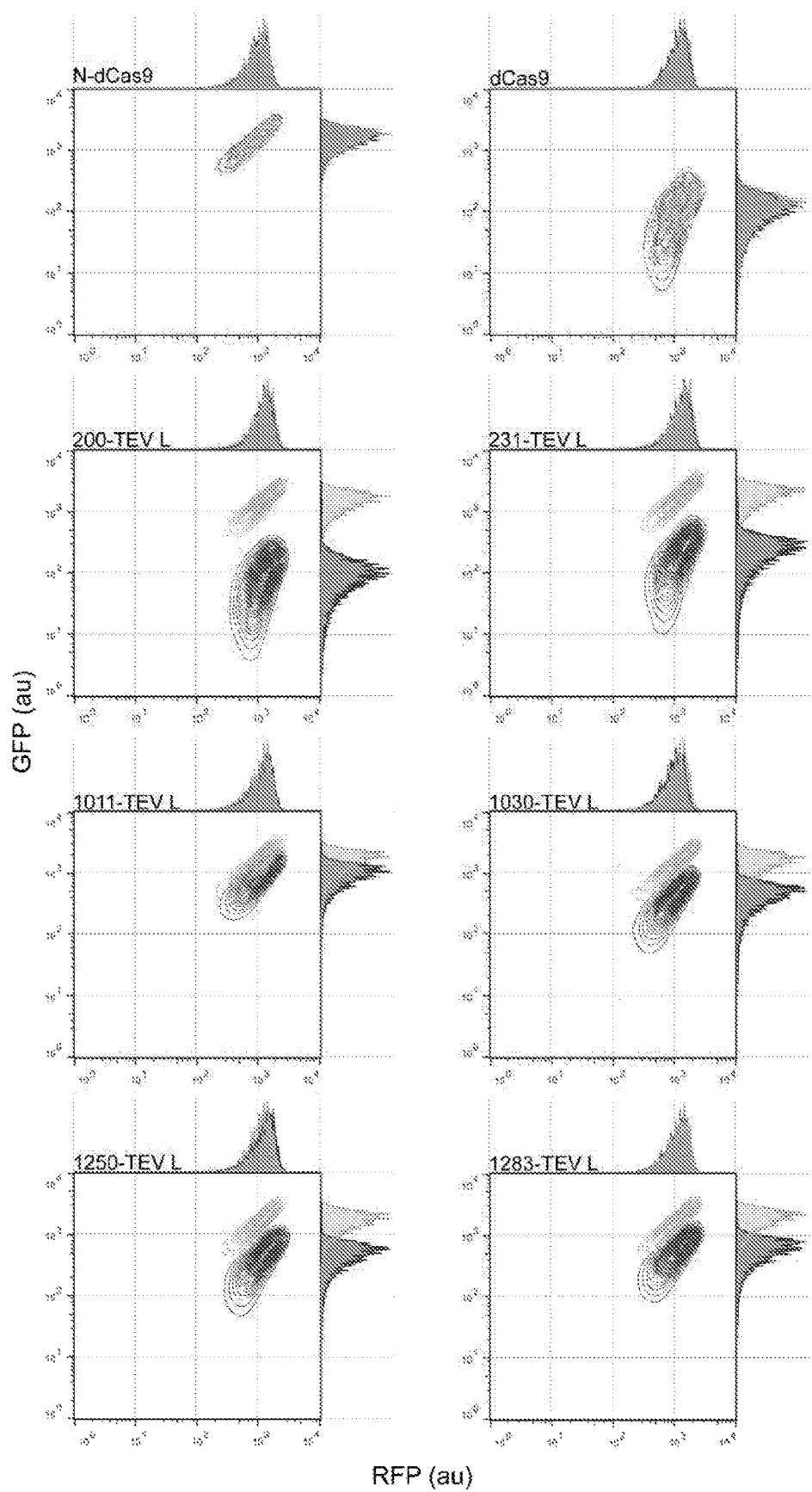

FIG. 12 (panel A) The fold change in activity from the previous assay demonstrating TEV based activation of the Cas9 circular permutant (cp). (panel B) single cell analysis of the Switching TEV constructs depicting robust switching o the entire population at a single cell level.

Figure 13:
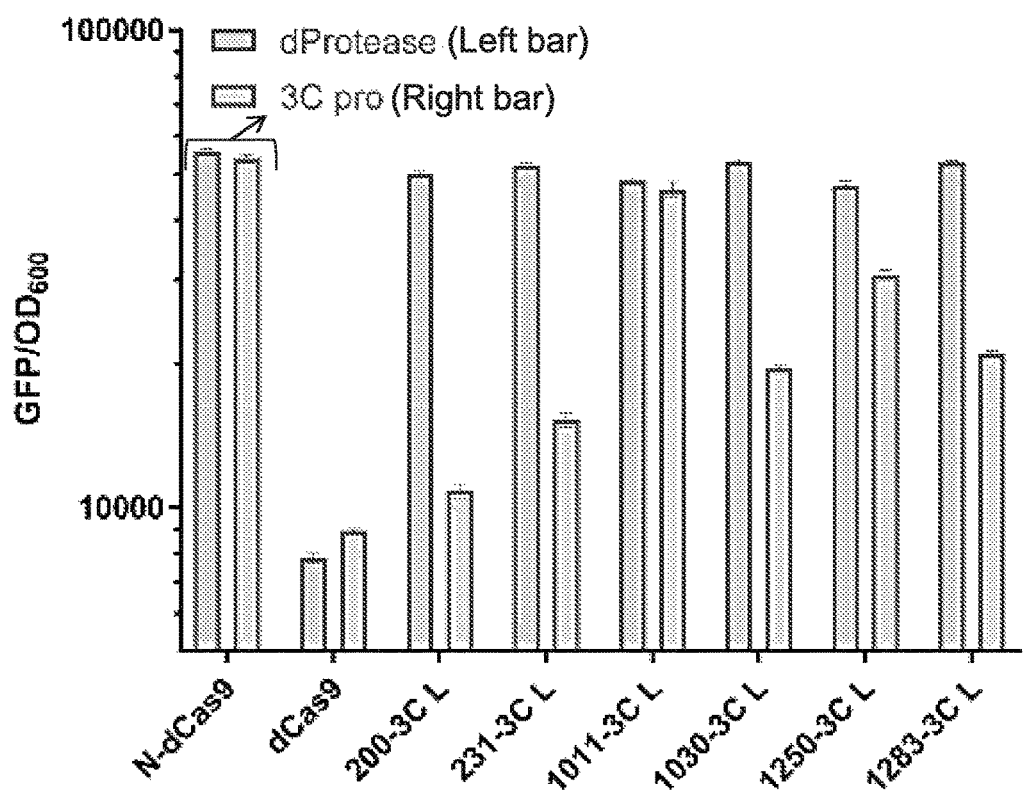
FIG. 13 presents data from testing a subset of the functional cp sites from the deep sequencing data (e.g., see FIG. 4) for CRISPRi based binding and repression in *E. coli* with a rhinovirus 3C cleavable linker (LEVLFQ/GP; SEQ ID NO:100) between the N- and C-termini and with or without an active 3C protease (also known as PreScission Protease).

FIG. 13. A subset of the functional cp sites from the deep sequencing data (e.g., see FIG. 4) was tested for CRISPRi based binding and repression in E. coli with a rhinovirus 3C cleavable linker (LEVLFQ/GP) between the N & C termini and with or without an active 3C protease (also known as PreScission Protease).

Figure 14:
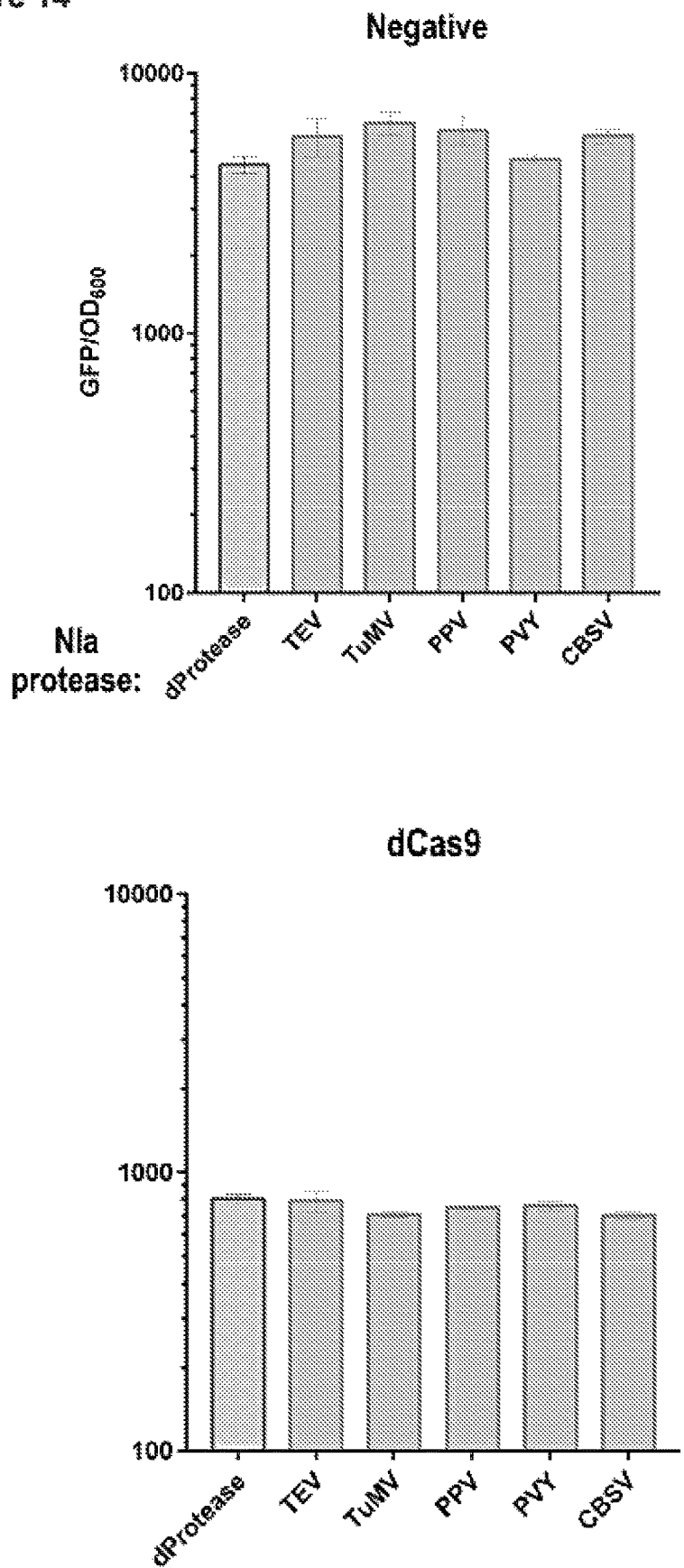
FIG. 14 presents data from testing CP 200 (cpCas9-200) (i.e., circular permutant—amino acid position 200; the best responder from the previous assays) in CRISPRi based binding and repression in *E. coli* with various potyvirus proteases and between the N- and C-termini and with or without an active Nia proteases. TEV (ENLYFQSM; SEQ ID NO:102); TuMV (GGCSHQS; SEQ ID NO:52); PPV (QVVVHQSK; SEQ ID NO:54); PVY (YDVRHQSR; SEQ ID NO:103); CBSV (GLVEVQGR; SEQ ID NO:57).
Figure 14:
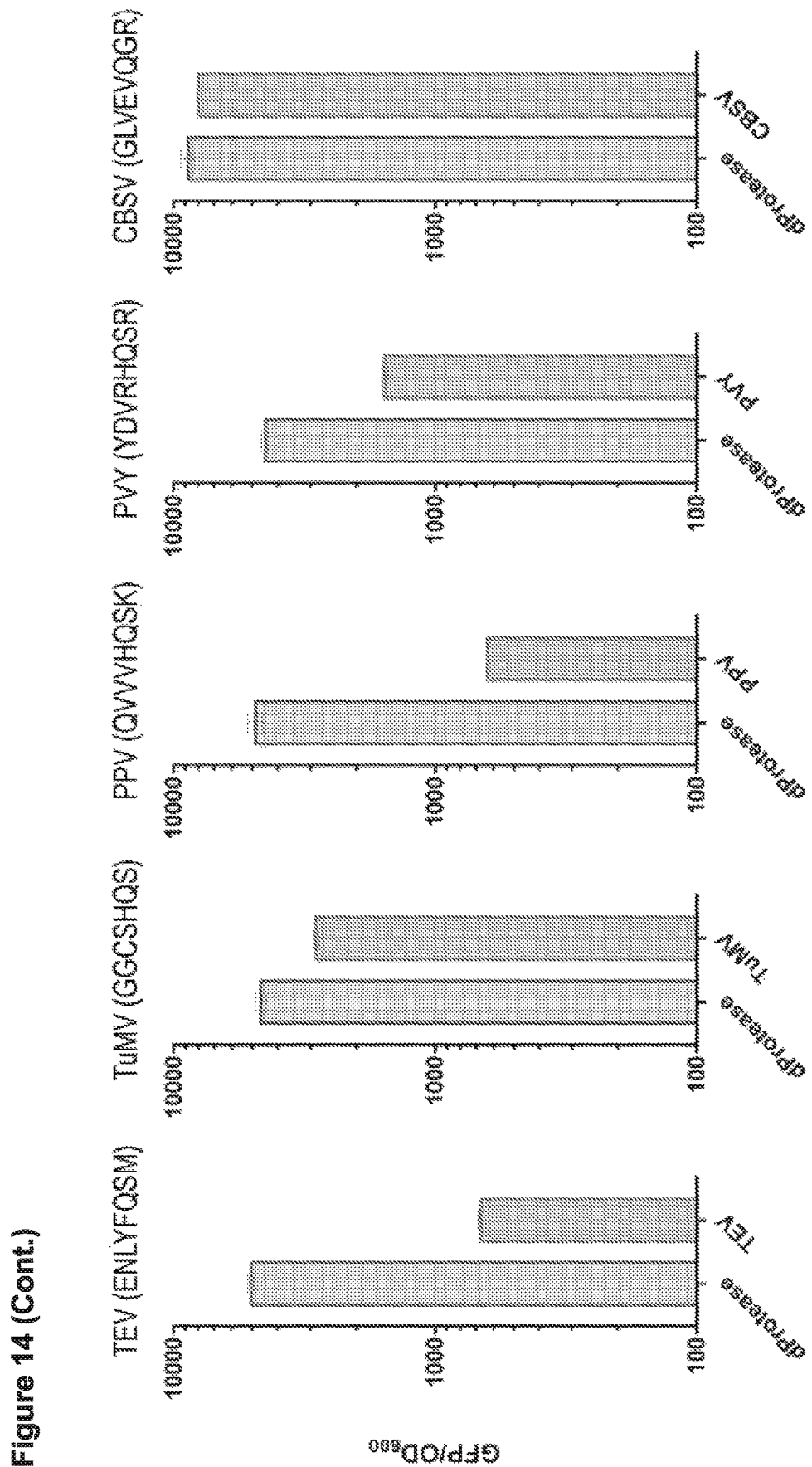

FIG. 14. CP 200 (cpCas9-200) (i.e., circular permutant—amino acid position 200; the best responder from the previous assays) was tested in CRISPRi based binding and repression in E. coli with various potyvirus proteases and between the N & C termini and with or without an active Nia proteases.

Figure 15:
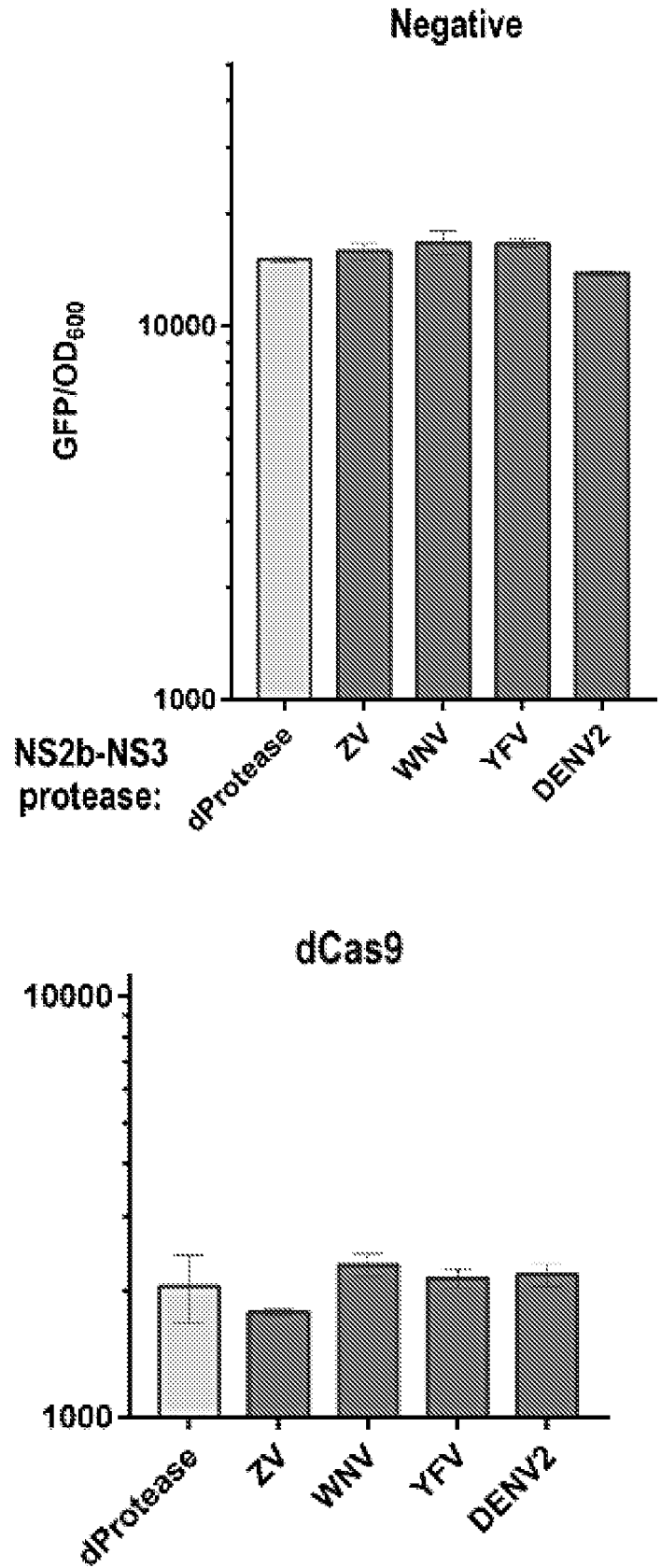
FIG. 15 presents data from testing CP 200 (cpCas9-200) (i.e., circular permutant—amino acid position 200) in CRISPRi based binding and repression in *E. coli* with various flavi virus NS2b-NS3 proteases and between the N- and C-termini and with or without an active proteases. Cp-linkers: ZV (KERKRRGA; SEQ ID NO:104); WNV (KQKKRGGK; SEQ ID NO:105); DENV2 (NRRRRSAG; SEQ ID NO:67); YFV (SSRKRRSH; SEQ ID NO:106).

FIG. 15 CP 200 (cpCas9-200) (i.e., circular permutant—amino acid position 200) was tested in CRISPRi based binding and repression in E. coli with a various flavi virus NS2b-NS3 proteases and between the N & C termini and with or without an active proteases.

Figure 16:
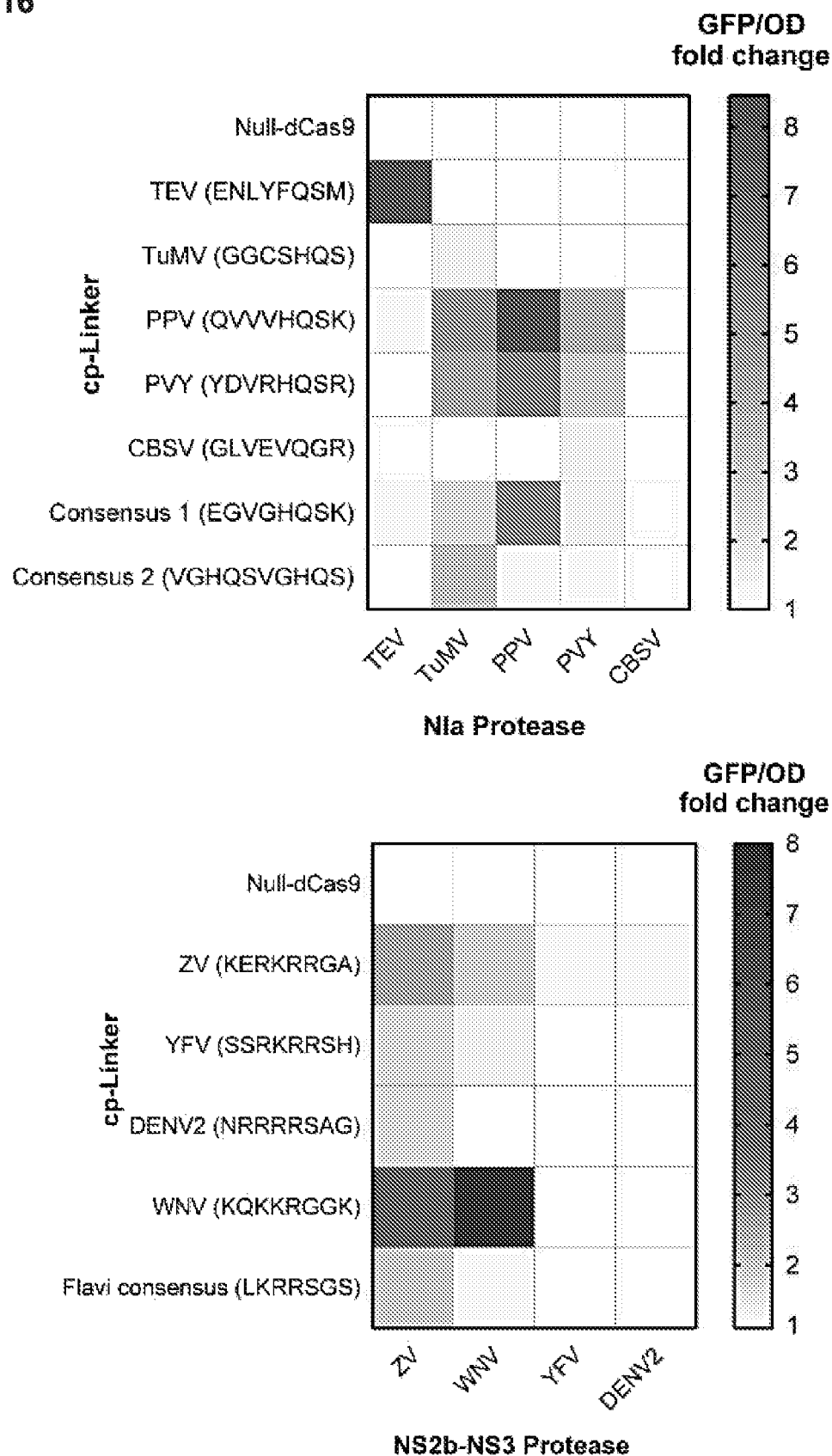
FIG. 16 presents data from testing CP 200 (cpCas9-200) (i.e., circular permutant—amino acid position 200) in CRISPRi based binding and repression in *E. coli* in all linker vs all protease tests demonstrating the ability to create a Synthetic Immune Response Element (SIRE) that can recognize and turn on in response to various of viral proteases for poty and flavi viruses respectively. TEV (ENLYFQSM; SEQ ID NO:102); TuMV (GGCSHQS; SEQ ID NO:52); PPV (QVVVHQSK; SEQ ID NO:54); PVY (YDVRHQSR; SEQ ID NO:103); CBSV (GLVEVQGR; SEQ ID NO:57) Consensus 1 (EGVGHQSK; SEQ ID NO:18); Consensus 2 (VGHQSVGHQS; SEQ ID NO:19). Cp-linkers: ZV (KERKRRGA; SEQ ID NO:104); YFV (SSRKRRSH; SEQ ID NO:106); DENV2 (NRRRRSAG; SEQ ID NO:67); WNV (KQKKRGGK; SEQ ID NO:105); Flavi consensus (LKRRSGS; SEQ ID NO:73).

FIG. 16 presents CP 200 (cpCas9-200) (i.e., circular permutant—amino acid position 200) was tested in CRISPRi based binding and repression in E. coli in all linker vs all protease tests demonstrating the ability to create a Synthetic Immune Response Element (SIRE) that can recognize and turn on in response to various of viral proteases for poty and flavi viruses respectively.

Figure 17:
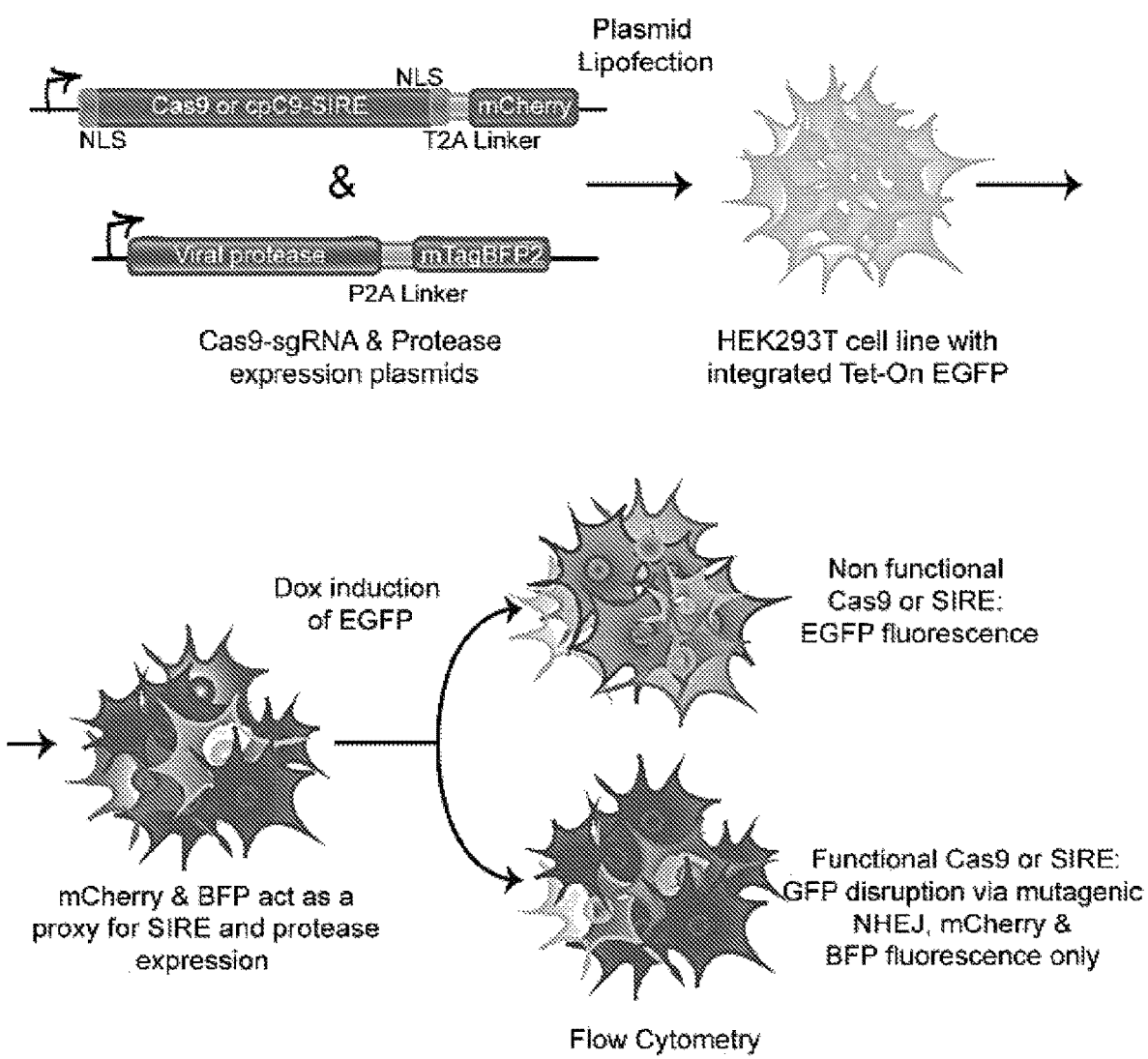
FIG. 17 presents a schematic depiction of one possible example of a Synthetic Immune Response Element (SIRE); and also presents data demonstrating the ability of SIREs to turn on in response to a variety of viral proteases in eukaryotic cells (human cells in this case). QVVVHQSK (SEQ ID NO:54). KQKKRGGK (SEQ ID NO:105).
Figure 17:
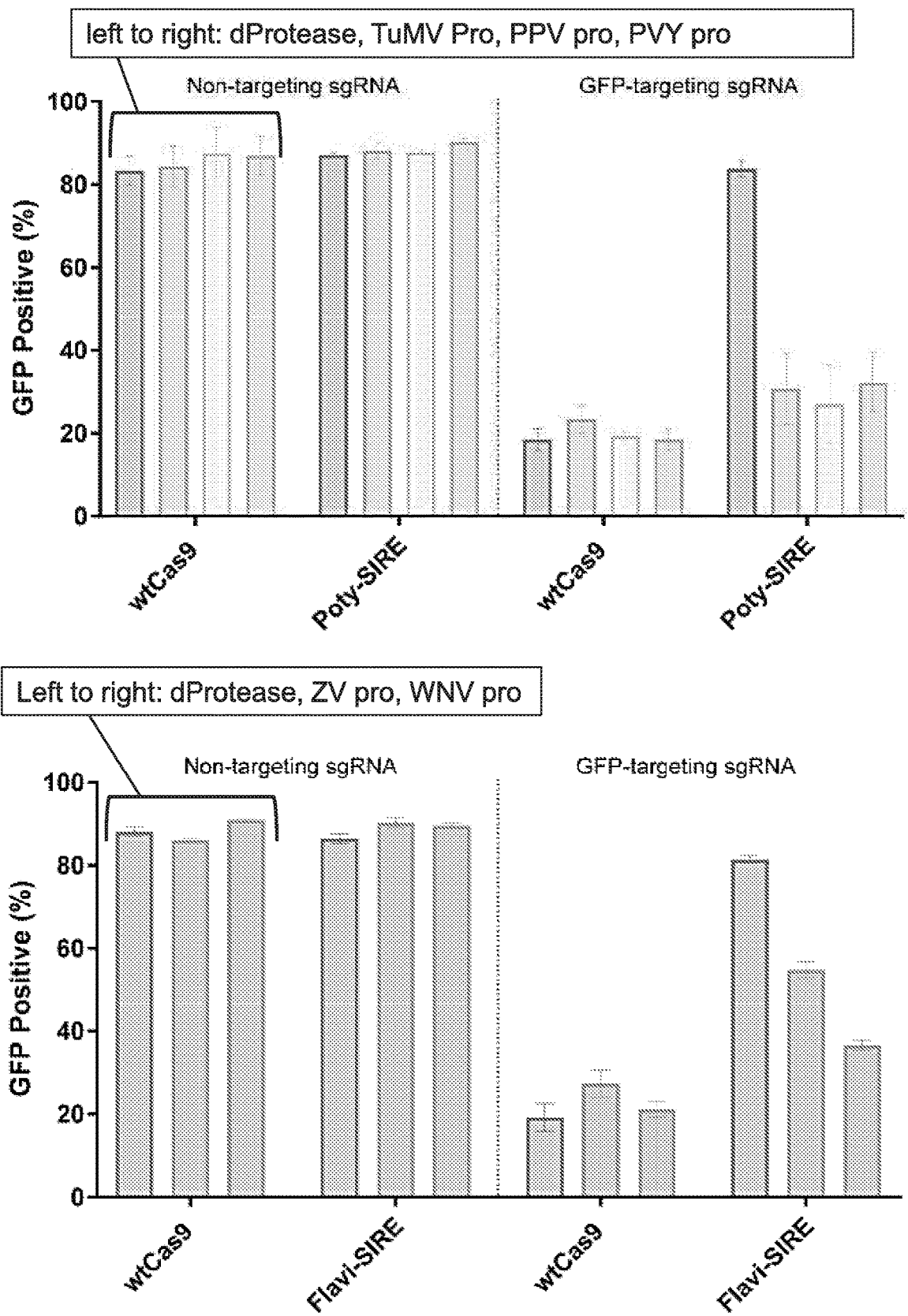

FIG. 17. The schematic depicts how a Synthetic Immune Response Element (SIRE). The data demonstrate the ability of SIREs to turn on in response to a variety of viral proteases (poty and flavi viruses for the Poty-SIRE and Favi-SIREs respectively) in human embryonic kidney (HEK) cells.

Figure 18:
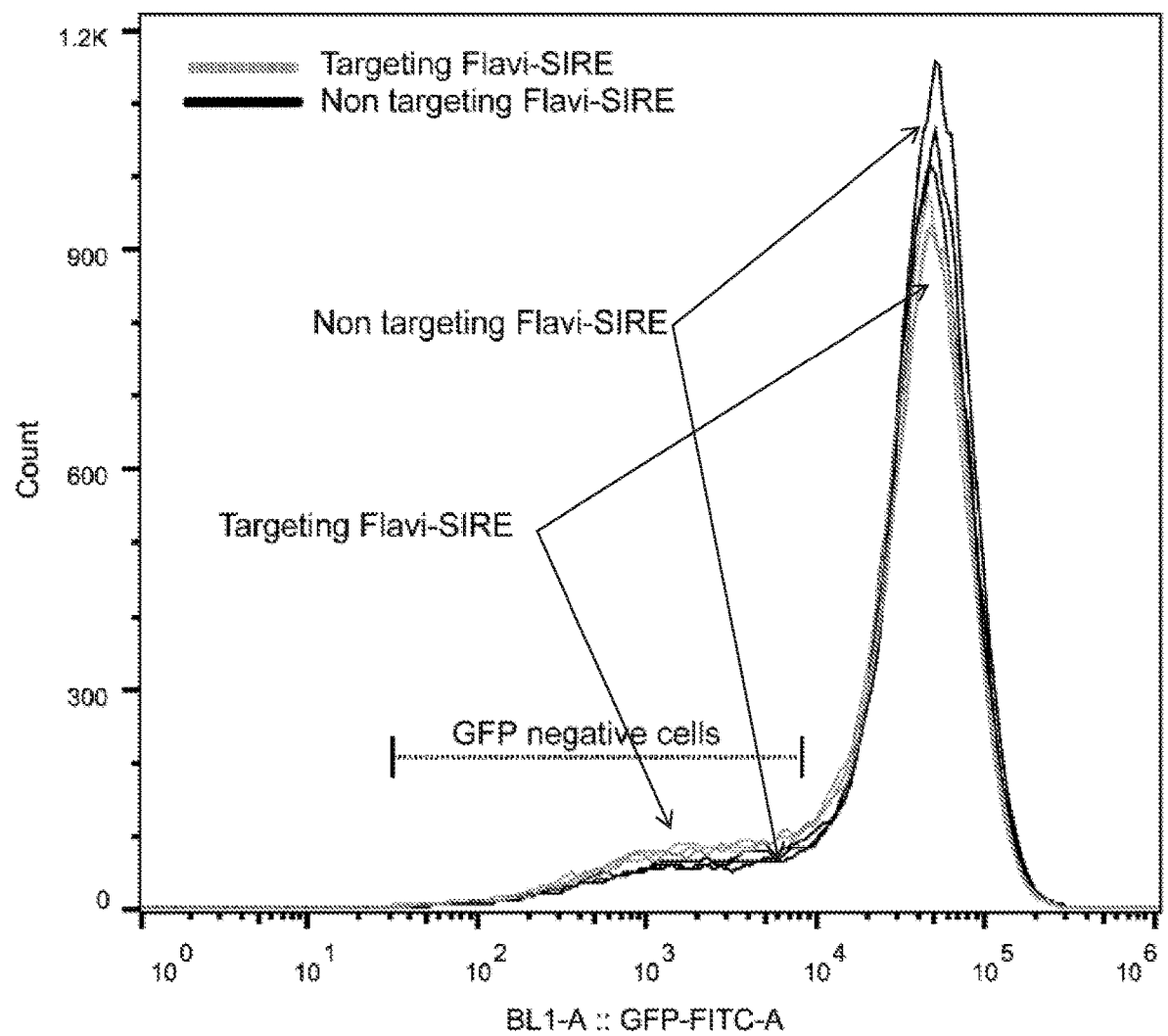
FIG. 18 presents data showing leakiness in the human cell editing without proteases present.

FIG. 18. Demonstration of leakiness in the human cell editing without proteases present.

Figure 19:
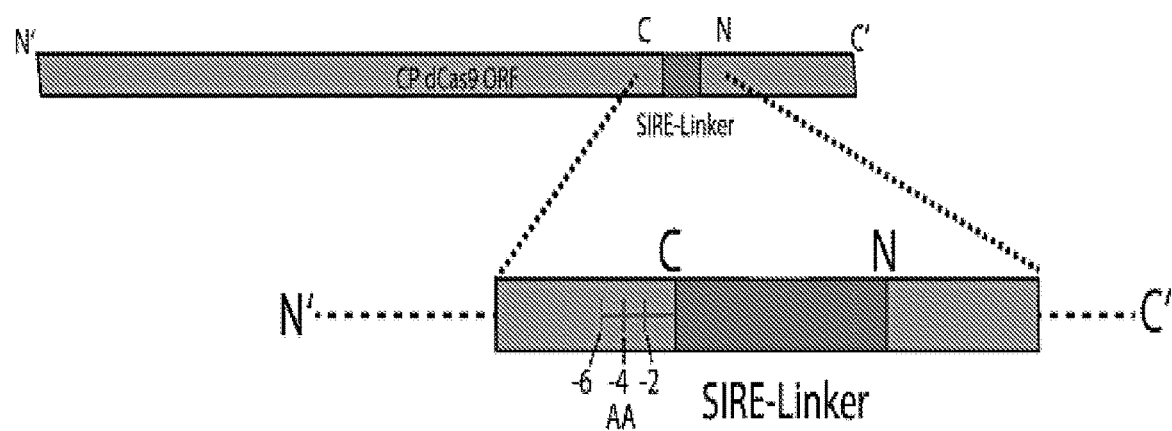
FIG. 19 presents a schematic and data showing end trimming and its ability to reduce background activity of the system to background levels in HEK cells—and to activate in the presence of the correct protease.

FIG. 19. Schematic of end trimming and its ability to reduce background activity of the system to background levels in HEK cells, and activate in the presence of the correct protease.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11180778B2). An electronic copy of the "Sequence Listing" will also be available from the USPTO upon request and payment of the fee set forth in 37 CFR 1.19(b)(3).

What is claimed is:

1. A variant Cas9 polypeptide comprising, in order from N-terminus to C-terminus:
   (a) a C-terminal fragment of a parent Cas9 polypeptide;
   (b) a linker; and
   (c) an N-terminal fragment of the parent Cas9 polypeptide, wherein said N-terminal fragment comprises an amino acid sequence corresponding to amino acids 1-182, 1-200, 1-231, 1-271, 1-311, 1-1011, 1-1017, 1-1024, 1-1029, 1-1030, 1-1032, 1-1042, 1-1245, 1-1249, 1-1250, or 1-1283 of the amino acid sequence set forth in SEQ ID NO: 17 or 111,
   and wherein the parent Cas9 polypeptide comprises, in order from N- to C-terminus:
   i) a first RuvC subdomain;
   ii) a second RuvC subdomain;
   iii) an HNH domain; and
   iv) a third RuvC subdomain.

2. The variant Cas9 polypeptide of claim 1, wherein the linker is a polypeptide linker.

3. The variant Cas9 polypeptide of claim 1, wherein the linker is a cleavable linker.

4. The variant Cas9 polypeptide of claim 3, wherein the cleavable linker is a polypeptide linker comprising a target sequence for a protease.

5. The variant Cas9 polypeptide of claim 4, wherein the protease is a viral, fungal, or bacterial protease.

6. The variant Cas9 polypeptide of claim 3, wherein the variant Cas9 polypeptide is conditionally active, having reduced activity when the cleavable linker is uncleaved relative to when the cleavable linker is cleaved.

7. The variant Cas9 polypeptide of claim 6, wherein activity of the variant Cas9 polypeptide when the cleavable linker is cleaved is 1.1-fold or more relative to the activity of the variant Cas9 polypeptide when the cleavable linker is uncleaved.

8. The variant Cas9 polypeptide of claim 6, wherein the linker has a length equivalent to a range of from 1 to 10 amino acids.

9. The variant Cas9 polypeptide of claim 1, wherein the linker has a length equivalent to 11 or more amino acids.

10. The variant Cas9 polypeptide of claim 1, wherein the C-terminal amino acid of said N-terminal fragment corresponds to
    amino acid 182D, 200P, 231G, 271Y, 311E, 1011G, 1017D, 1024K, 1029I, 1030G, 1032A, 1042I, 1245L, 1249P, 1250E, or 1283A of the amino acid sequence set forth in SEQ ID NO: 111 or SEQ ID NO: 17 or 111.

11. The variant Cas9 polypeptide of claim 1, comprising an amino acid sequence having 85% or more identity with the amino acid sequence set forth in any one of SEQ ID NOs: 1-16, wherein the stretch of Xs within the sequences set forth in SEQ ID NOs: 1-16 marks the position of the linker.

12. The variant Cas9 polypeptide of claim 1, wherein the parent variant Cas9polypeptide comprises an amino acid sequence having 85% or more identity with the amino acid sequence set forth in any one of SEQ ID NOs: 17 and 111-912.

13. The variant Cas9 polypeptide of claim 1, wherein the variant Cas9 polypeptide lacks a catalytically active RuvC domain and/or lacks a catalytically active HNH domain.

14. The variant Cas9polypeptide of claim 1, wherein the RNA-guided polypeptide is fused to a heterologous polypeptide.

15. The variant Cas9 polypeptide of claim 14, wherein the RNA-guided polypeptide is fused to a transcription activation domain or a transcription repressor domain.

16. A method of binding a target nucleic acid, comprising contacting a target nucleic acid with a guide RNA and the variant Cas9 polypeptide of claim 1.

17. The method of claim 16, wherein said contacting comprises introducing into a cell:
    (a) a DNA or RNA encoding the variant Cas9 polypeptide of claim 1; and a DNA encoding the guide RNA; or
    (b) a ribonucleoprotein (RNP) complex comprising (i) the guide RNA and (ii) the variant Cas9 polypeptide of claim 1.

* * * * *